(12) United States Patent
Sammak et al.

(10) Patent No.: US 6,716,588 B2
(45) Date of Patent: Apr. 6, 2004

(54) SYSTEM FOR CELL-BASED SCREENING

(75) Inventors: Paul Sammak, Pittsburgh, PA (US); Thomas D. Duensing, Gibsonia, PA (US); Richard A. Rubin, Pittsburgh, PA (US)

(73) Assignee: Cellomics, Inc., Pittsburgh, PA (US)

( * ) Notice: Subject to any disclaimer, the term of this patent is extended or adjusted under 35 U.S.C. 154(b) by 0 days.

(21) Appl. No.: 09/733,273

(22) Filed: Dec. 8, 2000

(65) Prior Publication Data

US 2001/0041347 A1 Nov. 15, 2001

Related U.S. Application Data

(60) Provisional application No. 60/170,087, filed on Dec. 9, 1999.

(51) Int. Cl.[7] .............................................. G01N 33/533
(52) U.S. Cl. ........................ 435/7.2; 435/7.2; 435/7.21; 435/7.23; 435/288.3; 435/288.4; 436/63; 436/172; 436/164; 356/326; 356/328; 356/300; 382/133; 382/141
(58) Field of Search ........................... 436/63, 518, 164, 436/524, 172, 527, 546; 435/4, 6, 29, 30, 34, 7.2, 7.21, 7.23, 287.8, 287.9, 40.5, 40.51, 288.3, 288.4; 422/60, 63; 364/413.01, 413.08, 497, 555; 356/39; 382/133, 141

(56) References Cited

U.S. PATENT DOCUMENTS

| | | | |
|---|---|---|---|
| 4,344,816 A | | 8/1982 | Craighead et al. |
| 4,673,988 A | | 6/1987 | Jansson et al. |
| 4,762,701 A | | 8/1988 | Horan et al. |
| 4,783,401 A | | 11/1988 | Horan et al. |
| 4,859,584 A | | 8/1989 | Horan et al. |
| 4,982,739 A | | 1/1991 | Hemstreet et al. |
| 5,031,797 A | | 7/1991 | Boris et al. |
| 5,096,807 A | | 3/1992 | Leaback |
| 5,143,854 A | | 9/1992 | Pirrung et al. |
| 5,233,369 A | | 8/1993 | Carlotta et al. |
| 5,313,264 A | | 5/1994 | Ivarrson et al. |
| 5,324,591 A | | 6/1994 | Georger, Jr. et al. |
| 5,326,691 A | | 7/1994 | Hozier |
| 5,330,911 A | * | 7/1994 | Hubbell et al. ......... 435/240.23 |
| 5,384,261 A | | 1/1995 | Winkler et al. |
| 5,401,629 A | | 3/1995 | Harpold et al. |
| 5,436,128 A | | 7/1995 | Harpold et al. |
| 5,466,667 A | * | 11/1995 | Shepro et al. ................. 514/11 |
| 5,486,855 A | | 1/1996 | Carlotta et al. |
| 5,491,084 A | | 2/1996 | Chalfie et al. |
| 5,500,071 A | | 3/1996 | Kaltenbach |
| 5,502,467 A | | 3/1996 | Hoisington et al. |
| 5,526,258 A | * | 6/1996 | Bacus ..................... 364/413.1 |
| 5,527,673 A | | 6/1996 | Reinhartz et al. |
| 5,556,752 A | | 9/1996 | Lockhart et al. |
| 5,567,294 A | | 10/1996 | Dovichi et al. |
| 5,571,410 A | | 11/1996 | Swedberg et al. |
| 5,581,487 A | | 12/1996 | Kelly et al. |
| 5,585,069 A | | 12/1996 | Zanzucchi et al. |
| 5,599,681 A | | 2/1997 | Epstein et al. |
| 5,885,840 A | * | 3/1999 | Kamentsky et al. .......... 436/63 |
| 5,919,646 A | | 7/1999 | Okun et al. |
| 5,989,835 A | | 11/1999 | Dunlay et al. |
| 6,103,479 A | * | 8/2000 | Taylor ........................ 435/7.2 |

FOREIGN PATENT DOCUMENTS

| | | |
|---|---|---|
| WO | WO 87/02802 | 5/1987 |
| WO | WO 95/07463 | 3/1995 |
| WO | WO 95/21191 | 8/1995 |
| WO | WO 96/09598 | 3/1996 |
| WO | WO 96/23898 | 8/1996 |
| WO | WO 96/27675 | 9/1996 |
| WO | WO 97/43732 | 11/1997 |
| WO | WO 98/38490 | 9/1998 |
| WO | WO 00/03246 | 1/2000 |
| WO | WO 00/17643 | 3/2000 |
| WO | WO 00/26408 | 5/2000 |
| WO | WO 00/50872 | 8/2000 |
| WO | WO 00/70342 | 11/2000 |
| WO | WO 00/79241 | 12/2000 |
| WO | WO 01/11340 | 2/2001 |
| WO | WO 01/11341 | 2/2001 |
| WO | WO 01/35072 | 5/2001 |
| WO | WO 01/42786 | 6/2001 |

OTHER PUBLICATIONS

Brugmans et al., Quantification of the degree of cell spreading of human fibroblasts by semi–automated analysis of the cell perimeter. Cytometry (1983) 3(4): 262–268 (Abstract).*
Madeja et al., Morphometric analysis of LPS–stimulated human monocytes by computer assisted image analysis, Folia Biologica (1998) 46(3–4): 123–128 (Abstract).*
Tanaka et al., Automated cytologic screening system (CYBEST model 4) an integrated image cytometry system, Applied Optics 26(16): 3301–3307.*
Bailey, et al., (1993), Nature, 366: pp. 44–48.
Barak et al., (1997), *J. Biol. Chem*, 272(44):27497–27500.
Barber et al., (1996), *Neuroscience Letters*, 207:17–20.
Beggs (1997), *J. of Biomolec. Screening*, 2(2):71–78.
Bell, Jr., et al., (1987), J. Histochem. And Cytochem., 35: pp. 1375–1380.
Bhatia, et al., (1993), Analytical Biochemistry, 208: pp. 197–205.
Brejc, et al., (1997), Proc. Natl. Acad. Sci., 94: pp. 2306–2311.
Bright et al., (1987), *J. Cell Biol.,* 104:1019–1033.
Federov et al., (1994), *J. Mol. Biol.,* 241:480–482.
Firestone et al., (1991), *Cytometry*, 12:195–206.
Frisch, et al., (1996), Bioconjugate Chem., 7: pp. 180–186.
Gerrittsen et al., (1997), *J. of Fluorescence*, 7(1):11–15.

(List continued on next page.)

Primary Examiner—Christopher L. Chin
Assistant Examiner—Gailene R. Gabel
(74) Attorney, Agent, or Firm—McDonnell Boehnen Hulbert & Berghoff

(57) ABSTRACT

The present invention provides automated systems, methods, screens, and software for the analysis of cell spreading. The invention involves providing cells containing fluorescent reporter molecules in an array of locations, contacting the cells with a test stimulus, acquiring images from the cells, and automatically calculating one or more morphological features that provide a measure of cell spreading.

12 Claims, 29 Drawing Sheets

OTHER PUBLICATIONS

Giuliano et al., (1995), *Curr. Op. Cell Biol.,* 7:4–12.
Giuliano et al., (1995), *Methods in Neuroscience,* 27:1–16.
Giuliano et al., (1987), *Anal. Biochem.,* 167:362–371.
Giuliano et al., (1990), Optical Microscopy for Biology pp. 543–557.
Giuliano et al., (1995), *Annu. Rev. of Biophysics and Biomolecular Structure,* 24:405–434.
Giuliano, (1996), *Cell Motil. Cytoskel.,* 35:237–253.
Go et al., (1997), *Analytical Biochemistry,* 247:210–215.
Goldmacher, et al., (1992), Bioconjugate Chem., 3: pp. 104–107.
Goldman et al., (1995), *Experimental Cell Research,* 221:311–319.
Gonzales et al., (1995), Biophysics J., 69: pp. 1272–1280.
Gonzales et al., (1987), *Digital Image Processing,* pp. 391–448.
Gough et al., (1993), *J. Cell Biol.,* 121(5):1095–1107.
Grabarek and Gergely, (1990), Anal. Biochem., 185: pp. 131–135.
Graham et al., (1973), *Virology,* 52:456–467.
Gratton et al., (1994), *Proc. of the Microscopical Society of America,* pp. 154–155.
Groen et al., (1985), *Cytometry,* 6:81–91.
Hahn et al., (1992), *Nature,* 359:736–738.
Hahn et al., (1993), *Fluorescent and Luminescent Probes for Biological Activity,* W.T. Mason, (ed.), pp. 349–359, Academic Press, San Diego.
Harms et al., (1984), *Cytometry,* 5:236–243.
Harootunian et al., (1993), *Mol. Biol. of the Cell,* 4:993–1002.
Haselhoff, et al., (1997), Proc. Natl. Acad. Sci., 94: pp. 2122–2127.
Haugland, Fluorescent Tracers of cell morphology and fluid flow, in handbook of Fluorescent Probes and Research Chemicals, $6^{th}$ edition, ed. By Spence, Molecular Probes, Inc. Eugene OR, pp. 325–331, (1996).
Heim and Tsien (1996), *Curr. Biol.,* 6:178–182.
Htun et al., (1996), *Proc. Natl. Acad. Sci.,* 93:4845–4850.
Hu et al., (1995), *FEBS Letters,* 369:331–334.
Johnson et al., (1996), *Cell,* 85:149–158.
Johnson et al., (1985), J. Electron Microscopy Tech., 2: pp. 129–138.
Kaether et al., (1995), *FEBS Letters,* 369:267–271.
Kahl, et al., (1997), J. Biomol. Screening, 2: pp. 33–40.
Kapur, et al., (1996), Journal of Biomedical Materials Research, 33: pp. 205–216.
Kebler et al., (1996), *FEBS Letters,* 395:225–227.
Kessler et al., (1991), *Spectrochimica Acta,* 47A(2):187–192.
Kislauskis et al., (1994), *J. Cell Biol.,* 127(2):441–451.
Kittler et al., (1985), *Computer Vision, Graphics, and Image Processing,* 30:125–147.
Kleinfeld, et al., (1988), J. Neuroscience, 8: pp. 4098–4120.
Lakowicz et al., (1992), *Anal. Biochem.,* 202:316–330.
Lambrechts et al., (1995), *Eur. J. Biochem.,* 230:281–286.
Lee et al., (1996), *Biochemistry,* 35:6010–6019.
Lee et al., (1997), *Biochemistry,* 36:2701–2708.
Liang et al., (1997), *J. of Molec. Biol.,* 274:291–302.
Lopez, et al., (1993), J. Am. Chem. Soc., 115: pp. 5877–5878.
Martinez–Zaguilan et al., (1996), *Am. J. Physiol.,* 270:C1438–C1446.
McCaffrey et al., (1996), *J. Biomolec. Screening,* 1(4):187–190.
McCann et al., (1997), *Proc. Natl. Acad. Sci.,* 94:5679–5684.
McKenzie, et al., (1988), J. Prot. Chem., 7: pp. 581–592.
McNeil et al., (1984), J. Cell Biol. 98: pp. 1556–1564.
McNeil, (1989), *Methods in Cell Biology,* 29: 153–173.
Morise et al., (1974), *Biochemistry,* 13(12):2656–2662.
Mrkisch and Whitesides, (1996), Ann. Rev. Biophys. Biomol. Struct., 25: pp. 55–78.
Oancea et al., (1998), The Journal of Cell Biology, 140(3):pp. 485–498.
Palm et al., (1997), *Nat. Struct. Biol.,* 4(5):361–365.
Pillai, (1987), In Organic Photochemistry vol. 9, ed. A. Padwa, Marcel Dekker, Inc. NY, pp. 225–323.
Pillai, (1980), Synthesis, pp. 1–26.
Poot, et al., (1996), J. Histochem. And Cytochem., 44: pp. 1363–1372.
Post et al., (1995), Mol. Biol. Of the Cell, 6: pp. 1755–1768.
Presley et al., (1997), *Nature,* 389:81–85.
Prime and Whitesides, Science, 252: pp. 1164–1167.
Ridler et al., (1978), *IEEE Trans. Systems, Man, and Cybernetics,* 8:630–632.
Rizzuto et al., (1992), Nature, 358: pp. 325–327.
Russ, (1992), *The Image Processing Handbook,* CRC Press Inc., 225–275.
Sawin, et al., (1993), In Biological Techniques: Fluorescent and Luminescent Probes for Biological Activity, ed., W.T. Mason, Academic Press, pp. 405–419.
Scneckenburger, et al., (1997), Photochemistry and Photobiology, 66(1), pp. 34–41.
Self et al., (1995), *Methods in Enzymology,* 256:3–10.
Self and Thompson, (1996), Nature Medicine, 2: pp. 817–820.
Senter, (1985), Photochem. And Photobiol., 42: pp. 231–237.
Shimoura et al., (1988), *J. of Biochemistry,* 251:405–410.
Schroeder and Neagle, (1996), J. Biomol. Screening, 1: pp. 75–80.
Sigal, et al., (1996), Anal. Chem., 68: pp. 490–497.
Singhvi, et al., (1994), Science, 264: pp. 696–698.
Southwick et al., (1990), *Cytometry,* 11:418–430.
Spargo, et al., (1994), PNAS, 91: pp. 11070–11074.
Stenger, et al., (1992), Journal of the American Chemical Society, 114: pp. 8435–8442.
Suh, et al., (1983), Proc. SPIE, 382: pp. 199–201.
Sutoh, (1982), *Biochemistry,* 21:3654–3661.
Swaninathan et al, (1997), Biophysics J., 72: pp. 1900–1907.
Tanaka et al., (1987), Applied Optics, 26(16): pp. 3301–3307.
Tanaka et al., (1995) *Methods in Enzymology,* 256:41–49.
Tarasova et al., (1997), The Journal of Biological Chemistry, 272(23): pp. 14817–14824.
Taylor et al., (1994), *J. Biol. Chem.,* 269(1):308–318.
Taylor et al., (1996), Intl. Soc. For Optical Engineering, 2678: 15–27.
Taylor et al., (1994), Toxicologic Pathology, 22: pp. 145–159.
Thevinin, et al., (1992), Eur. J. Biochem., 206: pp. 471–477.
Thomas et al., (1979), *Biochemistry,* 18(11):2210–2218.
Tsien, (1989), *Methods in Cell Biology,* 30:127–156.
Tyagi et al., (1996), *Nat. Biotechnol.,* 14:303–308.
Waggoner et al., (1996), *Hum. Pathol.,* 27:494–502.
Walker et al., (1993), J. Biol. Chem. 268:19552–19558.

Wang, (1989), Methods in Cell Biology, 29: pp. 1–12.
Ward et al., (1980), *Photochem. Photobiol.*, 31:611–615.
Welch et al., (1995), *In Vitro Cell. Dev. Biol–Animal.* 31:610–616.
Willner and Rubin, (1996), Chem. Int. Ed. Engl., 35: pp. 367–385.
Yen, et al., (1989), Makromol. Chem., 190: pp. 69–82.
Taylor et al., (1994), *J. Biol. Chem.,* 269(1):308–318.
Baldwin, (1996) *Annu. Rev. Immunol.,* 14:649–683.
Brugmans et al., (1983) *Cytometry,* 3(4):262–268.
Chow et al., (1997) *Science,* 278:1638–1641.
Cosco et al., (1995) *Cell,* 81:1137–1146.
Ding et al., (1998) *J. Biol. Chem.,* 273(44):28897–28905.
Hall et al., (1997) *Proc. Nat. Acad. Sci.,* 94:4733–4738.
Hall et al., (1999) *J. Biol Chem.,* 274(1):376–383.
Han et al., (1995) *Biochim. Biophys. Acta.,* 1265:224–227.
Hoey et al. (1998) *Curr. Opin. Genet. Dev.,* 8:582–587.
Jaaro et al., (1997) *Proc. Natl. Acad. Sci.* 94:3742–3747.
Kaech et al., (1996) *Neuron.,* 17:1189–1199.
Keβler et al., (1996) *FEBS Letters,* 395:225–227.
Kolega et al., (1993) *BioImaging,* 1:136–150.
Kuo et al., (1999) *Annu. Rev. Immunol.,* 17:149–187.
Liu et al., (1998) *Curr. Opin. Immunol.,* 10:271–278.
Masuda et al., (1998) *Cell Signal.,* 10(9):599–611.
Olson et al., (1995) *J. Cell Biol.,* 130(3):639–650.
Paolillo et al., (1999) *J. Biol. Chem.,* 274(10):6546–6552.
Proffitt et al., (1996) *Cytometry,* 24:204–213.
Ramakers et al., (1998) *Developmental Brain Research,* 108:205–216.
Rao et al., (1997) *Annu. Rev. Immunol.,* 15:707–747.
Rizzuto et al., (1995) *Curr. Biology,* 5(6):635–642.
Schaeffer et al., (1999) *Mol. Cell. Biol.,* 19(4):2435–2444.
Strehlow et al., (1998) *J. Biol. Chem.,* 273(43):28049–28056.
Taylor et al., (1992) *American Scientist,* 80:322–335.
Tibbles et al. (1999) *Cell. Mol. Life Sci.,* 55:1230–1254.
Zhao et al., (1999) *J. Biol Chem.,* 274(13):8355–8358.
Bright et al., (1989), *Methods in Cell Biology,* 30:157–192.
Bright et al., (1989), *J. Cell. Physiol.,* 141:410–419.
Bright et al., (1996), *Cytometry,* 24:226–233.
Chalfie et al., (1994), *Science,* 263:802–805.
Cohen, (1997), *Biochemical J.,* 326:1–16.
Coso et al., (1995) *Cell,* 81:1137–1146.
Cubitt et al., (1995), *Trends in Biochemical Science,* 20:448–455.
Daaka et al., (1998), *J. Biol. Chem.,* 273(2):685–688.
Davis et al., (1995), *Dev. Biology,* 170:726–729.
DeBiasio et al., (1996), *Mol. Biol. Cell,* 7:1259–1282.
Denk et al., (1990), *Science,* 248:73–76.
Deprez et al., (1997), *J. Biol. Chem.,* 272(28):17269–17275.

* cited by examiner 279 276 277 278

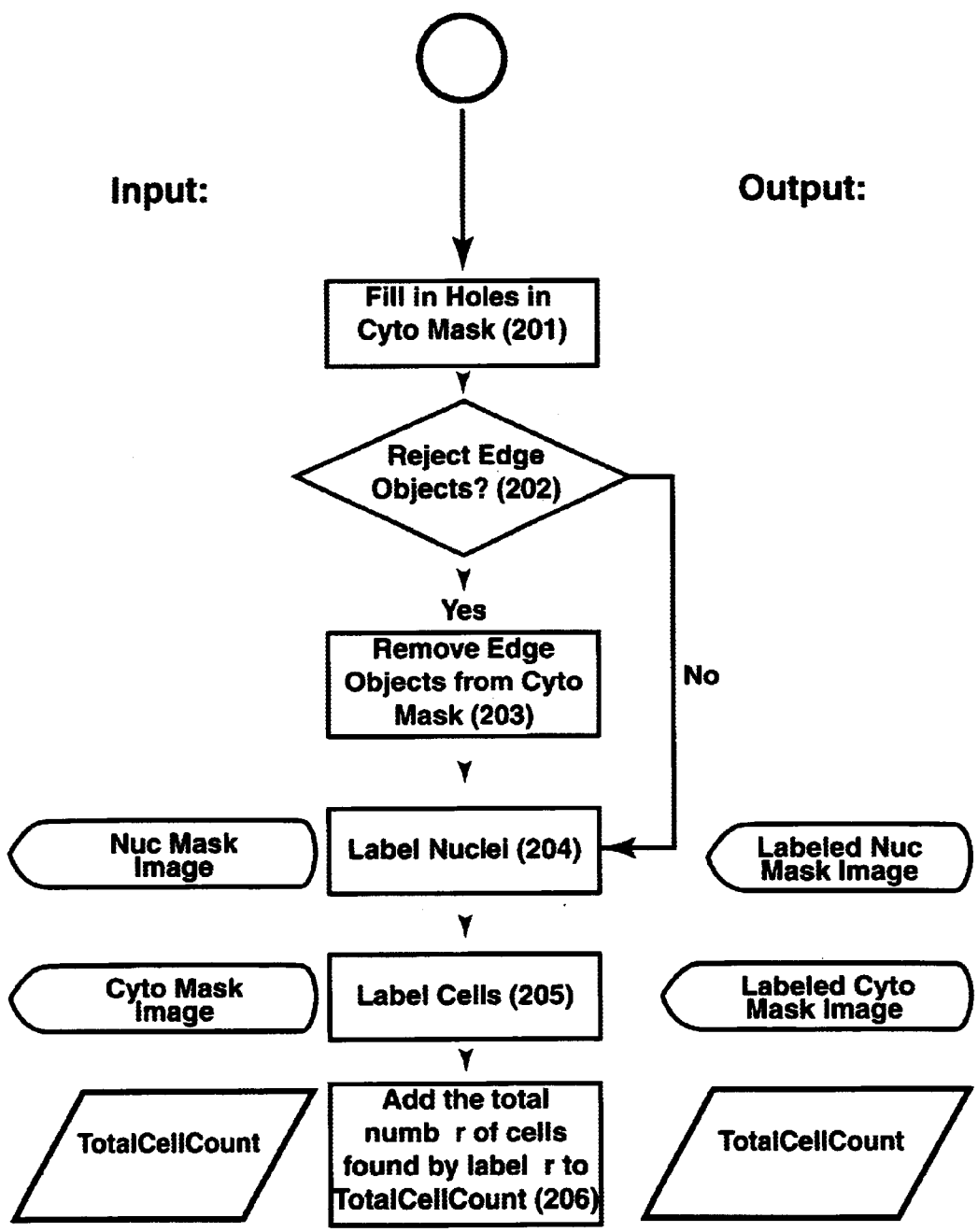

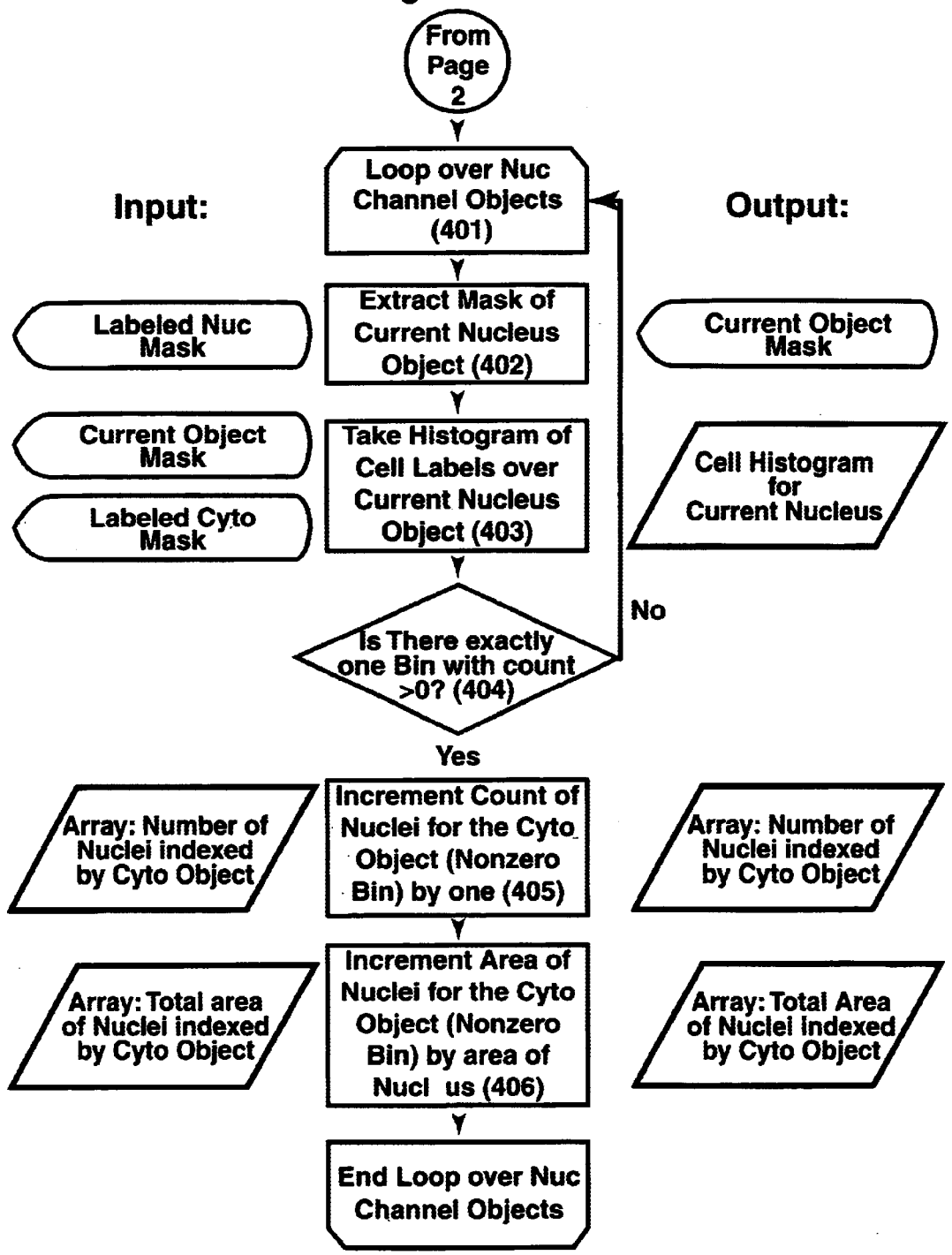

SYSTEM FOR CELL-BASED SCREENING

CROSS REFERENCE

This application claims priority to U.S. Provisional Patent Application Ser. No. 60/170,087, filed Dec. 9, 1999. The application is related to commonly owned applications Ser. No. 09/598,347 filed Jun. 21, 2000, pending; Ser. No. 09/352,171 filed Jul. 12, 1999, pending; 09/031,271 filed Feb. 27, 1998, abandoned; Ser. No. 09/293,209 filed Apr. 16, 1999, abandoned; Ser. No. 09/293,210 filed Apr. 16, 1999, now U.S. Pat. No. 6,620,591; Ser. No. 09/398,965 filed Sep. 17, 1999, abandoned; Ser. No. 09/430,656 filed Oct. 29, 1999, allowed; Ser. No. 09/513,783 filed Feb. 24, 2000, now U.S. Pat. No. 6,416,959; Ser No. 09/569,508 filed May 12, 2000, abandoned; Ser. No. 09/632,552 filed Aug. 4, 2000, abandoned; Ser. No. 09/632,544 filed Aug. 4, 2000, abandoned; Ser. No. 09/650,537 filed Aug. 29, 2000, now U.S. Pat. No. 6,573,039; and Ser. No. 09/676,217 filed Sep. 29, 2000, abandoned.

FIELD OF THE INVENTION

This invention is in the field of fluorescence-based cell and molecular biochemical assays for drug discovery.

BACKGROUND OF THE INVENTION

Drug discovery, as currently practiced in the art, is a long, multiple step process involving identification of specific disease targets, development of an assay based on a specific target, validation of the assay, optimization and automation of the assay to produce a screen, high throughput screening of compound libraries using the assay to identify "hits", hit validation and hit compound optimization. The output of this process is a lead compound that goes into pre-clinical and, if validated, eventually into clinical trials. In this process, the screening phase is distinct from the assay development phases, and involves testing compound efficacy in living biological systems.

Historically, drug discovery is a slow and costly process, spanning numerous years and consuming hundreds of millions of dollars per drug created. Developments in the areas of genomics and high throughput screening have resulted in increased capacity and efficiency in the areas of target identification and volume of compounds screened. Significant advances in automated DNA sequencing, PCR application, positional cloning, hybridization arrays, and bioinformatics have greatly increased the number of genes (and gene fragments) encoding potential drug screening targets. However, the basic scheme for drug screening remians the same.

Validation of genomic targets as points for therapeutic intervention using the existing methods and protocols has become a bottleneck in the drug discovery process due to the slow, manual methods employed, such as in vivo functional models, functional analysis of recombinant proteins, and stable cell line expression of candidate genes. Primary DNA sequence data acquired through automated sequencing does not permit identification of gene function, but can provide information about common "motifs" and specific gene homology when compared to known sequence databases. Genomic methods such as subtraction hybridization and RADE (rapid amplification of differential expression) can be used to identify genes that are up or down regulated in a disease state model. However, identification and validation still proceed down the same pathway. Some proteomic methods use protein identification (global expression arrays, 2D electrophoresis, combinatorial libraries) in combination with reverse genetics to identify candidate genes of interest. Such putative "disease associated sequences" or DAS isolated as intact cDNA are a great advantage to these methods, but they are identified by the hundreds without providing any information regarding type, activity, and distribution of the encoded protein. Choosing a subset of DAS as drug screening targets is "random", and thus extremely inefficient, without functional data to provide a mechanistic link with disease. It is necessary, therefore, to provide new technologies to rapidly screen DAS to establish biological function, thereby improving target validation and candidate optimization in drug discovery.

There are three major avenues for improving early drug discovery productivity. First, there is a need for tools that provide increased information handling capability. Bioinformatics has blossomed with the rapid development of DNA sequencing systems and the evolution of the genomics database. Genomics is beginning to play a critical role in the identification of potential new targets. Proteomics has become indispensible in relating structure and function of protein targets in order to predict drug interactions. However, the next level of biological complexity is the cell. Therefore, there is a need to acquire, manage and search multi-dimensional information from cells. Secondly, there is a need for higher throughput tools. Automation is a key to improving productivity as has already been demonstrated in DNA sequencing and high throughput primary screening. The instant invention provides for automated systems that extract multiple parameter information from cells that meet the need for higher throughput tools. The instant invention also provides for miniaturizing the methods, thereby allowing increased throughput, while decreasing the volumes of reagents and test compounds required in each assay.

Radioactivity has been the dominant read-out in early drug discovery assays. However, the need for more information, higher throughput and miniaturization has caused a shift towards using fluorescence detection. Fluorescence-based reagents can yield more powerful, multiple parameter assays that are higher in throughput and information content and require lower volumes of reagents and test compounds. Fluorescence is also safer and less expensive than radioactivity-based methods.

Screening of cells treated with dyes and fluorescent reagents is well known in the art. There is a considerable body of literature related to genetic engineering of cells to produce fluorescent proteins, such as modified green fluorescent protein (GFP), as a reporter molecule. Some properties of wild-type GFP are disclosed by Morise et al. (*Biochemistry* 13 (1974), p. 2656–2662), and Ward et al. (*Photochem. Photobiol.* 31 (1980), p. 611–615). The GFP of the jellyfish *Aequorea victoria* has an excitation maximum at 395 nm and an emission maximum at 510 nm, and does not require an exogenous factor for fluorescence activity. Uses for GFP disclosed in the literature are widespread and include the study of gene expression and protein localization (Chalfie et al., *Science* 263 (1994), p. 12501–12504)), as a tool for visualizing subcellular organelles (Rizzuto et al., *Curr. Biology* 5 (1995), p. 635–642)), visualization of protein transport along the secretory pathway (Kaether and Gerdes, *FEBS Letters* 369 (1995), p. 267–271)), expression in plant cells (Hu and Cheng, *FEBS Letters* 369 (1995), p. 331–334)) and Drosophila embryos (Davis et al., *Dev. Biology* 170 (1995), p. 726–729)), and as a reporter molecule fused to another protein of interest (U.S. Pat. No. 5,491,084). Similarly, WO 96/23898 relates to methods of detecting biologically active substances affecting intracellular processes by utilizing a GFP construct having a protein kinase activation site. This patent, and all other patents referenced in this application are incorporated by reference in their entirety.

Numerous references are related to GFP proteins in biological systems. For example, WO 96/09598 describes a system for isolating cells of interest utilizing the expression of a GFP like protein. WO 96/27675 describes the expression of GFP in plants. WO 95/21191 describes modified GFP protein expressed in transformed organisms to detect mutagenesis. U.S. Pat. Nos. 5,401,629 and 5,436,128 describe assays and compositions for detecting and evaluating the intracellular transduction of an extracellular signal using recombinant cells that express cell surface receptors and contain reporter gene constructs that include transcriptional regulatory elements that are responsive to the activity of cell surface receptors.

Performing a screen on many thousands of compounds requires parallel handling and processing of many compounds and assay component reagents. Standard high throughput screens ("HTS") use mixtures of compounds and biological reagents along with some indicator compound loaded into arrays of wells in standard microtiter plates with 96 or 384 wells. The signal measured from each well, either fluorescence emission, optical density, or radioactivity, integrates the signal from all the material in the well giving an overall population average of all the molecules in the well.

Science Applications International Corporation (SAIC) 130 Fifth Avenue, Seattle, Wash. 98109) describes an imaging plate reader. This system uses a CCD camera to image the whole area of a 96 well plate. The image is analyzed to calculate the total fluorescence per well for all the material in the well.

Molecular Devices, Inc. (Sunnyvale, Calif.) describes a system (FLIPR) which uses low angle laser scanning illumination and a mask to selectively excite fluorescence within approximately 200 microns of the bottoms of the wells in standard 96 well plates in order to reduce background when imaging cell monolayers. This system uses a CCD camera to image the whole area of the plate bottom. Although this system measures signals originating from a cell monolayer at the bottom of the well, the signal measured is averaged over the area of the well and is therefore still considered a measurement of the average response of a population of cells. The image is analyzed to calculate the total fluorescence per well for cell-based assays. Fluid delivery devices have also been incorporated into cell based screening systems, such as the FLIPR system, in order to initiate a response, which is then observed as a whole well population average response using a macro-imaging system.

In contrast to high throughput screens, various high-content screens ("HCS") have been developed to address the need for more detailed information about the temporal-spatial dynamics of cell constituents and processes. High-content screens automate the extraction of multicolor fluorescence information derived from specific fluorescence-based reagents incorporated into cells (Giuliano and Taylor (1995), *Curr. Op. Cell Biol.* 7:4; Giuliano et al. (1995) *Ann. Rev. Biophys. Biomol. Struct.* 24:405). Cells are analyzed using an optical system that can measure spatial, as well as temporal dynamics. (Farkas et al. (1993) *Ann. Rev. Physiol.* 55:785; Giuliano et al. (1990) In *Optical Microscopy for Biology*. B. Herman and K. Jacobson (eds.), pp. 543–557. Wiley-Liss, New York; Hahn et al (1992) *Nature* 359:736; Waggoner et al. (1996) *Hum. Pathol.* 27:494). The concept is to treat each cell as a "well" that has spatial and temporal information on the activities of the labeled constituents.

The types of biochemical and molecular information now accessible through fluorescence-based reagents applied to cells include ion concentrations, membrane potential, specific translocations, enzyme activities, gene expression, as well as the presence, amounts and patterns of metabolites, proteins, lipids, carbohydrates, and nucleic acid sequences (DeBiasio et al., (1996) *Mol. Biol. Cell.* 7:1259; Giuliano et al., (1995) *Ann. Rev. Biophys. Biomol. Struct.* 24:405; Heim and Tsien, (1996) *Curr. Biol.* 6:178).

High-content screens can be performed on either fixed cells, using fluorescently labeled antibodies, biological ligands, and/or nucleic acid hybridization probes, or live cells using multicolor fluorescent indicators and "biosensors." The choice of fixed or live cell screens depends on the specific cell-based assay required.

Fixed cell assays are the simplest, since an array of initially living cells in a microtiter plate format can be treated with various compounds and doses being tested, then the cells can be fixed, labeled with specific reagents, and measured. No environmental control of the cells is required after fixation. Spatial information is acquired, but only at one time point. The availability of thousands of antibodies, ligands and nucleic acid hybridization probes that can be applied to cells makes this an attractive approach for many types of cell-based screens. The fixation and labeling steps can be automated, allowing efficient processing of assays.

Live cell assays are more sophisticated and powerful, since an array of living cells containing the desired reagents can be screened over time, as well as space. Environmental control of the cells (temperature, humidity, and carbon dioxide) is required during measurement, since the physiological health of the cells must be maintained for multiple fluorescence measurements over time. There is a growing list of fluorescent physiological indicators and "biosensors" that can report changes in biochemical and molecular activities within cells (Giuliano et al., (1995) *Ann. Rev. Biophys. Biomol. Struct.* 24:405; Hahn et al., (1993) In *Fluorescent and Luminescent Probes for Biological Activity*. W. T. Mason, (ed.), pp. 349–359, Academic Press, San Diego).

The availability and use of fluorescence-based reagents has helped to advance the development of both fixed and live cell high-content screens. Advances in instrumentation to automatically extract multicolor, high-content information has recently made it possible to develop HCS into an automated tool. An article by Taylor, et al. (*American Scientist* 80 (1992), p. 322–335) describes many of these methods and their applications. For example, Proffitt et. al. (*Cytometry* 24: 204–213 (1996)) describe a semi-automated fluorescence digital imaging system for quantifying relative cell numbers in situ in a variety of tissue culture plate formats, especially 96-well microtiter plates. The system consists of an epifluorescence inverted microscope with a motorized stage, video camera, image intensifier, and a microcomputer with a PC-Vision digitizer. Turbo Pascal software controls the stage and scans the plate taking multiple images per well. The software calculates total fluorescence per well, provides for daily calibration, and configures easily for a variety of tissue culture plate formats. Thresholding of digital images and reagents which fluoresce only when taken up by living cells are used to reduce background fluorescence without removing excess fluorescent reagent.

Scanning confocal microscope imaging (Go et al., (1997) *Analytical Biochemistry* 247:210–215; Goldman et al., (1995) *Experimental Cell Research* 221:311–319) and multiphoton microscope imaging (Denk et al., (1990) *Science*

248:73; Gratton et al., (1994) *Proc. of the Microscopical Society of America*, pp. 154–155) are also well established methods for acquiring high resolution images of microscopic samples. The principle advantage of these optical systems is the very shallow depth of focus, which allows features of limited axial extent to be resolved against the background. For example, it is possible to resolve internal cytoplasmic features of adherent cells from the features on the cell surface. Because scanning multiphoton imaging requires very short duration pulsed laser systems to achieve the high photon flux required, fluorescence lifetimes can also be measured in these systems (Lakowicz et al., (1992) *Anal. Biochem.* 202:316–330; Gerrittsen et al. (1997), *J. of Fluorescence* 7:11–15)), providing additional capability for different detection modes. Small, reliable and relatively inexpensive laser systems, such as laser diode pumped lasers, are now available to allow multiphoton confocal microscopy to be applied in a fairly routine fashion.

A combination of the biological heterogeneity of cells in populations (Bright, et al., (1989). *J. Cell. Physiol.* 141:410; Giuliano, (1996) *Cell Motil. Cytoskel.* 35:237)) as well as the high spatial and temporal frequency of chemical and molecular information present within cells, makes it impossible to extract high-content information from populations of cells using existing whole microtiter plate readers. No existing high-content screening platform has been designed for multicolor, fluorescence-based screens using cells that are analyzed individually. Similarly, no method is currently available that combines automated fluid delivery to arrays of cells for the purpose of systematically screening compounds for the ability to induce a cellular response that is identified by HCS analysis, especially from cells grown in microtiter plates. Furthermore, no method exists in the art combining high throughput well-by-well measurements to identify "hits" in one assay followed by a second high content cell-by-cell measurement on the same plate of only those wells identified as hits.

The instant invention provides systems, methods, and screens that combine high throughput screening (HTS) and high content screening (HCS) that significantly improve target validation and candidate optimization by combining many cell screening formats with fluorescence-based molecular reagents and computer-based feature extraction, data analysis, and automation, resulting in increased quantity and speed of data collection, shortened cycle times, and, ultimately, faster evaluation of promising drug candidates. The instant invention also provides for miniaturizing the methods, thereby allowing increased throughput, while decreasing the volumes of reagents and test compounds required in each assay.

SUMMARY OF THE INVENTION

In one aspect, the present invention relates to a method for analyzing cells comprising
  providing cells containing fluorescent reporter molecules in an array of locations,
  treating the cells in the array of locations with one or more reagents,
  imaging numerous cells in each location with fluorescence optics,
  converting the optical information into digital data,
  utilizing the digital data to determine the distribution, environment or activity of the fluorescently labeled reporter molecules in the cells and the distribution of the cells, and
  interpreting that information in terms of a positive, negative or null effect of the compound being tested on the biological function In this embodiment, the method rapidly determines the distribution, environment, or activity of fluorescently labeled reporter molecules in cells for the purpose of screening large numbers of compounds for those that specifically affect particular biological functions. The array of locations may be a microtiter plate or a microchip which is a microplate having cells in an array of locations. In a preferred embodiment, the method includes computerized means for acquiring, processing, displaying and storing the data received. In a preferred embodiment, the method further comprises automated fluid delivery to the arrays of cells. In another preferred embodiment, the information obtained from high throughput measurements on the same plate are used to selectively perform high content screening on only a subset of the cell locations on the plate.

In another aspect of the present invention, a cell screening system is provided that comprises:
  a high magnification fluorescence optical system having a microscope objective,
  an XY stage adapted for holding a plate containing an array of cells and having a means for moving the plate for proper alignment and focusing on the cell arrays;
  a digital camera;
  a light source having optical means for directing excitation light to cell arrays and a means for directing fluorescent light emitted from the cells to the digital camera; and
  a computer means for receiving and processing digital data from the digital camera wherein the computer means includes a digital frame grabber for receiving the images from the camera, a display for user interaction and display of assay results, digital storage media for data storage and archiving, and a means for control, acquisition, processing and display of results.

In a preferred embodiment, the cell screening system further comprises a computer screen operatively associated with the computer for displaying data. In another preferred embodiment, the computer means for receiving and processing digital data from the digital camera stores the data in a bioinformatics data base. In a further preferred embodiment, the cell screening system further comprises a reader that measures a signal from many or all the wells in parallel. In another preferred embodiment, the cell screening system further comprises a mechanical-optical means for changing the magnification of the system, to allow changing modes between high throughput and high content screening. In another preferred embodiment, the cell screening system further comprises a chamber and control system to maintain the temperature, $CO_2$ concentration and humidity surrounding the plate at levels required to keep cells alive. In a further preferred embodiment, the cell screening system utilizes a confocal scanning illumination and detection system.

In another aspect of the present invention, a machine readable storage medium comprising a program containing a set of instructions for causing a cell screening system to execute procedures for defining the distribution and activity of specific cellular constituents and processes is provided. In a preferred embodiment, the cell screening system comprises a high magnification fluorescence optical system with a stage adapted for holding cells and a means for moving the stage, a digital camera, a light source for receiving and processing the digital data from the digital camera, and a computer means for receiving and processing the digital data from the digital camera. Preferred embodiments of the machine readable storage medium comprise programs consisting of a set of instructions for causing a cell screening system to execute the procedures set forth in FIGS. 9, 11, 12, 13, 14 or 15. Another preferred embodiment comprises a program consisting of a set of instructions for causing a cell screening system to execute procedures for detecting the distribution and activity of specific cellular constituents and processes. In most preferred embodiments, the cellular processes include, but are not limited to, nuclear translocation of a protein, cellular hypertrophy, apoptosis, and protease-induced translocation of a protein.

In another preferred embodiment, a variety of automated cell screening methods are provided, including screens to identify compounds that affect transcription factor activity, protein kinase activity, cell hypertrophy, cell spreading, microtubule structure, apoptosis, receptor internalization, and protease-induced translocation of a protein.

BRIEF DESCRIPTION OF THE DRAWINGS

FIGS. 25A–E is a flow chart of the preferred embodiments for analyzing cell spreading.

DETAILED DESCRIPTION OF THE INVENTION

Figure 1:
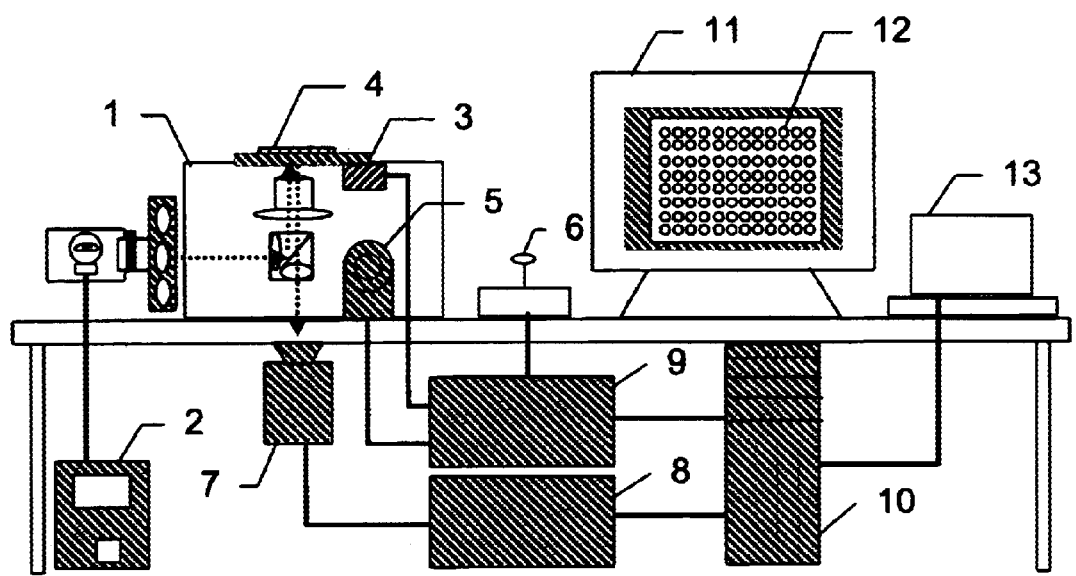
FIG. 1 shows a diagram of the components of the cell-based scanning system.

As used herein, the following terms have the specified meaning:

Markers of cellular domains. Luminescent probes that have high affinity for specific cellular constituents including specific organelles or molecules. These probes can either be small luminescent molecules or fluorescently tagged macromolecules used as "labeling reagents", "environmental indicators", or "biosensors."

Labeling reagents. Labeling reagents include, but are not limited to, luminescently labeled macromolecules including fluorescent protein analogs and biosensors, luminescent macromolecular chimeras including those formed with the green fluorescent protein and mutants thereof, luminescently labeled primary or secondary antibodies that react with cellular antigens involved in a physiological response, luminescent stains, dyes, and other small molecules.

Markers of cellular translocations. Luminescently tagged macromolecules or organelles that move from one cell domain to another during some cellular process or physiological response. Translocation markers can either simply report location relative to the markers of cellular domains or they can also be "biosensors" that report some biochemical or molecular activity as well.

Biosensors. Macromolecules consisting of a biological functional domain and a luminescent probe or probes that report the environmental changes that occur either internally or on their surface. A class of luminescently labeled macromolecules designed to sense and report these changes have been termed "fluorescent-protein biosensors". The protein component of the biosensor provides a highly evolved molecular recognition moiety. A fluorescent molecule attached to the protein component in the proximity of an active site transduces environmental changes into fluorescence signals that are detected using a system with an appropriate temporal and spatial resolution such as the cell scanning system of the present invention. Because the modulation of native protein activity within the living cell is reversible, and because fluorescent-protein biosensors can be designed to sense reversible changes in protein activity, these biosensors are essentially reusable.

Disease associated sequences ("DAS"). This term refers to nucleic acid sequences identified by standard techniques, such as primary DNA sequence data, genomic methods such as subtraction hybridization and RADE, and proteomic methods in combination with reverse genetics, as being of drug candidate compounds. The term does not mean that the sequence is only associated with a disease state.

High content screening (HCS) can be used to measure the effects of drugs on complex molecular events such as signal transduction pathways, as well as cell functions including, but not limited to, apoptosis, cell division, cell adhesion, locomotion, exocytosis, and cell-cell communication. Multicolor fluorescence permits multiple targets and cell processes to be assayed in a single screen. Cross-correlation of cellular responses will yield a wealth of information required for target validation and lead optimization.

In one aspect of the present invention, a cell screening system is provided comprising a high magnification fluorescence optical system having a microscope objective, an XY stage adapted for holding a plate with an array of locations for holding cells and having a means for moving the plate to align the locations with the microscope objective and a means for moving the plate in the direction to effect focusing; a digital camera; a light source having optical means for directing excitation light to cells in the array of locations and a means for directing fluorescent light emitted from the cells to the digital camera; and a computer means for receiving and processing digital data from the digital camera wherein the computer means includes: a digital frame grabber for receiving the images from the camera, a display for user interaction and display of assay results, digital storage media for data storage and archiving, and means for control, acquisition, processing and display of results.

FIG. 1 is a schematic diagram of a preferred embodiment of the cell scanning system. An inverted fluorescence microscope is used 1, such as a Zeiss Axiovert inverted fluorescence microscope which uses standard objectives with magnification of 1–100× to the camera, and a white light source (e.g. 100W mercury-arc lamp or 75W xenon lamp) with power supply 2. There is an XY stage 3 to move the plate 4 in the XY direction over the microscope objective. A Z-axis focus drive 5 moves the objective in the Z direction for focusing. A joystick 6 provides for manual movement of the stage in the XYZ direction. A high resolution digital camera 7 acquires images from each well or location on the plate. There is a camera power supply 8, an automation controller 9 and a central processing unit 10. The PC 11 provides a display 12 and has associated software. The printer 13 provides for printing of a hard copy record.

Figure 2:
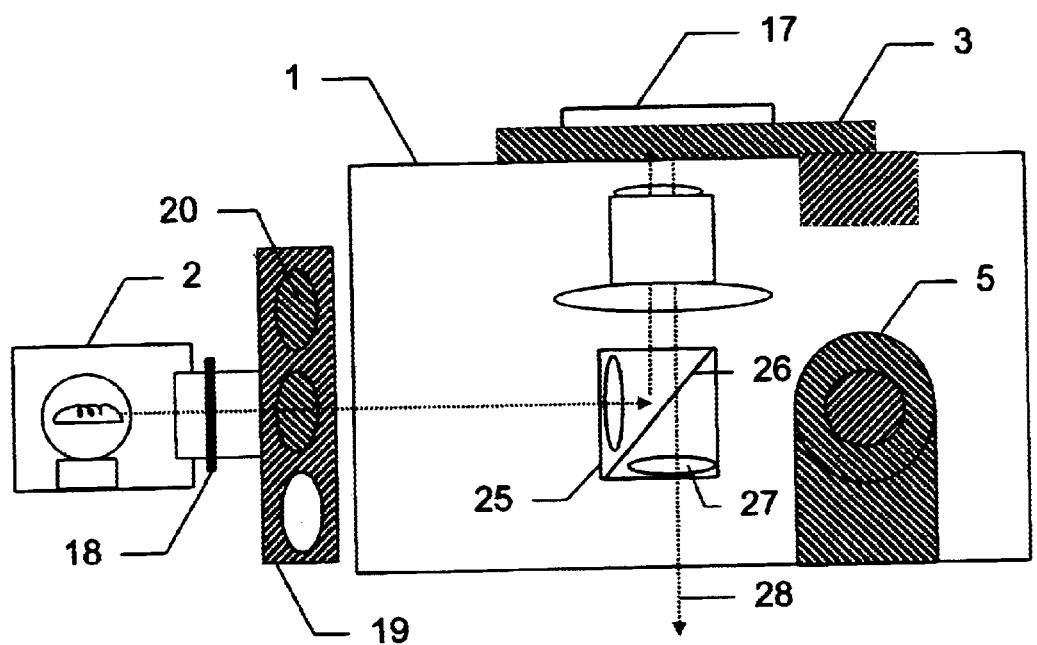
FIG. 2 shows a schematic of the microscope subassembly.
Figure 2:
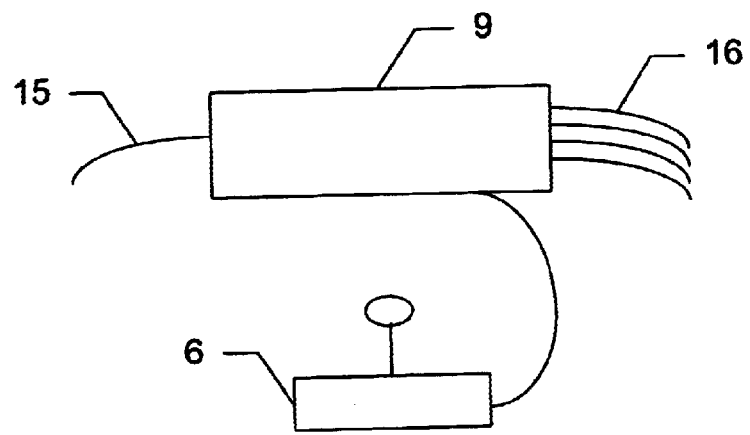

FIG. 2 is a schematic of one embodiment of the microscope assembly 1 of the invention, showing in more detail the XY stage 3, Z-axis focus drive 5, joystick 6, light source 2, and automation controller 9. Cables to the computer 15 and microscope 16, respectively, are provided. In addition, FIG. 2 shows a 96 well microtiter plate 17 which is moved on the XY stage 3 in the XY direction. Light from the light source 2 passes through the PC controlled shutter 18 to a motorized filter wheel 19 with excitation filters 20. The light passes into filter cube 25 which has a dichroic mirror 26 and an emission filter 27. Excitation light reflects off the dichroic mirror to the wells in the microtiter plate 17 and fluorescent light 28 passes through the dichroic mirror 26 and the emission filter 27 and to the digital camera 7.

Figure 3:
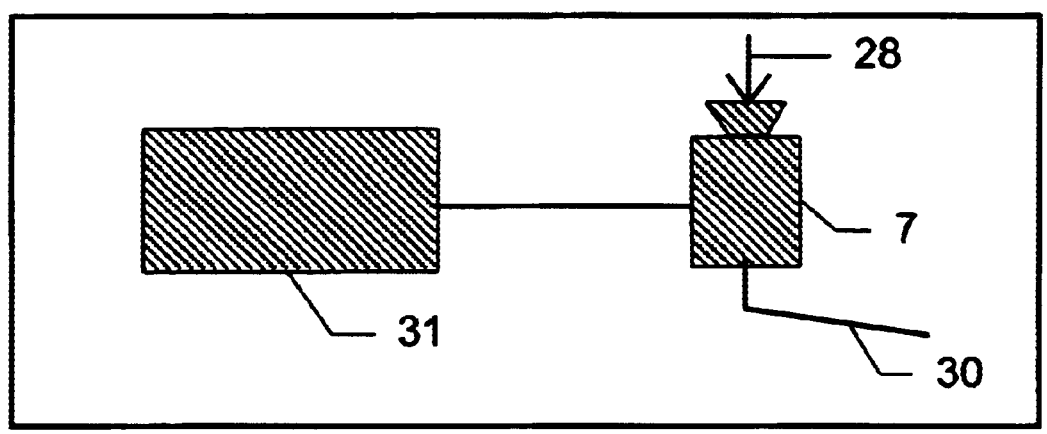
FIG. 3 shows the camera subassembly.

FIG. 3 shows a schematic drawing of a preferred camera assembly. The digital camera 7, which contains an automatic shutter for exposure control and a power supply 31, receives fluorescent light 28 from the microscope assembly. A digital cable 30 transports digital signals to the computer.

The standard optical configurations described above use microscope optics to directly produce an enlarged image of the specimen on the camera sensor in order to capture a high resolution image of the specimen. This optical system is commonly referred to as 'wide field' microscopy. Those skilled in the art of microscopy will recognize that a high resolution image of the specimen can be created by a variety of other optical systems, including, but not limited to, standard scanning confocal detection of a focused point or line of illumination scanned over the specimen (Go et al. 1997, supra), and multi-photon scanning confocal microscopy (Denk et al., 1990, supra), both of which can form images on a CCD detector or by synchronous digitization of the analog output of a photomultiplier tube.

In screening applications, it is often necessary to use a particular cell line, or primary cell culture, to take advantage of particular features of those cells. Those skilled in the art of cell culture will recognize that some cell lines are contact inhibited, meaning that they will stop growing when they become surrounded by other cells, while other cell lines will continue to grow under those conditions and the cells will literally pile up, forming many layers. An example of such a cell line is the HEK 293 (ATCC CRL-1573) line. An optical system that can acquire images of single cell layers in multilayer preparations is required for use with cell lines that tend to form layers. The large depth of field of wide field microscopes produces an image that is a projection through the many layers of cells, making analysis of subcellular spatial distributions extremely difficult in layer-forming cells. Alternatively, the very shallow depth of field that can be achieved on a confocal microscope, (about one micron), allows discrimination of a single cell layer at high resolution, simplifying the determination of the subcellular spatial distribution. Similarly, confocal imaging is preferable when detection modes such as fluorescence lifetime imaging are required.

The output of a standard confocal imaging attachment for a microscope is a digital image that can be converted to the same format as the images produced by the other cell screening system embodiments described above, and can therefore be processed in exactly the same way as those images. The overall control, acquisition and analysis in this embodiment is essentially the same. The optical configuration of the confocal microscope system, is essentially the same as that described above, except for the illuminator and detectors. Illumination and detection systems required for confocal microscopy have been designed as accessories to be attached to standard microscope optical systems such as that of the present invention (Zeiss, Germany). These alternative optical systems therefore can be easily integrated into the system as described above.

Figure 4:
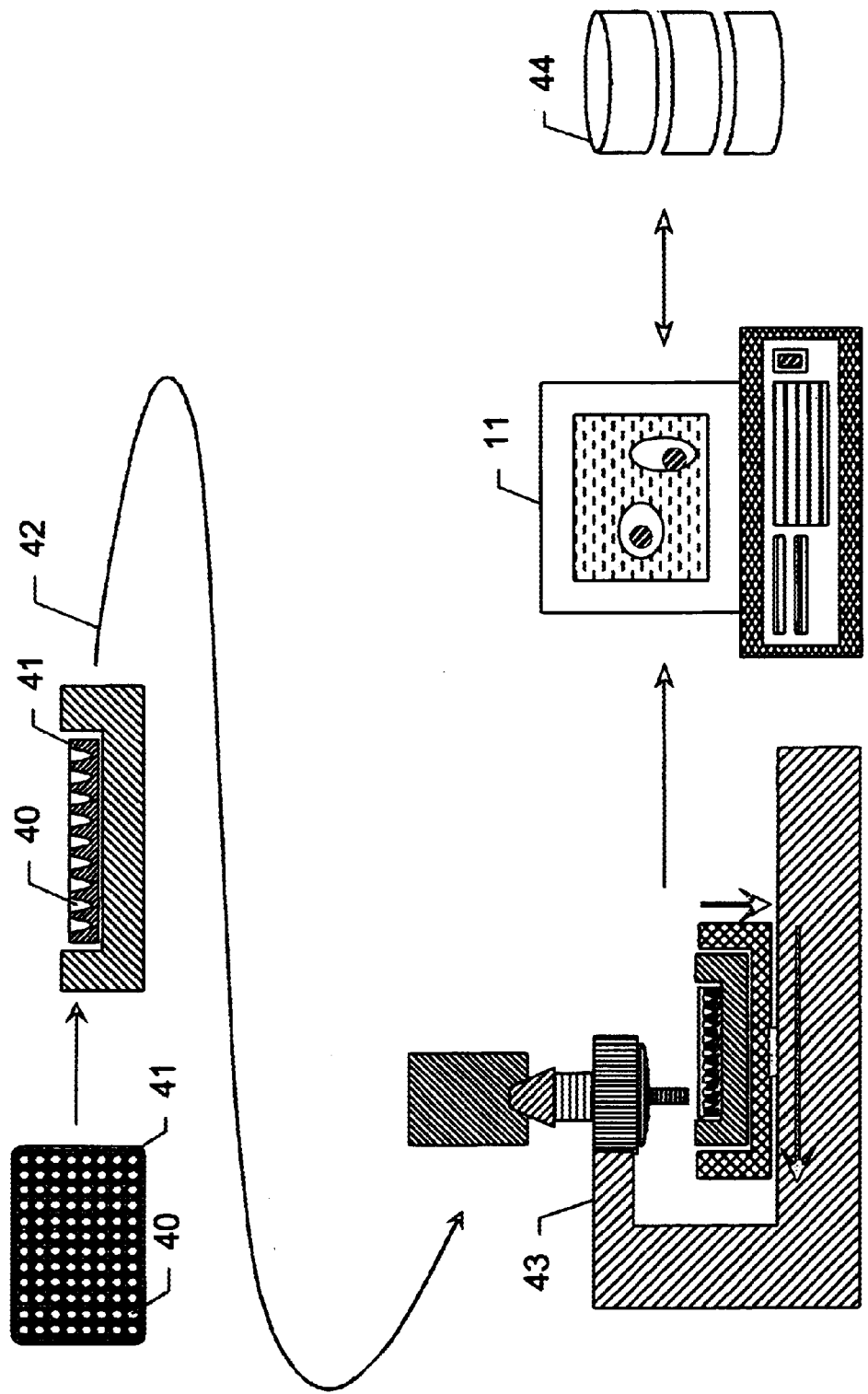
FIG. 4 illustrates cell scanning system process.

FIG. 4 illustrates an alternative embodiment of the invention in which cell arrays are in microwells 40 on a microplate 41, described ion co-pending U.S. application Ser. No. 08/865,341, incorporated by reference herein in its entirety. Typically the microplate is 20 mm by 30 mm as compared to a standard 96 well microtiter plate which is 86 mm by 129 mm. The higher density array of cells on a microplate allows the microplate to be imaged at a low resolution of a few microns per pixel for high throughput and particular locations on the microplate to be imaged at a higher resolution of less than 0.5 microns per pixel. These two resolution modes help to improve the overall throughput of the system.

Figure 5:
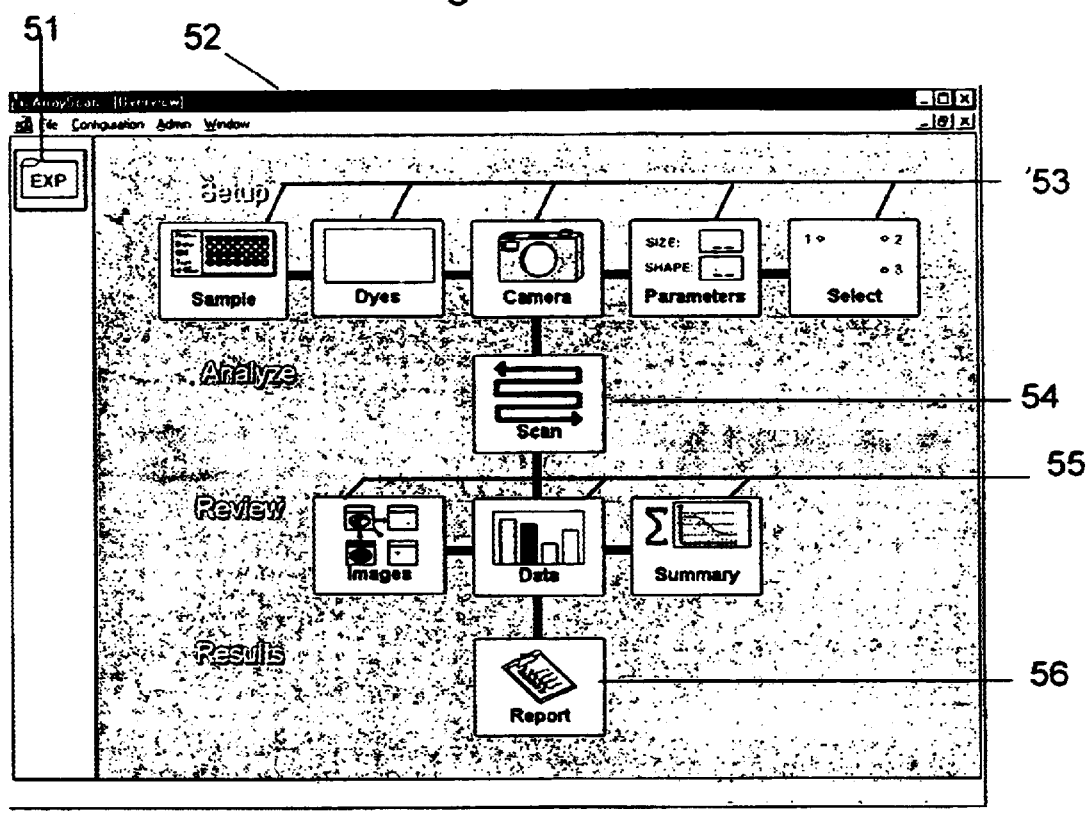
FIG. 5 illustrates a user interface showing major functions to guide the user.

The microplate chamber 42 serves as a microfluidic delivery system for the addition of compounds to cells. The microplate 41 in the microplate chamber 42 is placed in an XY microplate reader 43. Digital data is processed as described above. The small size of this microplate system increases throughput, minimizes reagent volume and allows control of the distribution and placement of cells for fast and precise cell-based analysis. Processed data can be displayed on a PC screen 11 and made part of a bioinformatics data base 44. This data base not only permits storage and retrieval of data obtained through the methods of this invention, but also permits acquisition and storage of external data relating to cells. FIG. 5 is a PC display which illustrates the operation of the software.

In an alternative embodiment, a high throughput system (HTS) is directly coupled with the HCS either on the same platform or on two separate platforms connected electronically (e.g. via a local area network). This embodiment of the invention, referred to as a dual mode optical system, has the advantage of increasing the throughput of a HCS by coupling it with a HTS and thereby requiring slower high resolution data acquisition and analysis only on the small subset of wells that show a response in the coupled HTS.

High throughput 'whole plate' reader systems are well known in the art and are commonly used as a component of an HTS system used to screen large numbers of compounds (Beggs (1997), *J. of Biomolec. Screening* 2:71–78; Macaffrey et al., (1996) *J. Biomolec. Screening* 1:187–190).

Figure 6:
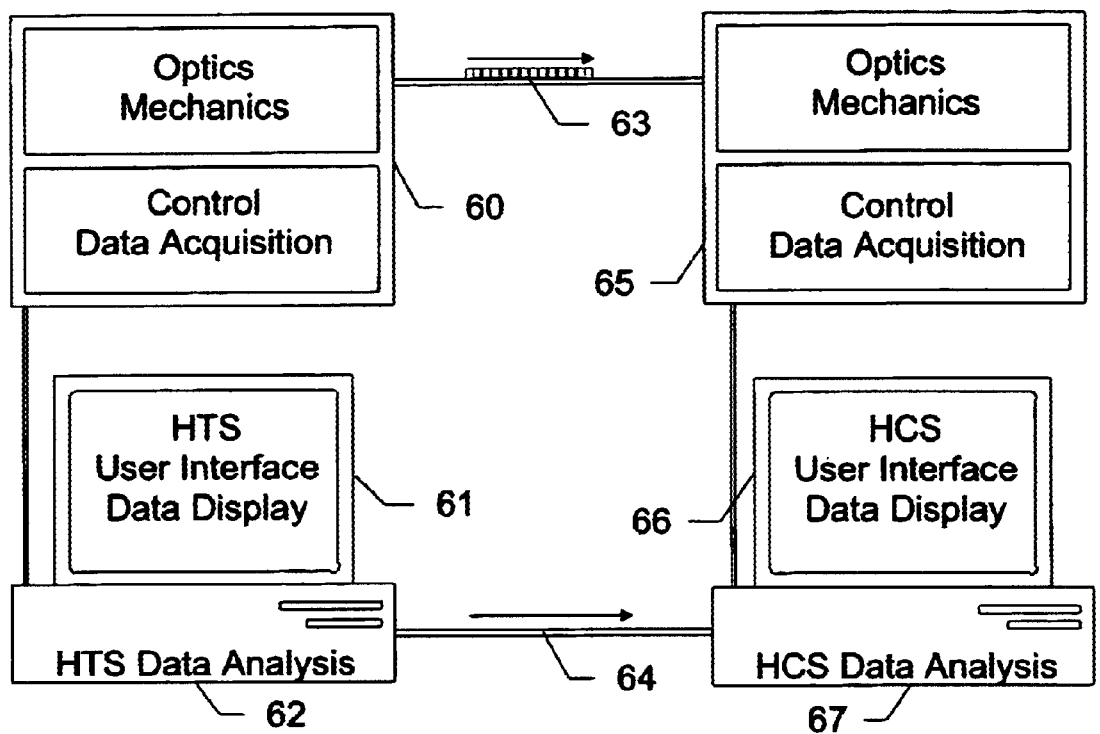
FIG. 6 is a block diagram of the two platform architecture of the Dual Mode System for Cell Based Screening in which one platform uses a telescope lens to read all wells of a microtiter plate and a second platform that uses a higher magnification lens to read individual cells in a well.

In one embodiment of dual mode cell based screening, a two platform architecture in which high throughput acquisition occurs on one platform and high content acquisition occurs on a second platform is provided (FIG. 6). Processing occurs on each platform independently, with results passed over a network interface, or a single controller is used to process the data from both platforms.

As illustrated in FIG. 6, an exemplified two platform dual mode optical system consists of two light optical instruments, a high throughput platform 60 and a high content platform 65, which read fluorescent signals emitted from cells cultured in microtiter plates or microwell arrays on a microplate, and communicate with each other via an electronic connection 64. The high throughput platform 60 analyzes all the wells in the whole plate either in parallel or rapid serial fashion. Those skilled in the art of screening will recognize that there are a many such commercially available high throughput reader systems that could be integrated into a dual mode cell based screening system (Topcount (Packard Instruments, Meriden, Conn.); Spectramax, Lumiskan (Molecular Devices, Sunnyvale, Calif.); Fluoroscan (Labsystems, Beverly, Mass.)). The high content platform 65, as described above, scans from well to well and acquires and analyzes high resolution image data collected from individual cells within a well.

The HTS software, residing on the system's computer 62, controls the high throughput instrument, and results are displayed on the monitor 61. The HCS software, residing on it's computer system 67, controls the high content instrument hardware 65, optional devices (e.g. plate loader, environmental chamber, fluid dispenser), analyzes digital image data from the plate, displays results on the monitor 66 and manages data measured in an integrated database. The two systems can also share a single computer, in which case all data would be collected, processed and displayed on that computer, without the need for a local area network to transfer the data. Microtiter plates are transferred from the high throughput system to the high content system 63 either manually or by a robotic plate transfer device, as is well known in the art (Beggs (1997), supra; Mcaffrey (1996), supra).

Figure 7:
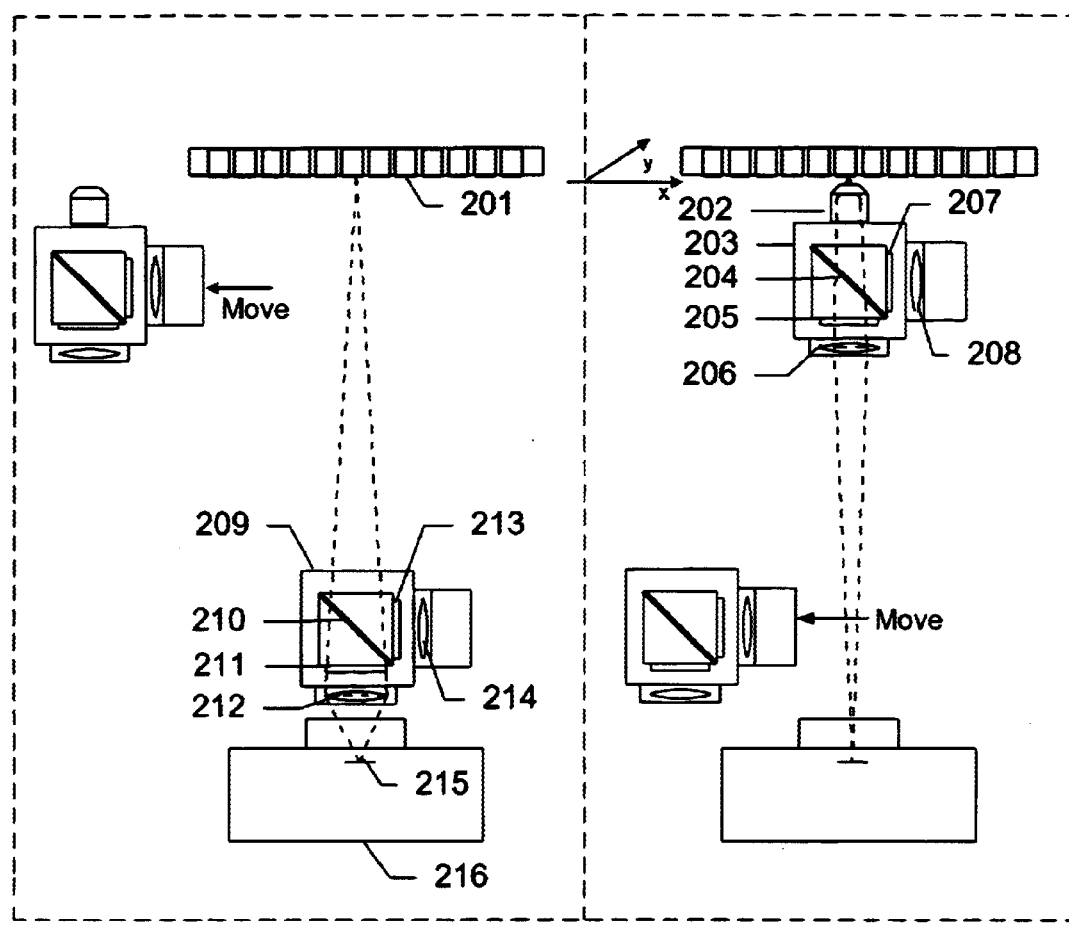
FIG. 7 is a detail of an optical system for a single platform architecture of the Dual Mode System for Cell Based Screening that uses a moveable 'telescope' lens to read all wells of a microtiter plate and a moveable higher magnification lens to read individual cells in a well.

In a preferred embodiment, the dual mode optical system utilizes a single platform system (FIG. 7). It consists of two separate optical modules, an HCS module 203 and an HTS module 209 that can be independently or collectively moved so that only one at a time is used to collect data from the microtiter plate 201. The microtiter plate 201 is mounted in a motorized X,Y stage so it can be positioned for imaging in either HTS or HCS mode. After collecting and analyzing the HTS image data as described below, the HTS optical module 209 is moved out of the optical path and the HCS optical module 203 is moved into place.

The optical module for HTS 209 consists of a projection lens 214, excitation wavelength filter 213 and dichroic mirror 210 which are used to illuminate the whole bottom of the plate with a specific wavelength band from a conventional microscope lamp system (not illustrated). The fluorescence emission is collected through the dichroic mirror 210 and emission wavelength filter 211 by a lens 212 which forms an image on the camera 216 with sensor 215.

The optical module for HCS 203 consists of a projection lens 208, excitation wavelength filter 207 and dichroic mirror 204 which are used to illuminate the back aperture of the microscope objective 202, and thereby the field of that objective, from a standard microscope illumination system (not shown). The fluorescence emission is collected by the microscope objective 202, passes through the dichroic mirror 204 and emission wavelength filter 205 and is focused by a tube lens 206 which forms an image on the same camera 216 with sensor 215.

Figure 8:
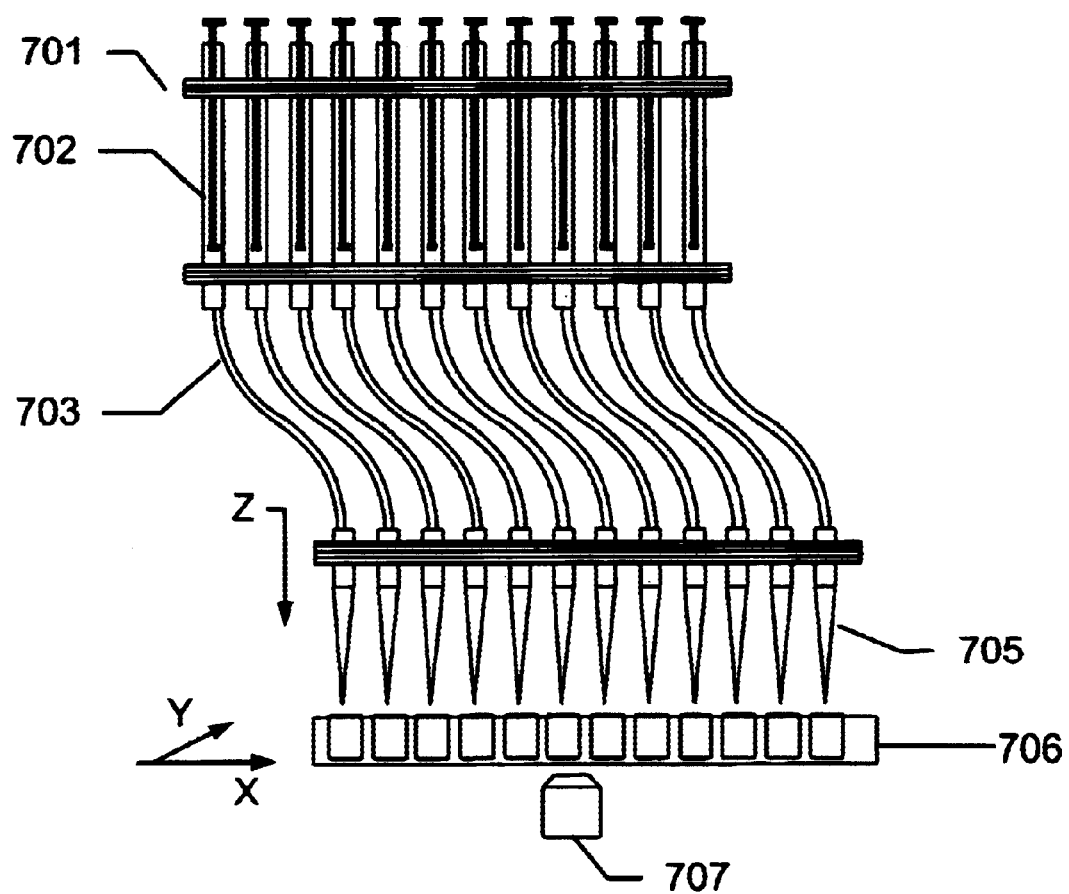
FIG. 8 is an illustration of the fluid delivery system for acquiring kinetic data on the Cell Based Screening System.

In an alternative embodiment of the present invention, the cell screening system further comprises a fluid delivery device for use with the live cell embodiment of the method of cell screening (see below). FIG. 8 exemplifies a fluid delivery device for use with the system of the invention. It consists of a bank of 12 syringe pumps 701 driven by a single motor drive. Each syringe 702 is sized according to the volume to be delivered to each well, typically between 1 and 100 $\mu$L. Each syringe is attached via flexible tubing 703 to a similar bank of connectors which accept standard pipette tips 705. The bank of pipette tips are attached to a drive system so they can be lowered and raised relative to the microtiter plate 706 to deliver fluid to each well. The plate is mounted on an X,Y stage, allowing movement relative to the optical system 707 for data collection purposes. This set-up allows one set of pipette tips, or even a single pipette tip, to deliver reagent to all the wells on the plate. The bank of syringe pumps can be used to deliver fluid to 12 wells simultaneously, or to fewer wells by removing some of the tips.

In another aspect, the present invention provides a method for analyzing cells comprising providing an array of locations which contain multiple cells wherein the cells contain one or more fluorescent reporter molecules; scanning multiple cells in each of the locations containing cells to obtain fluorescent signals from the fluorescent reporter molecule in the cells; converting the fluorescent signals into digital data; and utilizing the digital data to determine the distribution, environment or activity of the fluorescent reporter molecule within the cells.

Cell Arrays

Screening large numbers of compounds for activity with respect to a particular biological function requires preparing arrays of cells for parallel handling of cells and reagents. Standard 96 well microtiter plates which are 86 mm by 129 mm, with 6 mm diameter wells on a 9 mm pitch, are used for compatibility with current automated loading and robotic handling systems. The microplate is typically 20 mm by 30 mm, with cell locations that are 100–200 microns in dimension on a pitch of about 500 microns. Methods for making microplates are described in U.S. patent application Ser. No.

08/865,341, incorporated by reference herein in its entirety. Microplates may consist of coplanar layers of materials to which cells adhere, patterned with materials to which cells will not adhere, or etched 3-dimensional surfaces of similarly pattered materials. For the purpose of the following discussion, the terms 'well' and 'microwell' refer to a location in an array of any construction to which cells adhere and within which the cells are imaged. Microplates may also include fluid delivery channels in the spaces between the wells. The smaller format of a microplate increases the overall efficiency of the system by minimizing the quantities of the reagents, storage and handling during preparation and the overall movement required for the scanning operation. In addition, the whole area of the microplate can be imaged more efficiently, allowing a second mode of operation for the microplate reader as described later in this document.

Fluorescence Reporter Molecules

A major component of the new drug discovery paradigm is a continually growing family of fluorescent and luminescent reagents that are used to measure the temporal and spatial distribution, content, and activity of intracellular ions, metabolites, macromolecules, and organelles. Classes of these reagents include labeling reagents that measure the distribution and amount of molecules in living and fixed cells, environmental indicators to report signal transduction events in time and space, and fluorescent protein biosensors to measure target molecular activities within living cells. A multiparameter approach that combines several reagents in a single cell is a powerful new tool for drug discovery.

The method of the present invention is based on the high affinity of fluorescent or luminescent molecules for specific cellular components. The affinity for specific components is governed by physical forces such as ionic interactions, covalent bonding (which includes chimeric fusion with protein-based chromophores, fluorophores, and lumiphores), as well as hydrophobic interactions, electrical potential, and, in some cases, simple entrapment within a cellular component. The luminescent probes can be small molecules, labeled macromolecules, or genetically engineered proteins, including, but not limited to green fluorescent protein chimeras.

Those skilled in this art will recognize a wide variety of fluorescent reporter molecules that can be used in the present invention, including, but not limited to, fluorescently labeled biomolecules such as proteins, phospholipids and DNA hybridizing probes. Similarly, fluorescent reagents specifically synthesized with particular chemical properties of binding or association have been used as fluorescent reporter molecules (Barak et al., (1997), *J. Biol. Chem.* 272:27497–27500; Southwick et al., (1990), *Cytometry* 11:418–430; Tsien (1989) in *Methods in Cell Biology*, Vol. 29 Taylor and Wang (eds.), pp. 127–156). Fluorescently labeled antibodies are particularly useful reporter molecules due to their high degree of specificity for attaching to a single molecular target in a mixture of molecules as complex as a cell or tissue.

The luminescent probes can be synthesized within the living cell or can be transported into the cell via several non-mechanical modes including diffusion, facilitated or active transport, signal-sequence-mediated transport, and endocytotic or pinocytotic uptake. Mechanical bulk loading methods, which are well known in the art, can also be used to load luminescent probes into living cells (Barber et al. (1996), *Neuroscience Letters* 207:17–20; Bright et al. (1996), *Cytometry* 24:226–233; McNeil (1989) in *Methods in Cell Biology*, Vol. 29, Taylor and Wang (eds.), pp. 153–173). These methods include electroporation and other mechanical methods such as scrape-loading, bead-loading, impact-loading, syringe-loading, hypertonic and hypotonic loading. Additionally, cells can be genetically engineered to express reporter molecules, such as GFP, coupled to a protein of interest as previously described (Chalfie and Prasher U.S. Pat. No. 5,491,084; Cubitt et al. (1995), *Trends in Biochemical Science* 20:448–455).

Once in the cell, the luminescent probes accumulate at their target domain as a result of specific and high affinity interactions with the target domain or other modes of molecular targeting such as signal-sequence-mediated transport. Fluorescently labeled reporter molecules are useful for determining the location, amount and chemical environment of the reporter. For example, whether the reporter is in a lipophilic membrane environment or in a more aqueous environment can be determined (Giuliano et al. (1995), *Ann. Rev. of Biophysics and Biomolecular Structure* 24:405–434; Giuliano and Taylor (1995), *Methods in Neuroscience* 27:1–16). The pH environment of the reporter can be determined (Bright et al. (1989), *J. Cell Biology* 104:1019–1033; Giuliano et al. (1987), *Anal. Biochem.* 167:362–371; Thomas et al. (1979), *Biochemistry* 18:2210–2218). It can be determined whether a reporter having a chelating group is bound to an ion, such as Ca++, or not (Bright et al. (1989), In *Methods in Cell Biology*, Vol. 30, Taylor and Wang (eds.), pp. 157–192; Shimoura et al. (1988), *J. of Biochemistry* (Tokyo) 251:405–410; Tsien (1989) In *Methods in Cell Biology*, Vol. 30, Taylor and Wang (eds.), pp. 127–156).

Furthermore, certain cell types within an organism may contain components that can be specifically labeled that may not occur in other cell types. For example, epithelial cells often contain polarized membrane components. That is, these cells asymmetrically distribute macromolecules along their plasma membrane. Connective or supporting tissue cells often contain granules in which are trapped molecules specific to that cell type (e.g., heparin, histamine, serotonin, etc.). Most muscular tissue cells contain a sarcoplasmic reticulum, a specialized organelle whose function is to regulate the concentration of calcium ions within the cell cytoplasm. Many nervous tissue cells contain secretory granules and vesicles in which are trapped neurohormones or neurotransmitters. Therefore, fluorescent molecules can be designed to label not only specific components within specific cells, but also specific cells within a population of mixed cell types.

Those skilled in the art will recognize a wide variety of ways to measure fluorescence. For example, some fluorescent reporter molecules exhibit a change in excitation or emission spectra, some exhibit resonance energy transfer where one fluorescent reporter loses fluorescence, while a second gains in fluorescence, some exhibit a loss (quenching) or appearance of fluorescence, while some report rotational movements (Giuliano et al. (1995), *Ann. Rev. of Biophysics and Biomol. Structure* 24:405–434; Giuliano et al. (1995), *Methods in Neuroscience* 27:1–16).

Scanning Cell Arrays

Figure 9:
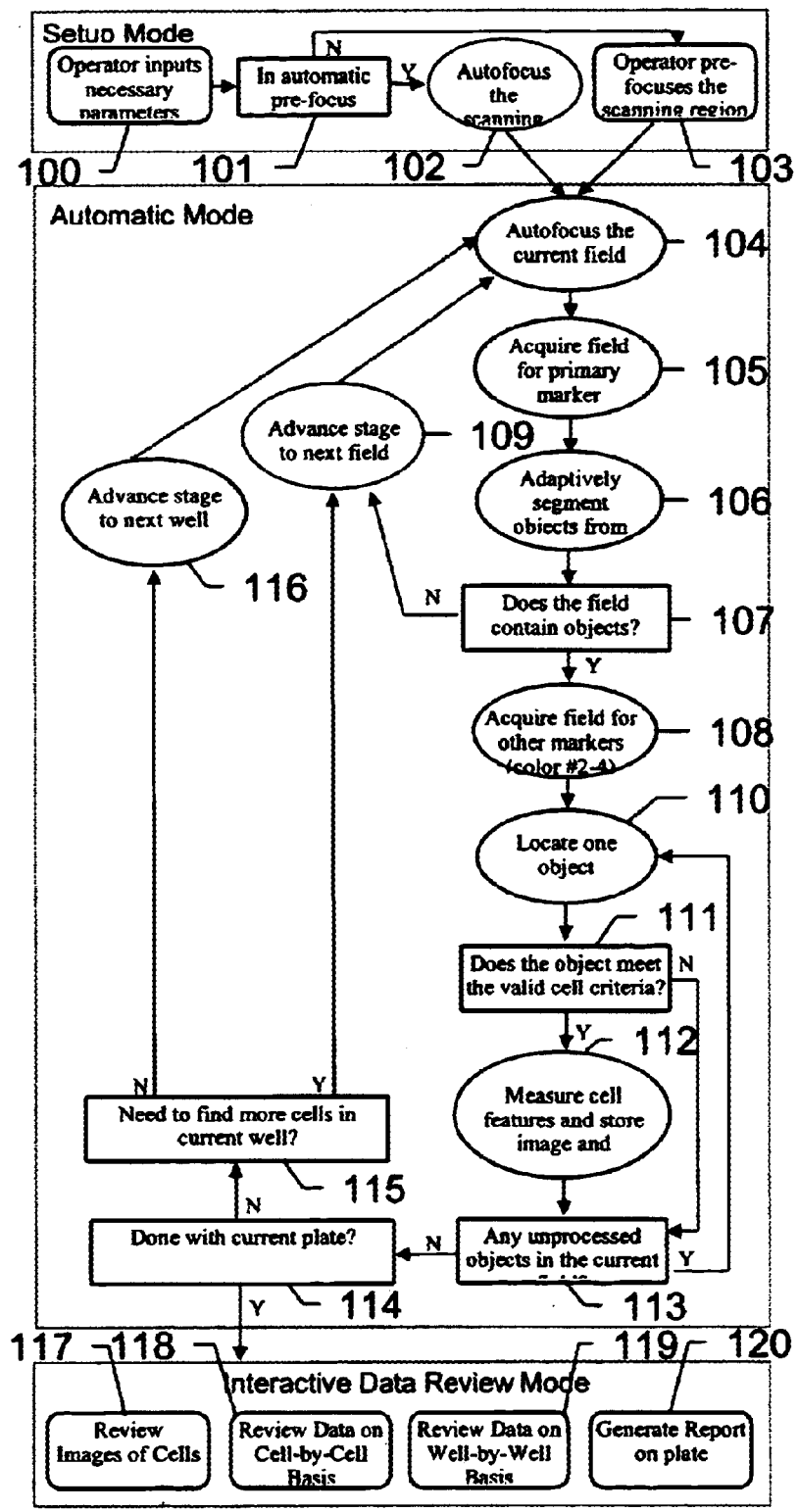
FIG. 9 is a flow chart of processing step for the cell-based scanning system.
Figure 9:
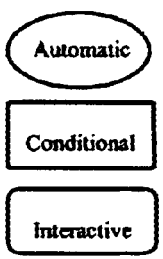

Referring to FIG. 9, a preferred embodiment is provided to analyze cells that comprises operator-directed parameters being selected based on the assay being conducted, data acquisition by the cell screening system on the distribution of fluorescent signals within a sample, and interactive data review and analysis. At the start of an automated scan the operator enters information 100 that describes the sample, specifies the filter settings and fluorescent channels to match the biological labels being used and the information sought, and then adjusts the camera settings to match the sample brightness. For flexibility to handle a range of samples, the software allows selection of various parameter settings used to identify nuclei and cytoplasm, and selection of different fluorescent reagents, identification of cells of interest based on morphology or brightness, and cell numbers to be analyzed per well. These parameters are stored in the system's for easy retrieval for each automated run. The system's interactive cell identification mode simplifies the selection of morphological parameter limits such as the range of size, shape, and intensity of cells to be analyzed. The user specifies which wells of the plate the system will scan and how many fields or how many cells to analyze in each well. Depending on the setup mode selected by the user at step 101, the system either automatically pre-focuses the region of the plate to be scanned using an autofocus procedure to "find focus" of the plate 102 or the user interactively pre-focuses 103 the scanning region by selecting three "tag" points which define the rectangular area to be scanned. A least-squares fit "focal plane model" is then calculated from these tag points to estimate the focus of each well during an automated scan. The focus of each well is estimated by interpolating from the focal plane model during a scan.

During an automated scan, the software dynamically displays the scan status, including the number of cells analyzed, the current well being analyzed, images of each independent wavelength as they are acquired, and the result of the screen for each well as it is determined. The plate 4 (FIG. 1) is scanned in a serpentine style as the software automatically moves the motorized microscope XY stage 3 from well to well and field to field within each well of a 96-well plate. Those skilled in the programming art will recognize how to adapt software for scanning of other microplate formats such as 24, 48, and 384 well plates. The scan pattern of the entire plate as well as the scan pattern of fields within each well are programmed. The system adjusts sample focus with an autofocus procedure 104 (FIG. 9) through the Z axis focus drive 5, controls filter selection via a motorized filter wheel 19, and acquires and analyzes images of up to four different colors ("channels" or "wavelengths").

The autofocus procedure is called at a user selected frequency, typically for the first field in each well and then once every 4 to 5 fields within each well. The autofocus procedure calculates the starting Z-axis point by interpolating from the pre-calculated plane focal model. Starting a programmable distance above or below this set point, the procedure moves the mechanical Z-axis through a number of different positions, acquires an image at each position, and finds the maximum of a calculated focus score that estimates the contrast of each image. The Z position of the image with the maximum focus score determines the best focus for a particular field. Those skilled in the art will recognize this as a variant of automatic focusing methods as described in Harms et al. in *Cytometry* 5 (1984), 236–243, Groen et al. in *Cytometry* 6 (1985), 81–91, and Firestone et al. in *Cytometry* 12 (1991), 195–206.

For image acquisition, the camera's exposure time is separately adjusted for each dye to ensure a high-quality image from each channel. Software procedures can be called, at the user's option, to correct for registration shifts between wavelengths by accounting for linear (X and Y) shifts between wavelengths before making any further measurements. The electronic shutter 18 is controlled so that sample photo-bleaching is kept to a minimum. Background shading and uneven illumination can be corrected by the software using methods known in the art (Bright et al. (1987), *J. Cell Biol.* 104:1019–1033).

In one channel, images are acquired of a primary marker 105 (FIG. 9) (typically cell nuclei counterstained with DAPI or PI fluorescent dyes) which are segmented ("identified") using an adaptive thresholding procedure. The adaptive thresholding procedure 106 is used to dynamically select the threshold of an image for separating cells from the background. The staining of cells with fluorescent dyes can vary to an unknown degree across cells in a microtiter plate sample as well as within images of a field of cells within each well of a microtiter plate. This variation can occur as a result of sample preparation and/or the dynamic nature of cells. A global threshold is calculated for the complete image to separate the cells from background and account for field to field variation. These global adaptive techniques are variants of those described in the art. (Kittler et al. in *Computer Vision, Graphics, and Image Processing* 30 (1985), 125–147, Ridler et al. in *IEEE Trans. Systems, Man, and Cybernetics* (1978), 630–632.)

An alternative adaptive thresholding method utilizes local region thresholding in contrast to global image thresholding. Image analysis of local regions leads to better overall segmentation since staining of cell nuclei (as well as other labeled components) can vary across an image. Using this global/local procedure, a reduced resolution image (reduced in size by a factor of 2 to 4) is first globally segmented (using adaptive thresholding) to find regions of interest in the image. These regions then serve as guides to more fully analyze the same regions at full resolution. A more localized threshold is then calculated (again using adaptive thresholding) for each region of interest.

The output of the segmentation procedure is a binary image wherein the objects are white and the background is black. This binary image, also called a mask in the art, is used to determine if the field contains objects 107. The mask is labeled with a blob labeling method whereby each object (or blob) has a unique number assigned to it. Morphological features, such as area and shape, of the blobs are used to differentiate blobs likely to be cells from those that are considered artifacts. The user pre-sets the morphological selection criteria by either typing in known cell morphological features or by using the interactive training utility. If objects of interest are found in the field, images are acquired for all other active channels 108, otherwise the stage is advanced to the next field 109 in the current well. Each object of interest is located in the image for further analysis 110. The software determines if the object meets the criteria for a valid cell nucleus 111 by measuring its morphological features (size and shape). For each valid cell, the XYZ stage location is recorded, a small image of the cell is stored, and features are measured 112.

Figure 10:
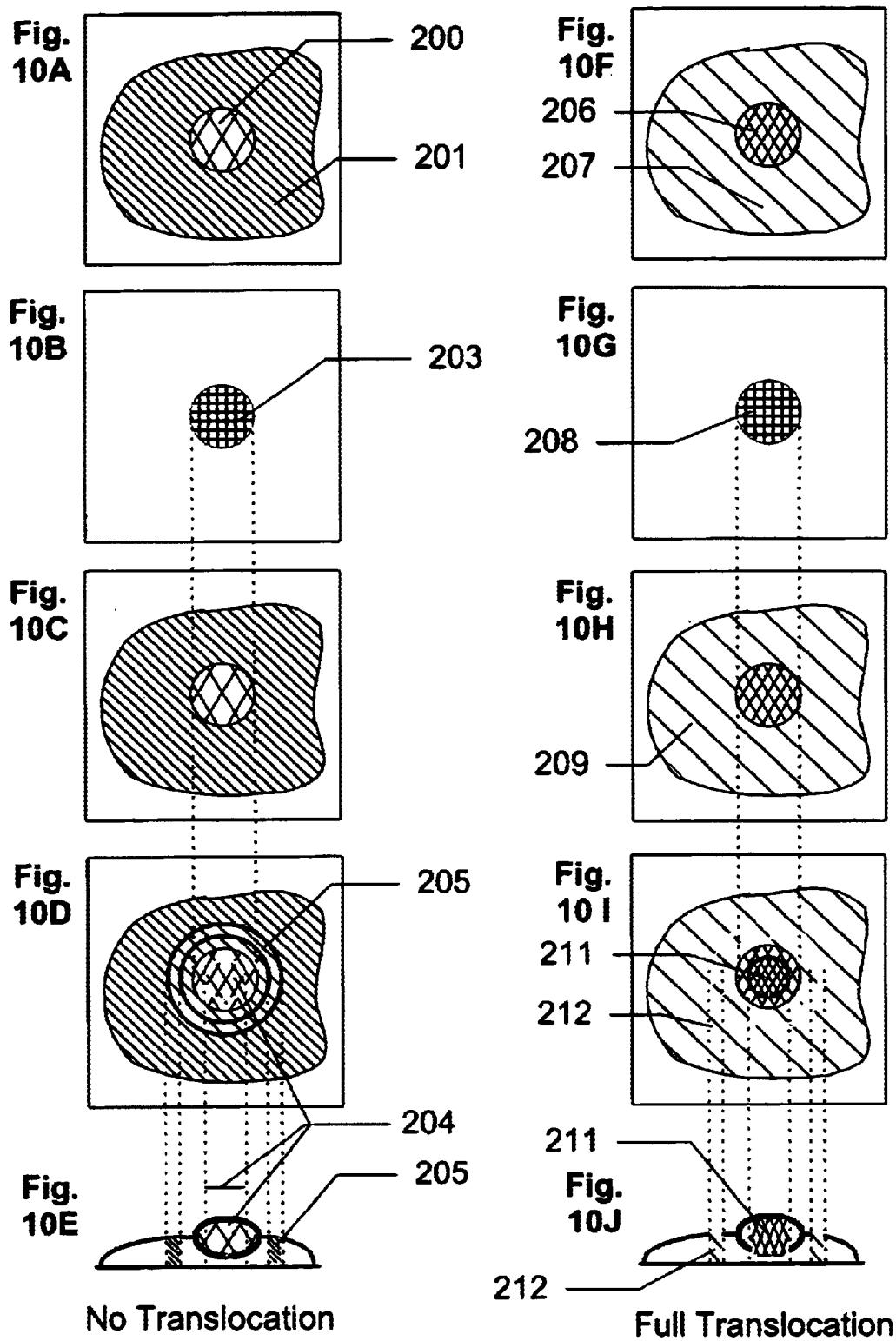
FIGS. 10A–J illustrates the strategy of the Nuclear Translocation Assay.

The cell scanning method of the present invention can be used to perform many different assays on cellular samples by applying a number of analytical methods simultaneously to measure features at multiple wavelengths. An example of one such assay provides for the following measurements:

1. The total fluorescent intensity within the cell nucleus for colors 1–4
2. The area of the cell nucleus for color 1 (the primary marker)
3. The shape of the cell nucleus for color 1 is described by three shape features:
    a) perimeter squared area
    b) box area ratio
    c) height width ratio 4. The average fluorescent intensity within the cell nucleus for colors 1–4 (i.e. #1 divided by #2)
5. The total fluorescent intensity of a ring outside the nucleus (see FIG. 10) that represents fluorescence of the cell's cytoplasm (cytoplasmic mask) for colors 2–4
6. The area of the cytoplasmic mask
7. The average fluorescent intensity of the cytoplasmic mask for colors 2–4 (i.e. #5 divided by #6)
8. The ratio of the average fluorescent intensity of the cytoplasmic mask to average fluorescent intensity within the cell nucleus for colors 2–4 (i.e. #7 divided by #4)
9. The difference of the average fluorescent intensity of the cytoplasmic mask and the average fluorescent intensity within the cell nucleus for colors 2–4 (i.e. #7 minus #4)
10. The number of fluorescent domains (also call spots, dots, or grains) within the cell nucleus for colors 2–4

Features 1 through 4 are general features of the different cell screening assays of the invention. These steps are commonly used in a variety of image analysis applications and are well known in art (Russ (1992) *The Image Processing Handbook*, CRC Press Inc.; Gonzales et al. (1987), *Digital Image Processing*. Addison-Wesley Publishing Co. pp. 391–448). Features 5–9 have been developed specifically to provide measurements of a cell's fluorescent molecules within the local cytoplasmic region of the cell and the translocation (i.e. movement) of fluorescent molecules from the cytoplasm to the nucleus. These features (steps 5–9) are used for analyzing cells in microplates for the inhibition of nuclear translocation. For example, inhibition of nuclear translocation of transcription factors provides a novel approach to screening intact cells (detailed examples of other types of screens will be provided below). A specific method measures the amount of probe in the nuclear region (feature 4) versus the local cytoplasmic region (feature 7) of each cell. Quantification of the difference between these two sub-cellular compartments provides a measure of cytoplasm-nuclear translocation (feature 9).

Feature 10 describes a screen used for counting of DNA or RNA probes within the nuclear region in colors 2–4. For example, probes are commercially available for identifying chromosome-specific DNA sequences (Life Technologies, Gaithersburg, Md; Genosys, Woodlands, Tex.; Biotechnologies, Inc., Richmond, Calif.; Bio 101, Inc., Vista, Calif.) Cells are three-dimensional in nature and when examined at a high magnification under a microscope one probe may be in-focus while another may be completely out-of-focus. The cell screening method of the present invention provides for detecting three-dimensional probes in nuclei by acquiring images from multiple focal planes. The software moves the Z-axis motor drive 5 (FIG. 1) in small steps where the step distance is user selected to account for a wide range of different nuclear diameters. At each of the focal steps, an image is acquired. The maximum gray-level intensity from each pixel in each image is found and stored in a resulting maximum projection image. The maximum projection image is then used to count the probes. The above method works well in counting probes that are not stacked directly above or below another one. To account for probes stacked on top of each other in the Z-direction, users can select an option to analyze probes in each of the focal planes acquired. In this mode, the scanning system performs the maximum plane projection method as discussed above, detects probe regions of interest in this image, then further analyzes these regions in all the focal plane images.

After measuring cell features 112 (FIG. 9), the system checks if there are any unprocessed objects in the current field 113. If there are any unprocessed objects, it locates the next object 110 and determines whether it meets the criteria for a valid cell nucleus 111, and measures its features. Once all the objects in the current field are processed, the system determines whether analysis of the current plate is complete 114; if not, it determines the need to find more cells in the current well 115. If the need exists, the system advances the XYZ stage to the next field within the current well 109 or advances the stage to the next well 116 of the plate.

After a plate scan is complete, images and data can be reviewed with the system's image review, data review, and summary review facilities. All images, data, and settings from a scan are archived in the system's database for later review or for interfacing with a network information management system. Data can also be exported to other third-party statistical packages to tabulate results and generate other reports. Users can review the images alone of every cell analyzed by the system with an interactive image review procedure 117. The user can review data on a cell-by-cell basis using a combination of interactive graphs, a data spreadsheet of measured features, and images of all the fluorescence channels of a cell of interest with the interactive cell-by-cell data review procedure 118. Graphical plotting capabilities are provided in which data can be analyzed via interactive graphs such as histograms and scatter plots. Users can review summary data that are accumulated and summarized for all cells within each well of a plate with an interactive well-by-well data review procedure 119. Hard copies of graphs and images can be printed on a wide range of standard printers.

As a final phase of a complete scan, reports can be generated on one or more statistics of the measured features. Users can generate a graphical report of data summarized on a well-by-well basis for the scanned region of the plate using an interactive report generation procedure 120. This report includes a summary of the statistics by well in tabular and graphical format and identification information on the sample. The report window allows the operator to enter comments about the scan for later retrieval. Multiple reports can be generated on many statistics and be printed with the touch of one button. Reports can be previewed for placement and data before being printed.

The above-recited embodiment of the method operates in a single high resolution mode referred to as the high content screening (HCS) mode. The HCS mode provides sufficient spatial resolution within a well (on the order of 1 $\mu$m) to define the distribution of material within the well, as well as within individual cells in the well. The high degree of information content accessible in that mode, comes at the expense of speed and complexity of the required signal processing.

In an alternative embodiment, a high throughput system (HTS) is directly coupled with the HCS either on the same platform or on two separate platforms connected electronically (e.g. via a local area network). This embodiment of the invention, referred to as a dual mode optical system, has the advantage of increasing the throughput of an HCS by coupling it with an HTS and thereby requiring slower high resolution data acquisition and analysis only on the small subset of wells that show a response in the coupled HTS.

Figure 11:
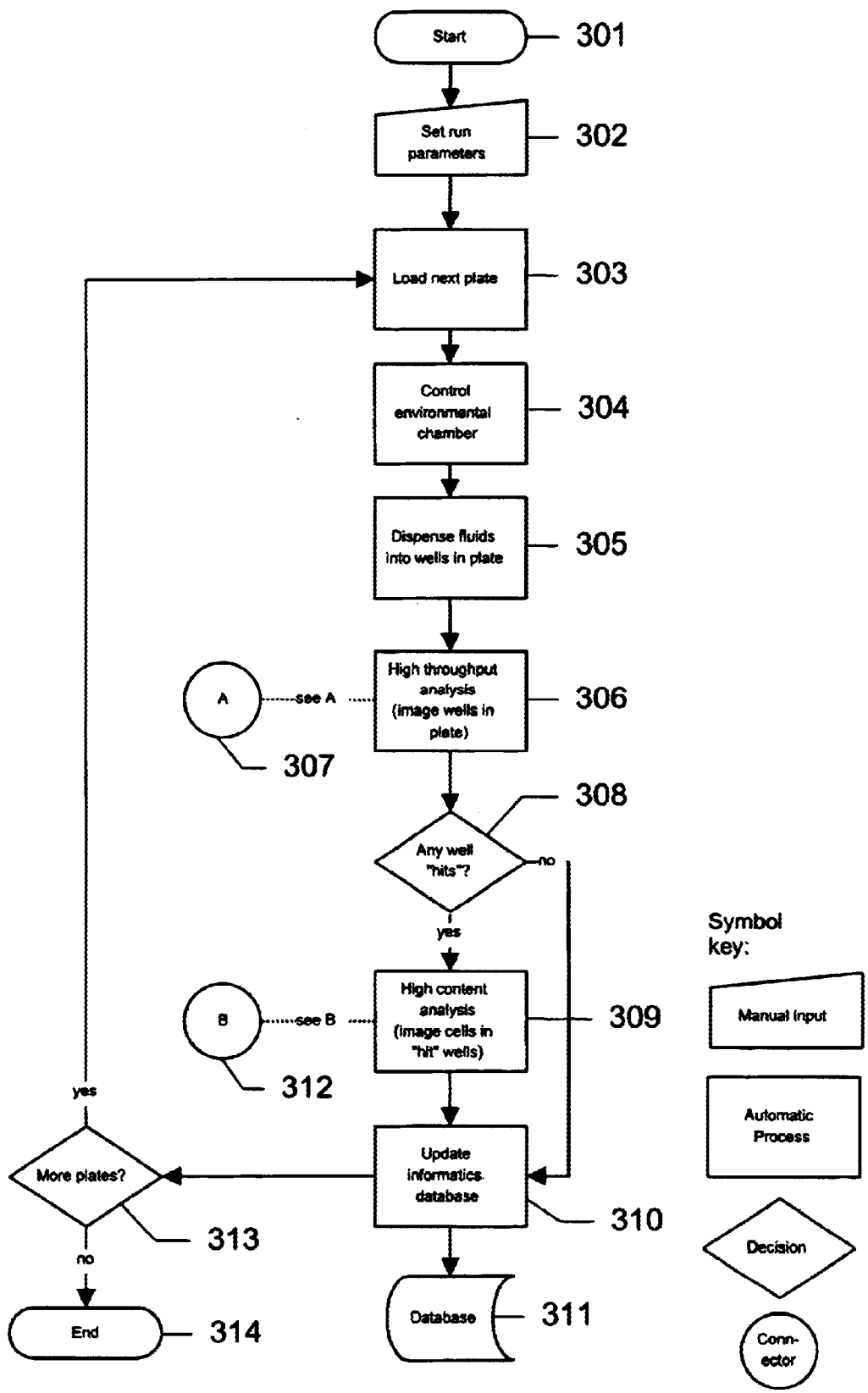
FIG. 11 is a flow chart defining the processing steps in the Dual Mode System for Cell Based Screening combining high throughput and high content screening of microtiter plates.

High throughput 'whole plate' reader systems are well known in the art and are commonly used as a component of an HTS system used to screen large numbers of compounds (Beggs et al. (1997), supra; McCaffrey et al. (1996), supra). The HTS of the present invention is carried out on the microtiter plate or microwell array by reading many or all wells in the plate simultaneously with sufficient resolution to make determinations on a well-by-well basis. That is, calculations are made by averaging the total signal output of many or all the cells or the bulk of the material in each well. Wells that exhibit some defined response in the HTS (the 'hits') are flagged by the system. Then on the same microtiter plate or microwell array, each well identified as a hit is measured via HCS as described above. Thus, the dual mode process involves:

1. Rapidly measuring numerous wells of a microtiter plate or microwell array,
2. Interpreting the data to determine the overall activity of fluorescently labeled reporter molecules in the cells on a well-by-well basis to identify "hits" (wells that exhibit a defined response),
3. Imaging numerous cells in each "hit" well, and
4. Interpreting the digital image data to determine the distribution, environment or activity of the fluorescently labeled reporter molecules in the individual cells (i.e. intracellular measurements) and the distribution of the cells to test for specific biological functions In a preferred embodiment of dual mode processing (FIG. 11), at the start of a run 301, the operator enters information 302 that describes the plate and its contents, specifies the filter settings and fluorescent channels to match the biological labels being used, the information sought and the camera settings to match the sample brightness. These parameters are stored in the system's database for easy retrieval for each automated run. The microtiter plate or microwell array is loaded into the cell screening system 303 either manually or automatically by controlling a robotic loading device. An optional environmental chamber 304 is controlled by the system to maintain the temperature, humidity and $CO_2$ levels in the air surrounding live cells in the microtiter plate or microwell array. An optional fluid delivery device 305 (see FIG. 8) is controlled by the system to dispense fluids into the wells during the scan.

Figure 12:
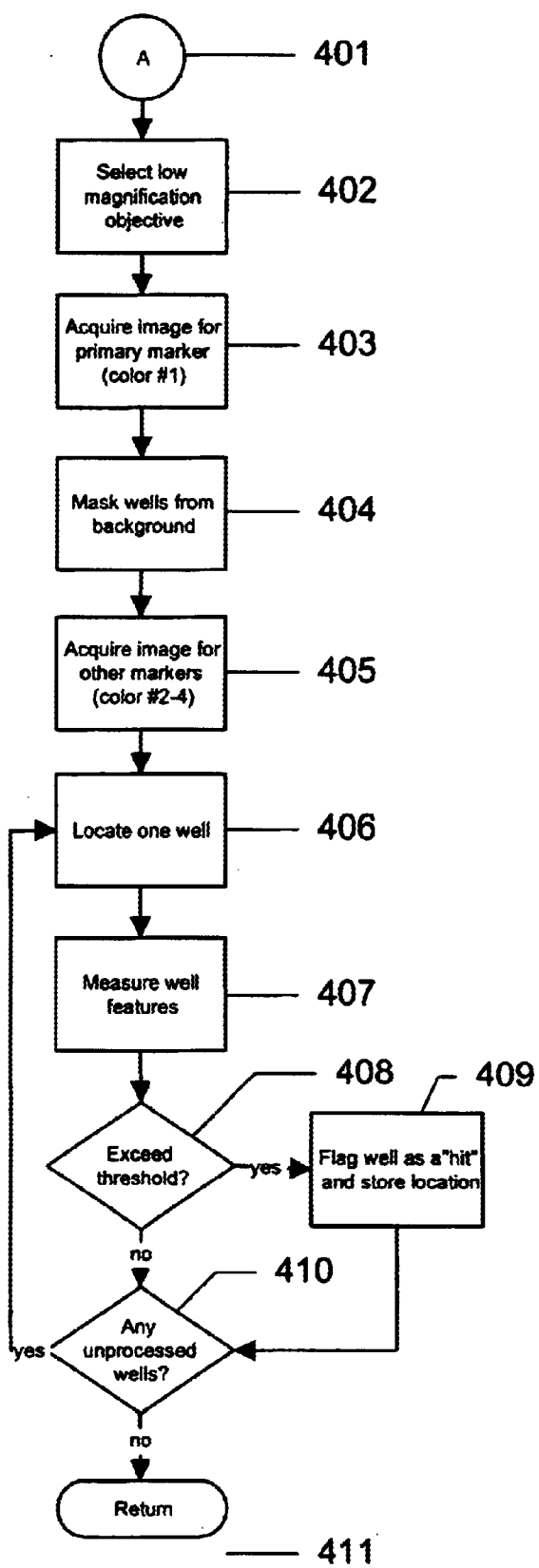
FIG. 12 is a flow chart defining the processing steps in the High Throughput mode of the System for Cell Based Screening.
Figure 13:
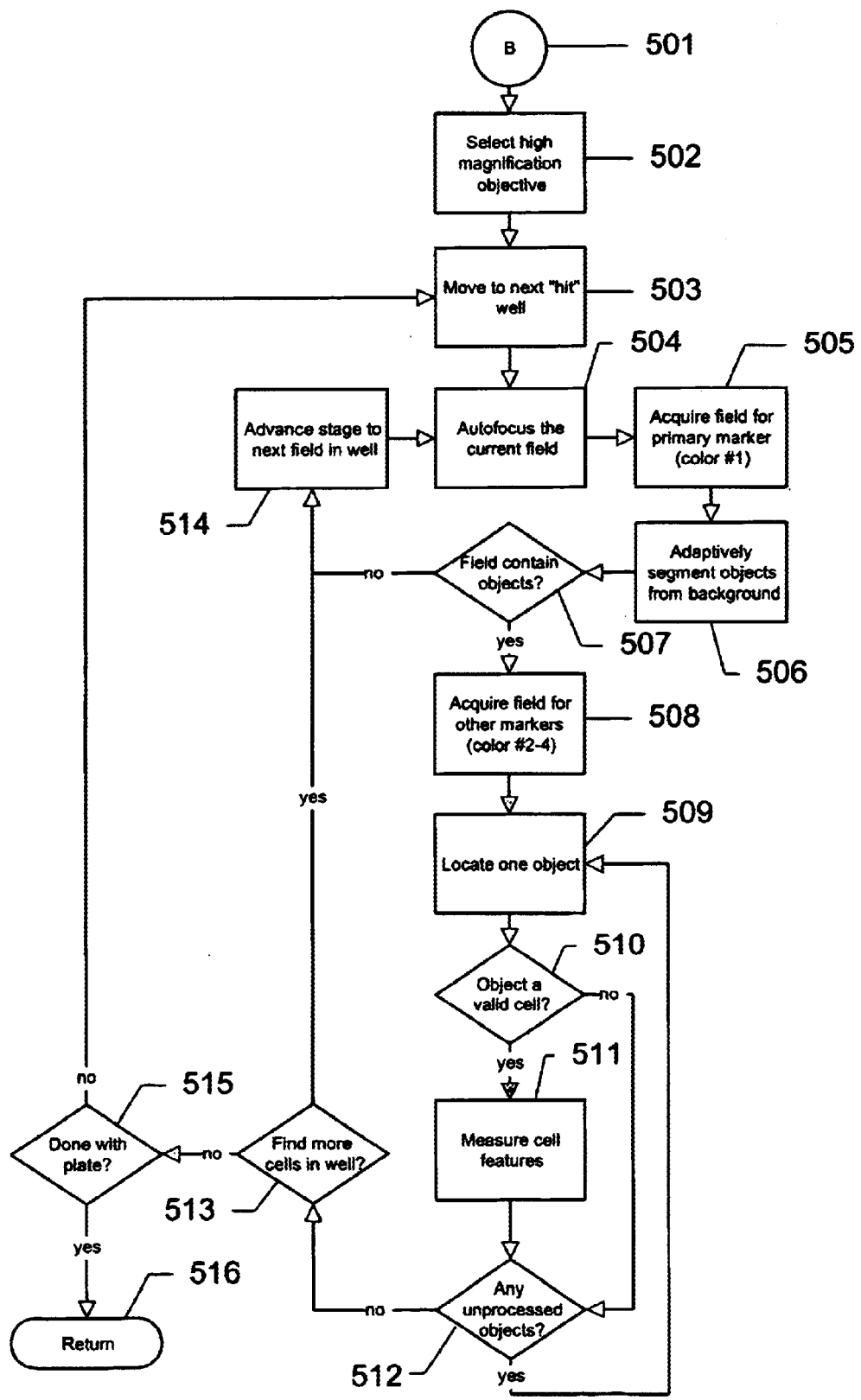
FIG. 13 is a flow chart defining the processing steps in the High Content mode of the System for Cell Based Screening.

High throughput processing 306 is first performed on the microtiter plate or microwell array by acquiring and analyzing the signal from each of the wells in the plate. The processing performed in high throughput mode 307 is illustrated in FIG. 12 and described below. Wells that exhibit some selected intensity response in this high throughput mode ("hits") are identified by the system. The system performs a conditional operation 308 that tests for hits. If hits are found, those specific hit wells are further analyzed in high content (micro level) mode 309. The processing performed in high content mode 312 is illustrated in FIG. 13. The system then updates 310 the informatics database 311 with results of the measurements on the plate. If there are more plates to be analyzed 313 the system loads the next plate 303; otherwise the analysis of the plates terminates 314.

The following discussion describes the high throughput mode illustrated in FIG. 12. The preferred embodiment of the system, the single platform dual mode screening system, will be described. Those skilled in the art will recognize that operationally the dual platform system simply involves moving the plate between two optical systems rather than moving the optics. Once the system has been set up and the plate loaded, the system begins the HTS acquisition and analysis 401. The HTS optical module is selected by controlling a motorized optical positioning device 402 on the dual mode system. In one fluorescence channel, data from a primary marker on the plate is acquired 403 and wells are isolated from the plate background using a masking procedure 404. Images are also acquired in other fluorescence channels being used 405. The region in each image corresponding to each well 406 is measured 407. A feature calculated from the measurements for a particular well is compared with a predefined threshold or intensity response 408, and based on the result the well is either flagged as a "hit" 409 or not. The locations of the wells flagged as hits are recorded for subsequent high content mode processing. If there are wells remaining to be processed 410 the program loops back 406 until all the wells have been processed 411 and the system exits high throughput mode.

Following HTS analysis, the system starts the high content mode processing 501 defined in FIG. 13. The system selects the HCS optical module 502 by controlling the motorized positioning system. For each "hit" well identified in high throughput mode, the XY stage location of the well is retrieved from memory or disk and the stage is then moved to the selected stage location 503. The autofocus procedure 504 is called for the first field in each hit well and then once every 5 to 8 fields within each well. In one channel, images are acquired of the primary marker 505 (typically cell nuclei counterstained with DAPI, Hoechst or PI fluorescent dye). The images are then segmented (separated into regions of nuclei and non-nuclei) using an adaptive thresholding procedure 506. The output of the segmentation procedure is a binary mask wherein the objects are white and the background is black. This binary image, also called a mask in the art, is used to determine if the field contains objects 507. The mask is labeled with a blob labeling method whereby each object (or blob) has a unique number assigned to it. If objects are found in the field, images are acquired for all other active channels 508, otherwise the stage is advanced to the next field 514 in the current well. Each object is located in the image for further analysis 509. Morphological features, such as area and shape of the objects, are used to select objects likely to be cell nuclei 510, and discard (do no further processing on) those that are considered artifacts. For each valid cell nucleus, the XYZ stage location is recorded, a small image of the cell is stored, and assay specific features are measured 511. The system then performs multiple tests on the cells by applying several analytical methods to measure features at each of several wavelengths. After measuring the cell features, the systems checks if there are any unprocessed objects in the current field 512. If there are any unprocessed objects, it locates the next object 509 and determines whether it meets the criteria for a valid cell nucleus 510, and measures its features. After processing all the objects in the current field, the system deteremines whether it needs to find more cells or fields in the current well 513. If it needs to find more cells or fields in the current well it advances the XYZ stage to the next field within the current well 515. Otherwise, the system checks whether it has any remaining hit wells to measure 515. If so, it advances to the next hit well 503 and proceeds through another cycle of acquisition and analysis, otherwise the HCS mode is finished 516.

In an alternative embodiment of the present invention, a method of kinetic live cell screening is provided. The previously described embodiments of the invention are used to characterize the spatial distribution of cellular components at a specific point in time, the time of chemical fixation. As such, these embodiments have limited utility for implementing kinetic based screens, due to the sequential nature of the image acquisition, and the amount of time required to read all the wells on a plate. For example, since a plate can require 30–60 minutes to read through all the wells, only very slow kinetic processes can be measured by simply preparing a plate of live cells and then reading through all the wells more than once. Faster kinetic processes can be measured by taking multiple readings of each well before proceeding to the next well, but the elapsed time between the first and last well would be too long, and fast kinetic processes would likely be complete before reaching the last well.

The kinetic live cell extension of the invention enables the design and use of screens in which a biological process is characterized by its kinetics instead of, or in addition to, its spatial characteristics. In many cases, a response in live cells can be measured by adding a reagent to a specific well and making multiple measurements on that well with the appropriate timing. This dynamic live cell embodiment of the invention therefore includes apparatus for fluid delivery to individual wells of the system in order to deliver reagents to each well at a specific time in advance of reading the well. This embodiment thereby allows kinetic measurements to be made with temporal resolution of seconds to minutes on each well of the plate. To improve the overall efficiency of the dynamic live cell system, the acquisition control program is modified to allow repetitive data collection from sub-regions of the plate, allowing the system to read other wells between the time points required for an individual well.

FIG. 8 describes an example of a fluid delivery device for use with the live cell embodiment of the invention and is described above. This set-up allows one set of pipette tips 705, or even a single pipette tip, to deliver reagent to all the wells on the plate. The bank of syringe pumps 701 can be used to deliver fluid to 12 wells simultaneously, or to fewer wells by removing some of the tips 705. The temporal resolution of the system can therefore be adjusted, without sacrificing data collection efficiency, by changing the number of tips and the scan pattern as follows. Typically, the data collection and analysis from a single well takes about 5 seconds. Moving from well to well and focusing in a well requires about 5 seconds, so the overall cycle time for a well is about 10 seconds. Therefore, if a single pipette tip is used to deliver fluid to a single well, and data is collected repetitively from that well, measurements can be made with about 5 seconds temporal resolution. If 6 pipette tips are used to deliver fluids to 6 wells simultaneously, and the system repetitively scans all 6 wells, each scan will require 60 seconds, thereby establishing the temporal resolution. For slower processes which only require data collection every 8 minutes, fluids can be delivered to one half of the plate, by moving the plate during the fluid delivery phase, and then repetitively scanning that half of the plate. Therefore, by adjusting the size of the sub-region being scanned on the plate, the temporal resolution can be adjusted without having to insert wait times between acquisitions. Because the system is continuously scanning and acquiring data, the overall time to collect a kinetic data set from the plate is then simply the time to perform a single scan of the plate, multiplied by the number of time points required. Typically, 1 time point before addition of compounds and 2 or 3 time points following addition should be sufficient for screening purposes.

Figure 14:
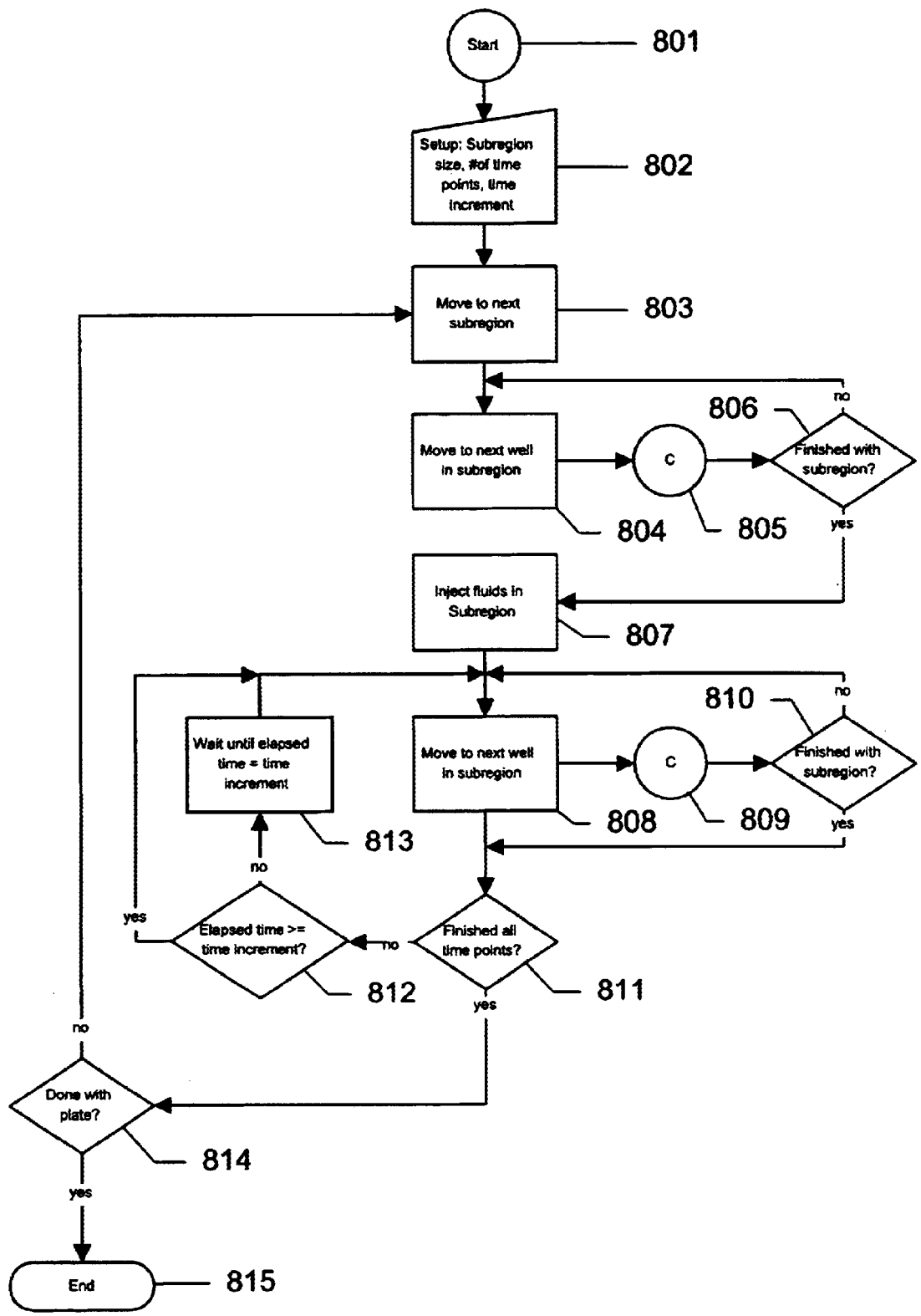
FIG. 14 is a flow chart defining the processing steps required for acquiring kinetic data in the High Content mode of the System for Cell Based Screening.
Figure 15:
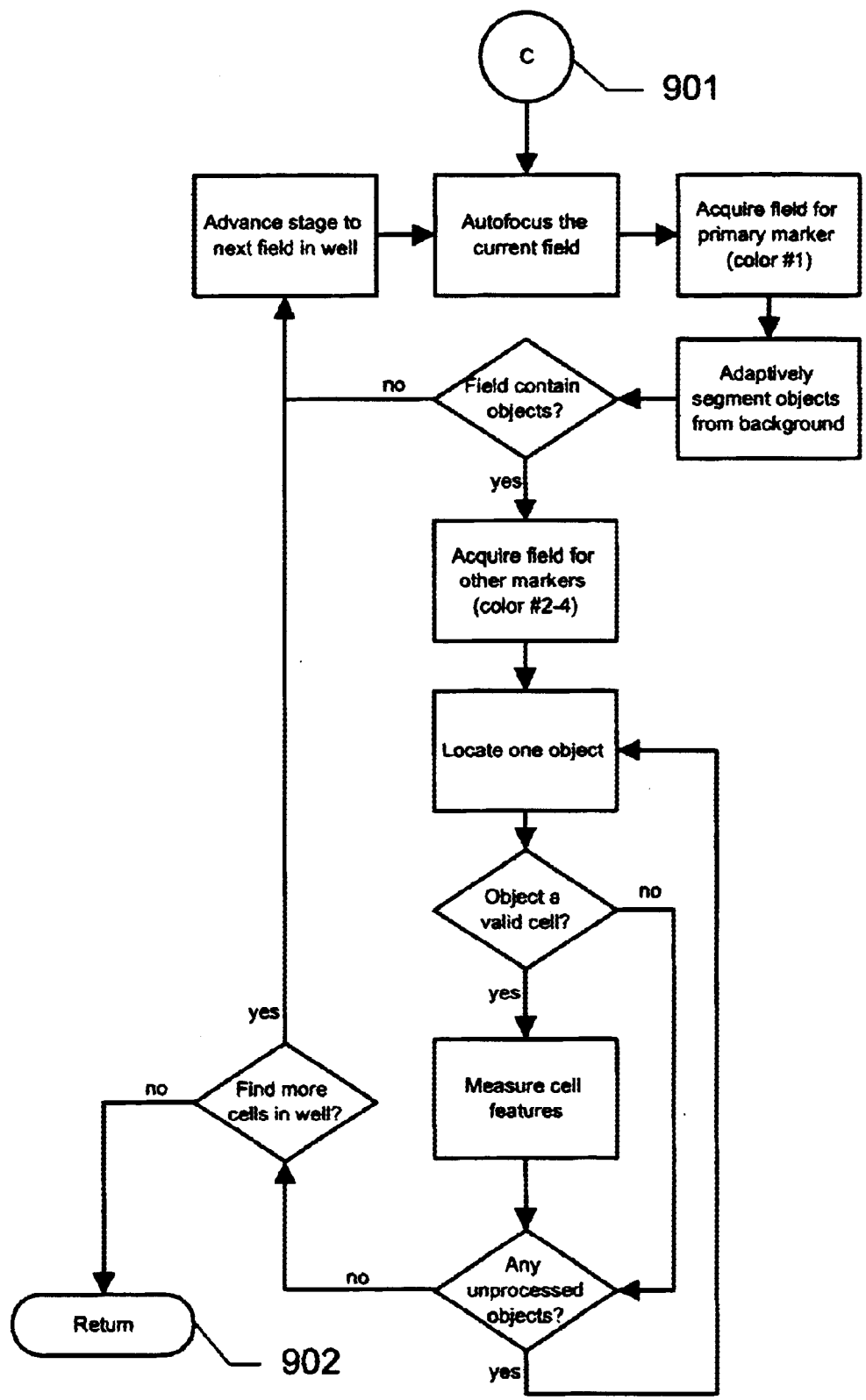
FIG. 15 is a flow chart defining the processing steps performed within a well during the acquisition of kinetic data.

FIG. 14 shows the acquisition sequence used for kinetic analysis. The start of processing 801 is configuration of the system, much of which is identical to the standard HCS configuration. In addition, the operator must enter information specific to the kinetic analysis being performed 802, such as the sub-region size, the number of time points required, and the required time increment. A sub-region is a group of wells that will be scanned repetitively in order to accumulate kinetic data. The size of the sub-region is adjusted so that the system can scan a whole sub-region once during a single time increment, thus minimizing wait times. The optimum sub-region size is calculated from the setup parameters, and adjusted if necessary by the operator. The system then moves the plate to the first sub-region 803, and to the first well in that sub-region 804 to acquire the prestimulation (time=0) time points. The acquisition sequence performed in each well is exactly the same as that required for the specific HCS being run in kinetic mode. FIG. 15 details a flow chart for that processing. All of the steps between the start 901 and the return 902 are identical to those described as steps 504–514 in FIG. 13.

After processing each well in a sub-region, the system checks to see if all the wells in the sub-region have been processed 806 (FIG. 14), and cycles through all the wells until the whole region has been processed. The system then moves the plate into position for fluid addition, and controls fluidic system delivery of fluids to the entire sub-region 807. This may require multiple additions for sub-regions which span several rows on the plate, with the system moving the plate on the X,Y stage between additions. Once the fluids have been added, the system moves to the first well in the sub-region 808 to begin acquisition of time points. The data is acquired from each well 809 and as before the system cycles through all the wells in the sub-region 810. After each pass through the sub-region, the system checks whether all the time points have been collected 811 and if not, pauses 813 if necessary 812 to stay synchronized with the requested time increment. Otherwise, the system checks for additional sub-regions on the plate 814 and either moves to the next sub-region 803 or finishes 815. Thus, the kinetic analysis mode comprises operator identification of sub-regions of the microtiter plate or microwells to be screened, based on the kinetic response to be investigated, with data acquisitions within a sub-region prior to data acquisition in subsequent sub-regions.

Specific Screens

In another aspect of the present invention, cell screening methods and machine readable storage medium comprising a program containing a set of instructions for causing a cell screening system to execute procedures for defining the distribution and activity of specific cellular constituents and processes is provided. In a preferred embodiment, the cell screening system comprises a high magnification fluorescence optical system with a stage adapted for holding cells and a means for moving the stage, a digital camera, a light source for receiving and processing the digital data from the digital camera, and a computer means for receiving and processing the digital data from the digital camera. This aspect of the invention comprises programs that instruct the cell screening system to define the distribution and activity of specific cellular constituents and processes, using the luminescent probes, the optical imaging system, and the pattern recognition software of the invention. Preferred embodiments of the machine readable storage medium comprise programs consisting of a set of instructions for causing a cell screening system to execute the procedures set forth in FIGS. 9, 11, 12, 13, 14 or 15. Another preferred embodiment comprises a program consisting of a set of instructions for causing a cell screening system to execute procedures for detecting the distribution and activity of specific cellular constituents and processes. In most preferred embodiments, the cellular processes include, but are not limited to, nuclear translocation of a protein, cellular morphology, apoptosis, receptor internalization, and protease-induced translocation of a protein.

In a preferred embodiment, the cell screening methods are used to identify compounds that modify the various cellular processes. The cells can be contacted with a test compound, and the effect of the test compound on a particular cellular process can be analyzed. Alternatively, the cells can be contacted with a test compound and a known agent that modifies the particular cellular process, to determine whether the test compound can inhibit or enhance the effect of the known agent. Thus, the methods can be used to identify test compounds that increase or decrease a particular cellular response, as well as to identify test compounds that affects the ability of other agents to increase or decrease a particular cellular response.

In another preferred embodiment, the locations containing cells are analyzed using the above methods at low resolution in a high throughput mode, and only a subset of the locations containing cells are analyzed in a high content mode to obtain luminescent signals from the luminescently labeled reporter molecules in subcellular compartments of the cells being analyzed.

The following examples are intended for purposes of illustration only and should not be construed to limit the scope of the invention, as defined in the claims appended hereto.

The various chemical compounds, reagents, dyes, and antibodies that are referred to in the following Examples are commercially available from such sources as Sigma Chemical (St. Louis, Mo.), Molecular Probes (Eugene, Oreg.), Aldrich Chemical Company (Milwaukee, Wis.), Accurate Chemical Company (Westbury, N.Y.), Jackson Immunolabs, and Clontech (Palo Alto, Calif.).

EXAMPLE 1

Cytoplasm to Nucleus Translocation Screening a. Transcription Factors

Regulation of transcription of some genes involves activation of a transcription factor in the cytoplasm, resulting in that factor being transported into the nucleus where it can initiate transcription of a particular gene or genes. This change in transcription factor distribution is the basis of a screen for the cell-based screening system to detect compounds that inhibit or induce transcription of a particular gene or group of genes. A general description of the screen is given followed by a specific example.

The distribution of the transcription factor is determined by labeling the nuclei with a DNA specific fluorophore like Hoechst 33423 and the transcription factor with a specific fluorescent antibody. After autofocusing on the Hoechst labeled nuclei, an image of the nuclei is acquired in the cell-based screening system and used to create a mask by one of several optional thresholding methods, as described supra. The morphological descriptors of the regions defined by the mask are compared with the user defined parameters and valid nuclear masks are identified and used with the following method to extract transcription factor distributions. Each valid nuclear mask is eroded to define a slightly smaller nuclear region. The original nuclear mask is then dilated in two steps to define a ring shaped region around the nucleus, which represents a cytoplasmic region. The average antibody fluorescence in each of these two regions is determined, and the difference between these averages is defined as the NucCyt Difference. Two examples of determining nuclear translocation are discussed below and illustrated in FIGS. 10A–J. FIG. 10A illustrates an unstimulated cell with its nucleus 200 labeled with a blue fluorophore and a transcription factor in the cytoplasm 201 labeled with a green fluorophore. FIG. 10B illustrates the nuclear mask 202 derived by the cell-based screening system. FIG. 10C illustrates the cytoplasm 203 of the unstimulated cell imaged at a green wavelength. FIG. 10D illustrates the nuclear mask 202 is eroded (reduced) once to define a nuclear sampling region 204 with minimal cytoplasmic distribution. The nucleus boundary 202 is dilated (expanded) several times to form a ring that is 2–3 pixels wide that is used to define the cytoplasmic sampling region 205 for the same cell. FIG. 10E further illustrates a side view which shows the nuclear sampling region 204 and the cytoplasmic sampling region 205. Using these two sampling regions, data on nuclear translocation can be automatically analyzed by the cell-based screening system on a cell by cell basis. FIGS. 10F–J illustrates the strategy for determining nuclear translocation in a stimulated cell. FIG. 10F illustrates a stimulated cell with its nucleus 206 labeled with a blue fluorophore and a transcription factor in the cytoplasm 207 labeled with a green fluorophore. The nuclear mask 208 in FIG. 10G is derived by the cell based screening system. FIG. 10H illustrates the cytoplasm 209 of a stimulated cell imaged at a green wavelength. FIG. 10I illustrates the nuclear sampling region 211 and cytoplasmic sampling region 212 of the stimulated cell. FIG. 10J further illustrates a side view which shows the nuclear sampling region 211 and the cytoplasmic sampling region 212.

Figure 16:
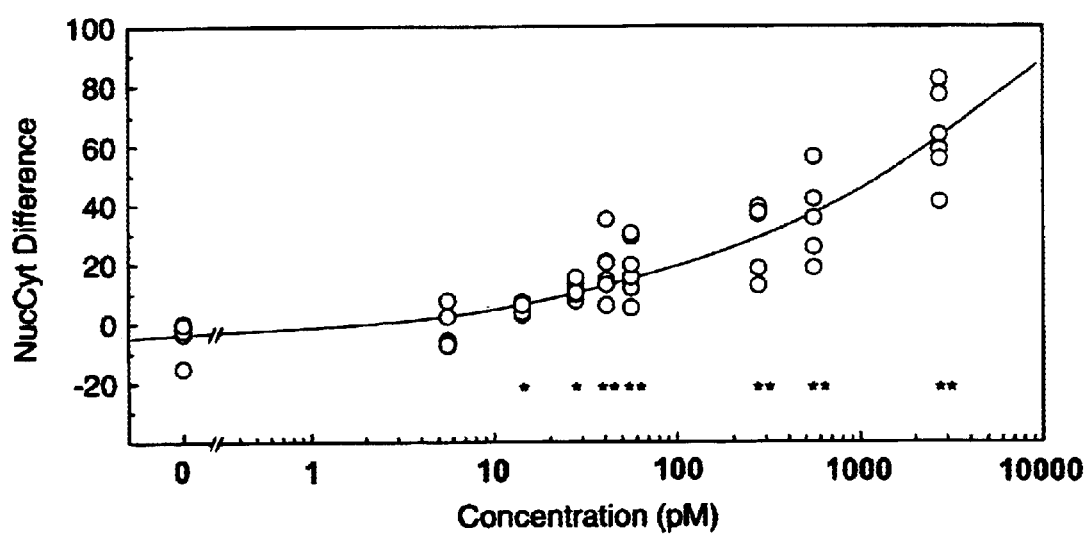
FIG. 16 is an example of data from a known inhibitor of translocation.
Figure 17:
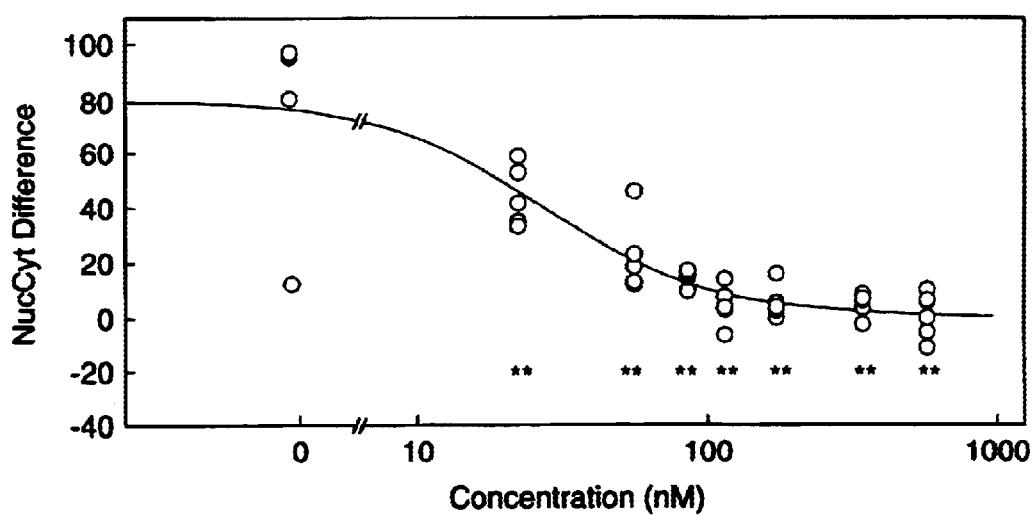
FIG. 17 is an example of data from a known stimulator of translocation.

A specific application of this method has been used to validate this method as a screen. A human cell line was plated in 96 well microtiter plates. Some rows of wells were titrated with IL-1, a known inducer of the NF-KB transcription factor. The cells were then fixed and stained by standard methods with a fluorescein labeled antibody to the transcription factor, and Hoechst 33423. The cell-based screening system was used to acquire and analyze images from this plate and the NucCyt Difference was found to be strongly correlated with the amount of agonist added to the wells as illustrated in FIG. 16. In a second experiment, an antagonist to the receptor for IL-1, IL-1RA was titrated in the presence of IL-1α, progressively inhibiting the translocation induced by IL-1α. The NucCyt Difference was found to strongly correlate with this inhibition of translocation, as illustrated in FIG. 17.

Additional experiments have shown that the NucCyt Difference, as well as the NucCyt ratio, gives consistent results over a wide range of cell densities and reagent concentrations, and can therefore be routinely used to screen compound libraries for specific nuclear translocation activity. Furthermore, the same method can be used with antibodies to other transcription factors, or GFP-transcription factor chimeras, or fluorescently labeled transcription factors introduced into living or fixed cells, to screen for effects on the regulation of transcription factor activity.

Figure 18:
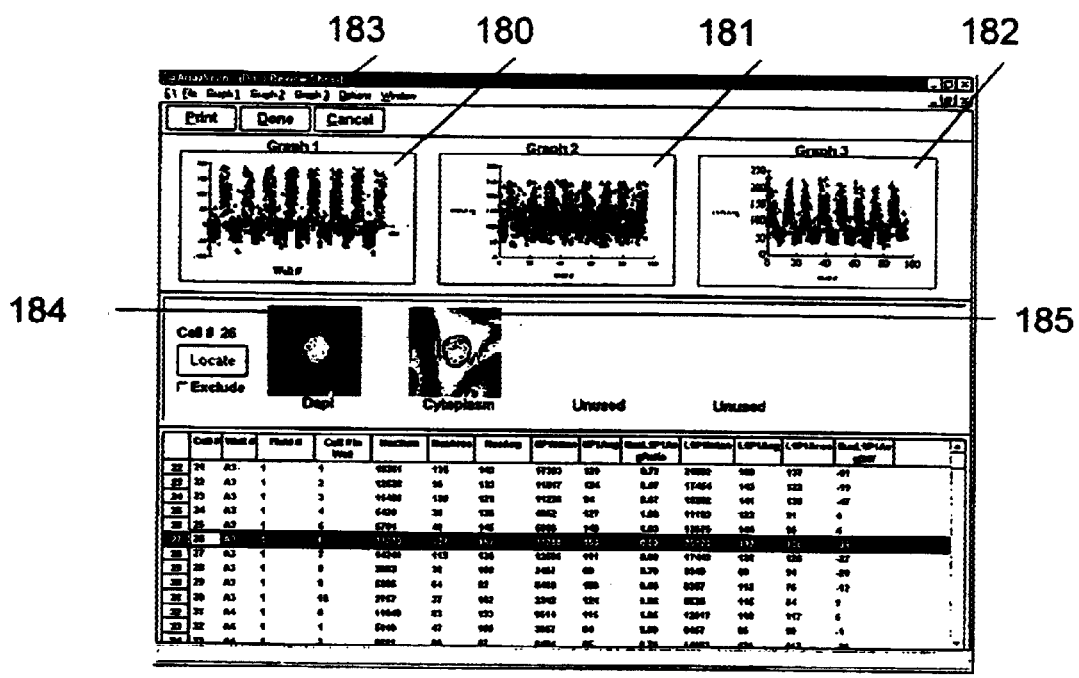
FIG. 18 illustrates data presentation on a graphical display.

FIG. 18 is a representative display on a PC screen of data which was obtained in accordance with Example 1. Graph 1 180 plots the difference between the average antibody fluorescence in the nuclear sampling region and cytoplasmic sampling region, NucCyt Difference verses Well #. Graph 2 181 plots the average fluorescence of the antibody in the nuclear sampling region, NP1 average, versus the Well #. Graph 3 182 plots the average antibody fluorescence in the cytoplasmic sampling region, LIP1 average, versus Well #. The software permits displaying data from each cell. For example, FIG. 18 shows a screen display 183, the nuclear image 184 and the fluorescent antibody image 185 for cell #26.

NucCyt Difference referred to in graph 1 180 of FIG. 18 is the difference between the average cytoplasmic probe (fluorescent reporter molecule) intensity and the average nuclear probe (fluorescent reporter molecule) intensity. NP1 average referred to in graph 2 181 of FIG. 18 is the average of cytoplasmic probe (fluorescent reporter molecule) intensity within the nuclear sampling region. L1P1 average referred to in graph 3 182 of FIG. 18 is the average probe (fluorescent reporter molecule) intensity within the cytoplasmic sampling region.

It will be understood by one of skill in the art that this aspect of the invention can be performed using other transcription factors that translocate from the cytoplasm to the nucleus upon activation. In another specific example, activation of the c-fos transcription factor was assessed by defining its spatial position within cells. Activated c-fos is found only within the nucleus, while inactivated c-fos resides within the cytoplasm.

3T3 cells were plated at 5000–10000 cells per well in a Polyfiltronics 96-well plate. The cells were allowed to attach and grow overnight. The cells were rinsed twice with 100 µl serum-free medium, incubated for 24–30 hours in serum-free MEM culture medium, and then stimulated with platelet derived growth factor (PDGF-BB) (Sigma Chemical Co., St. Louis, Mo.) diluted directly into serum free medium at concentrations ranging from 1–50 ng/ml for an average time of 20 minutes.

Following stimulation, cells were fixed for 20 minutes in 3.7% formaldehyde solution in 1X Hanks buffered saline solution (HBSS). After fixation, the cells were washed with HBSS to remove residual fixative, permeabilized for 90 seconds with 0.5% Triton X-100 solution in HBSS, and washed twice with HBSS to remove residual detergent. The cells were then blocked for 15 minutes with a 0.1% solution of BSA in HBSS, and further washed with HBSS prior to addition of diluted primary antibody solution.

c-Fos rabbit polyclonal antibody (Calbiochem, PC05) was diluted 1:50 in HBSS, and 50 µl of the dilution was applied to each well. Cells were incubated in the presence of primary antibody for one hour at room temperature, and then incubated for one hour at room temperature in a light tight container with goat anti-rabbit secondary antibody conjugated to ALEXA™ 488 (Molecular Probes), diluted 1:500 from a 100 µg/ml stock in HBSS. Hoechst DNA dye (Molecular Probes) was then added at a 1:1000 dilution of the manufacturer's stock solution (10 mg/ml). The cells were then washed with HBSS, and the plate was sealed prior to analysis with the cell screening system of the invention. The data from these experiments demonstrated that the methods of the invention could be used to measure transcriptional activation of c-fos by defining its spatial position within cells.

One of skill in the art will recognize that while the following method is applied to detection of c-fos activation, it can be applied to the analysis of any transcription factor that translocates from the cytoplasm to the nucleus upon activation. Examples of such transcription factors include, but are not limited to fos and jun homologs, NF-KB (nuclear factor kappa from B cells), NFAT (nuclear factor of activated T-lymphocytes), and STATs (signal transducer and activator of transcription) factors (For example, see Strehlow, I., and Schindler, C. 1998. *J. Biol. Chem.* 273:28049–28056; Chow, et al. 1997 *Science.* 278:1638–1641; Ding et al. 1998 *J. Biol. Chem.* 273:28897–28905; Baldwin, 1996. *Annu Rev Immunol.* 14:649–83; Kuo, C. T., and J. M. Leiden. 1999. *Annu Rev Immunol.* 17:149–87; Rao, et al. 1997. *Annu Rev Immunol.* 15:707–47; Masuda, et al. 1998. *Cell Signal.* 10:599–611; Hoey, T., and U. Schindler. 1998. *Curr Opin Genet Dev.* 8:582–7; Liu, et al. 1998. *Curr Opin Immunol.* 10:271–8.)

Thus, in this aspect of the invention, indicator cells are treated with test compounds and the distribution of luminescently labeled transcription factor is measured in space and time using a cell screening system, such as the one disclosed above. The luminescently labeled transcription factor may be expressed by or added to the cells either before, together with, or after contacting the cells with a test compound. For example, the transcription factor may be expressed as a luminescently labeled protein chimera by transfected indicator cells. Alternatively, the luminescently labeled transcription factor may be expressed, isolated, and bulk-loaded into the indicator cells as described above, or the transcription factor may be luminescently labeled after isolation. As a further alternative, the transcription factor is expressed by the indicator cell, which is subsequently contacted with a luminescent label, such as an antibody, that detects the transcription factor.

In a further aspect, kits are provided for analyzing transcription factor activation, comprising an antibody that specifically recognizes a transcription factor of interest, and instructions for using the antibody for carrying out the methods described above. In a preferred embodiment, the transcription factor-specific antibody, or a secondary antibody that detects the transcription factor antibody, is luminescently labeled. In further preferred embodiments, the kit contains cells that express the transcription factor of interest, and/or the kit contains a compound that is known to modify activation of the transcription factor of interest, including but not limited to platelet derived growth factor (PDGF) and serum, which both modify fos activation; and interleukin 1(IL-1) and tumor necrosis factor (TNF), which both modify NF-KB activation.

In another embodiment, the kit comprises a recombinant expression vector comprising a nucleic acid encoding a transcription factor of interest that translocates from the cytoplasm to the nucleus upon activation, and instructions for using the expression vector to identify compounds that modify transcription factor activation in a cell of interest. Alternatively, the kits contain a purified, luminescently labeled transcription factor. In a preferred embodiment, the transcription factor is expressed as a fusion protein with a luminescent protein, including but not limited to green fluorescent protein, luceriferase, or mutants or fragments thereof. In various preferred embodiments, the kit further contains cells that are transfected with the expression vector, an antibody or fragment that specifically bind to the transcription factor of interest, and/or a compound that is known to modify activation of the transcription factor of interest (as above).

b. Protein Kinases

The cytoplasm to nucleus screening methods can also be used to analyze the activation of any protein kinase that is present in an inactive state in the cytoplasm and is transported to the nucleus upon activation, or that phosphorylates a substrate that translocates from the cytoplasm to the nucleus upon phosphorylation. Examples of appropriate protein kinases include, but are not limited to extracellular signal-regulated protein kinases (ERKs), c-Jun amino-terminal kinases (JNKs), Fos regulating protein kinases (FRKs), p38 mitogen activated protein kinase (p38MAPK), protein kinase A (PKA), and mitogen activated protein kinase kinases (MAPKKs). (For example, see Hall, et al. 1999. *J Biol Chem.* 274:376–83; Han, et al. 1995. *Biochim. Biophys. Acta.* 1265:224–227; Jaaro et al. 1997. *Proc. Natl. Acad. Sci. U.S.A.* 94:3742–3747; Taylor, et al. 1994. *J. Biol. Chem.* 269:308–318; Zhao, Q., and F. S. Lee. 1999. *J Biol Chem.* 274:8355–8; Paolilloet al. 1999. *J Biol Chem.*

274:6546–52; Coso et al. 1995. Cell 81:1137–1146; Tibbles, L. A., and J. R. Woodgett. 1999. *Cell Mol Life Sci.* 55:1230–54; Schaeffer, H. J., and M. J. Weber. 1999. *Mol Cell Biol.* 19:2435–44.)

Alternatively, protein kinase activity is assayed by monitoring translocation of a luminescently labeled protein kinase substrate from the cytoplasm to the nucleus after being phosphorylated by the protein kinase of interest. In this embodiment, the substrate is non-phosphorylated and cytoplasmic prior to phosphorylation, and is translocated to the nucleus upon phosphorylation by the protein kinase. There is no requirement that the protein kinase itself translocates from the cytoplasm to the nucleus in this embodiment. Examples of such substrates (and the corresponding protein kinase) include, but are not limited to c-jun (JNK substrate); fos (FRK substrate), and p38 (p38 MAPK substrate).

Thus, in these embodiments, indicator cells are treated with test compounds and the distribution of luminescently labeled protein kinase or protein kinase substrate is measured in space and time using a cell screening system, such as the one disclosed above. The luminescently labeled protein kinase or protein kinase substrate may be expressed by or added to the cells either before, together with, or after contacting the cells with a test compound. For example, the protein kinase or protein kinase substrate may be expressed as a luminescently labeled protein chimera by transfected indicator cells. Alternatively, the luminescently labeled protein kinase or protein kinase substrate may be expressed, isolated, and bulk-loaded into the indicator cells as described above, or the protein kinase or protein kinase substrate may be luminescently labeled after isolation. As a further alternative, the protein kinase or protein kinase substrate is expressed by the indicator cell, which is subsequently contacted with a luminescent label, such as a labeled antibody, that detects the protein kinase or protein kinase substrate.

In a further embodiment, protein kinase activity is assayed by monitoring the phosphorylation state (ie: phosphorylated or not phosphorylated) of a protein kinase substrate. In this embodiment, there is no requirement that either the protein kinase or the protein kinase substrate translocate from the cytoplasm to the nucleus upon activation. In a preferred embodiment, phosphorylation state is monitored by contacting the cells with an antibody that binds only to the phosphorylated form of the protein kinase substrate of interest (For example, as disclosed in U.S. Pat. No. 5,599,681).

In another preferred embodiment, a biosensor of phosphorylation is used. For example, a luminescently labeled protein or fragment thereof can be fused to a protein that has been engineered to contain (a) a phosphorylation site that is recognized by a protein kinase of interest; and (b) a nuclear localization signal that is unmasked by the phosphorylation. Such a biosensor will thus be translocated to the nucleus upon phosphorylation, and its translocation can be used as a measure of protein kinase activation.

In another aspect, kits are provided for analyzing protein kinase activation, comprising a primary antibody that specifically binds to a protein kinase, a protein kinase substrate, or a phosphorylated form of the protein kinase substrate of interest and instructions for using the primary antibody to identify compounds that modify protein kinase activation in a cell of interest. In a preferred embodiment, the primary antibody, or a secondary antibody that detects the primary antibody, is luminescently labeled. In other preferred embodiments, the kit further comprises cells that express the protein kinase of interest, and/or a compound that is known to modify activation of the protein kinase of interest, including but not limited to dibutyryl cAMP (modifies PKA), forskolin (PKA), and anisomycin (p38MAPK).

Alternatively, the kits comprise an expression vector encoding a protein kinase or a protein kinase substrate of interest that translocates from the cytoplasm to the nucleus upon activation and instructions for using the expression vector to identify compounds that modify protein kinase activation in a cell of interest. Alternatively, the kits contain a purified, luminescently labeled protein kinase or protein kinase substrate. In a preferred embodiment, the protein kinase or protein kinase substrate of interest is expressed as a fusion protein with a luminescent protein. In further preferred embodiments, the kit further comprises cells that are transfected with the expression vector, an antibody or fragment thereof that specifically binds to the protein kinase or protein kinase substrate of interest, and/or a compound that is known to modify activation of the protein kinase of interest. (as above)

In another aspect, the present invention comprises a machine readable storage medium comprising a program containing a set of instructions for causing a cell screening system to execute the methods disclosed for analyzing transcription factor or protein kinase activation, wherein the cell screening system comprises an optical system with a stage adapted for holding a plate containing cells, a digital camera, a means for directing fluorescence or luminescence emitted from the cells to the digital camera, and a computer means for receiving and processing the digital data from the digital camera.

EXAMPLE 2

Automated Screen for Compounds That Modify Cellular Morphology

Changes in cell morphology are associated with a number of cellular conditions, such as hypertrophy, morphogenesis and differentiation, attachment to a substrate and subsequent spreading, growth and division, polarity and motility, cell-cell junction formation and multicellular colony formation.

Cellular hypertrophy has been associated with a pathological cascade of alterations in gene expression, and can be characterized in cell culture by an alteration in cell size that is clearly visible in adherent cells. Cardiac cell hypertrophy is one example of a morphological change with direct consequence for human disease.

Cellular morphogenesis and differentiation can be evaluated by cell size and shape. For example, differentiation of muscle is the result of fusion and elongation of myocytes to form a multinucleated synsicium. Cell size can also be measured to determine the attachment and spreading of adherent cells.

Cell attachment to substrate molecules is an important step for the metastasis of cancer cells and leukocyte activation during the inflammatory response. Measurement of the number of attached cells is one measure of cell adhesion. Attachment reflects receptor binding not activation and is distinct from and complementary to cell spreading.

Cell spreading, the measurement of cell size and shape following cell adhesion, is the result of selective binding of cell surface receptors to substrate ligands and subsequent activation of signaling pathways to the cytoskeleton. Activation of cells induces symmetric formation of lamella on all sides of the cell and produces disk-shaped morphological changes described as cell spreading. After cells have attached and then spread, cells may then initiate movement.

Cell motility takes place when the lamella forms on one side of the cell and pulls the cell forward. In contrast to spreading cells, moving cells have an asymmetric shape as they move. Cells also will directionally transport material across their surfaces. For example, single moving cells often form broad lammellae followed by bulbous or elongated cell bodies and tails. Keratinocyte movement during wound healing is reflected in coordinated movement of cells as a sheet with lamellar formation at the exposed edge.

Cell-cell junction formation can be detected by the presence of proteins specific for adherens, occludens, or gap junctions, and cell morphology is influenced by drugs that affect the function of such proteins. For example, drugs that block cadherin function in cell-cell junctions reduce the size of colonies and reduce the number of cells per colony.

Cell-cell communication can be detected by passage of small fluorescent molecules from one cell to opposing neighbors. The gap junction-permeant, luminescent molecule, lucifer yellow, could be introduced into a few cells per colony and would remain localized to those cells without functional gap junctions. If gap junctions were functional, the lucifer yellow would passage from one cell to its neighbors, thus labeling the entire colony. Therefore, measurement of the fraction of lucifer yellow-labeled cells per colony is a functional measure of cell-cell comunication within that colony.

The size of colonies and the number of cells within the colonies are measures of colony formation. Multicellular colony formation is important, for example, in epithelial cell transporter function and endothelial cell tube formation during angiogenesis.

Neoplastic changes such as elongated, fusiform cell shapes and colony morphologies is induced in stem cells and provides a measure of genetic transformation in the presence of cancer-causing mutagens. The asymmetric elongation of cell colonies under these conditions, as measured by the morphology assay, is a measure of drug mutagenicity in stem cells.

There is a need for methods that can analyze the efficacy as well as the potency of drug candidates on these various aspects of cell morphology. Therefore, in another aspect, the present invention provides automated cell-based screening methods for analyzing various aspects of cell morphology, as well as associated software for carrying out the automated methods.

Cellular Hypertrophy

The present invention provides automated assays to analyze cellular hypertrophy, and associated software for carrying out the assay on a cell screening system. Cell arrays are treated with test compounds and then fixed and labeled with a fluorescent marker for cell area. There are three fundamental ways of staining the cell area of cells: labeling the cytosol, for example with fluorescent biomolecules or with soluble dyes trapped in the cytosol, labeling the plasma membrane, and labeling the cytoskeleton (See the table below). Protocols for cell staining with these various agents are well known to those skilled in the art. Any method for staining the cell body so that it can be discriminated from background will allow the cell area to be distinguished by intensity thresholding. Cells can stained live or after fixation and the cell area can be measured on cells live or fixed. For example, live cells stained with DiIC16 have homogeneously labeled plasma membranes and the projected cross-sectional area of the cell is uniformly discriminated from background by fluorescence intensity of the dye. Live cells stained with cytosolic stains such as CMFDA produce a fluorescence intensity that is proportional to cell thickness. Although cell labeling is dimmer in thin regions of the cell, total cell area can be discriminated from background. Fixed cells can be stained with cytoskeletal markers such as rhodamine-phalloidin that label polymerized actin. Actin labeling permits discrimination of the total cell area from background since cortical actin staining delineates cell borders, thus maximizing detail at the perimeter. Rhodamine-phalloidin is our stain of choice, because it reliably stains many cell types and gives stable signals.

| EXAMPLES OF CELL NUMBER, SIZE AND AREA MARKERS |
| --- |
| Cytoskeletal Markers |
| ALEXA ™ 488 phalloidin (Molecular Probes, Oregon)<br>Tubulin-green fluorescent protein chimeras<br>Cytokeratin-green fluorescent protein chimeras<br>Antibodies to cytoskeletal proteins |
| Cytosolic Volume Markers |
| Green fluorescent proteins (and chimeric variants of proteins in the cytoplasm)<br>Derivitized total protein (cells labeled with FITC)<br>Chloromethylfluorescein diacetate (CMFDA)<br>Calcein green<br>BCECF/AM ester<br>Rhodamine dextran |
| Cell Surface Markers for Lipid, Protein, or Oligosaccharide |
| Dihexadecyl tetramethylindocarbocyanine perchlorate (DiIC16) lipid dyes<br>Triethylammonium propyl dibutylamino styryl pyridinium (FM 4-64, FM 1-43)<br>MITOTRACKER ™ Green FM<br>Lectins to oligosaccharides such as fluorescein concanavalin A or wheat germ<br>SYPRO ™ Red non-specific protein markers<br>Antibodies to various surface proteins such as epidermal growth factor<br>Biotin labelin of surface proteins followed by fluorescent strepavidin labeleing |

In a preferred embodiment, a DNA label, including but not limited to Hoechst 33342, is also used. Nuclear markers are not required as hypertrophy can be measured with cytoplasmic markers alone, at single time intervals or as a kinetic assay at multiple time intervals.

A screen to analyze cellular hypertrophy was implemented using the following strategy. Primary rat myocytes were cultured in 96 well plates, treated with various compounds and then fixed and labeled with a fluorescent marker for cell area (cytoplasmic marker). Using the preferred embodiment, two images were acquired, one of the Hoechst labeled nuclei and one of the fluorescent cytoplasm image. The nuclei were identified by thresholding to create a mask, and then comparing the nuclear morphological descriptors of the mask with a set of user defined descriptor values. Each non-nucleus image (or "cytoplasmic image") was processed separately. The original cytoplasm image was thresholded, creating a cytoplasmic mask image. Local regions containing cells were defined around the nuclei. The limits of the cells in those regions were then defined by a local dynamic threshold operation on the same region in the fluorescent antibody image. A sequence of erosions and dilations was used to separate slightly touching cells and a set of cytoplasm morphological descriptors was used to identify single cells. The area of the individual cells was tabulated in order to define the distribution of cell sizes for comparison with size data from normal and hypertrophic cells.

Responses from entire 96-well plates (measured as average cytoplasmic area/cell) were analyzed by the above methods, and the results demonstrated that the assay performs the same on a well-to-well, plate-to-plate, and day-to-day basis (below a 15% cov for maximum signal). The data showed very good correlation for each day and no variability due to well position in the plate.

The following morphological features can be computed for the field based on individual cell measurements:

1. Aggregate whole nucleus area: the number of nonzero pixels in the nuclear mask;
2. Average whole nucleus area: the aggregate whole nucleus area divided by the total number of nuclei;
3. Total cytoplasmic area: the count of nonzero pixels in the cytoplasmic mask;
4. Aggregate cytoplasm intensity: the sum of the intensities of all pixels in the cytoplasmic mask;
5. Cytoplasmic area per nucleus: the total cytoplasmic area divided by the total nucleus count;
6. Cytoplasmic intensity per nucleus: the aggregate cytoplasm intensity divided by the total nucleus count;
7. Average cytoplasmic intensity: the aggregate cytoplasm intensity divided by the cytoplasmic area; and
8. Cytoplasm nucleus ratio: the total cytoplasmic area divided by the total nucleus area.

Additionally, one or more fluorescent antibodies to other cellular proteins, such as actin or myosin, can be included. Images of these additional labeled proteins can be acquired and stored with the above images, to identify anomalies in the distribution and morphology of these proteins in hypertrophic cells. This example of a multi-parametric screen allows for simultaneous analysis of cellular hypertrophy and changes in actin or myosin distribution.

One of skill in the art will recognize that while the example analyzes hypertrophy, the method described can be applied to analyzing general morphological changes in any cell type.

Cell Spreading

Cell attachment is a measure of binding of cell surface receptors to specific ligands on a substrate. The number of cells attached is a measure of the binding potency of these receptors to immobilized ligand. Cell spreading after attachment can be used as a measure of the cellular response to activation of cell surface receptors, and depends on the functional response of the cytoskeletal-based machinery that controls cell shape. Spreading is proportional to the ligand concentration or to the concentration of compounds that modify (positively or negatively) receptor-ligand function. The area of cells that have spread is a measure of the efficacy of surface receptor binding on cell spreading. An assay that measures cell spreading can thus help eliminate lead candidates that bind to a cell receptor with little effect on cell function. Such functional cell assays more accurately predict drug activity in animal and human trials, and thus significantly accelerate the drug development process.

Identifying compounds that affect cell spreading can measure both the potency and efficacy of drugs for a number of therapeutic areas, including but not limited to tumor growth and metastasis; angiogenesis; thrombosis; restenosis; vascular overgrowth during macular degeneration; foam cell formation; inflammatory diseases including but not limited to rheumatoid arthritis, inflammatory bowel disease, multiple sclerosis, psoriasis and asthma; wound healing and scar reduction; and neurodegenerative diseases. Therefore, the development of cell-based assays that provide information on the effect of a test compound on cell spreading is an important goal for drug discovery.

Thus, the present invention also provides automated methods for analysis of cell spreading, as well as associated software for carrying out the automated assays on a cell screening system. This cell-based assay provides a measure of the efficacy of test compounds to inhibit or promote cell spreading, and also provides information on the kinetics of cell spreading.

In one embodiment, the automated cell spreading method comprises providing an array of cell locations that possess at least a first luminescent reporter that specifically identifies cell cytoplasm, as described above for cell hypertrophy analysis. The cells are contacted with a test stimulus, and then scanned to acquire a cytoplasmic image. The cytoplasmic image is used to create a cytoplasmic mask, in which cytoplasmic objects are identified. Various cell-based morphological features can then be automatically calculated, including cell area, cell perimeter, cell shape, cell aggregate intensity, and cell average intensity. These morphological features provide a measure of the effect of the test stimulus on cell spreading.

As used herein, the phrase "the cells possess one or more luminescent reporter molecules" means that the luminescent reporter molecule may be expressed as a luminescent reporter molecule by the cells, added to the cells as a luminescent reporter molecule, or luminescently labeled by contacting the cell with a luminescently labeled molecule that binds to the reporter molecule, such as a dye or antibody.

The test stimulus can be of any nature, including chemical compounds, drug candidates, environmental samples, or any other stimulus that might modulate cell spreading, whether by promoting or inhibiting cell spreading.

In a preferred embodiment, the first luminescent reporter molecule comprises a fluorescent compound that binds to actin microfilaments, including but not limited to rhodamine-phalloidin.

Descriptions of the various morphological features that can be determined by this method are provided below. For example, cell shape can be analyzed by calculating morphological features including, but not limited to cell box-fill ratio, height-width ratio, cytoplasm maximum width, cytoplasm minimum width, cell roundness, cell P2A, and cytoplasm aspect ratio. Each of these morphological features is explained in more detail below.

This embodiment provides for automated, cell-based morphological measures of cell spreading using a single channel assay. As used herein, the term "cell-based" means that the calculations are determined on an individual cell basis.

In a further embodiment, various field-based (i.e.: calculations determined for the field being viewed) or well-based (i.e.: calculations determined for the well that is currently being analyzed) morphological measures can also be determined, including but not limited to a number of cytoplasmic objects in the field or well; an average of any of the cell-based morphological features in the field or well; and a percentage of cells with any of the cell-based morphological features above a threshold value.

Preferred field-based or well-based morphological features comprise one or more member selected from the group consisting of:

a) a percentage of cells with a cytoplasmic area above a threshold value;
b) a percentage of cells with a perimeter above a threshold value; and
c) a percentage of cells with a P2A above a threshold value.

The cell spreading assay of the present invention can be used in conjunction with cells attached to a substrate via any method, and preferably to substrates that are derivatized to present cell surface receptor ligands on the substrate surface for interaction with cells that possess the appropriate cell surface receptor. The spreading of cells is a function of the ligands and cell receptors that are employed. Cells plated on different immobilized ligands will selectively bind to matched cell surface receptors, and thus homogenous or heterogenous cell poulations can be used for plating. Such cell surface receptor ligands can be of any type that provide for adherence of the desired cell type (and cell surface receptor cell type) to the substrate. For example, extracellular matrix proteins will promote binding to matched adhesion molecules of the integrin family. Alternately, such extracellular matrix proteins or small molecule mimmetics could be introduced in solution to bind to cells and affect cell attachment and spreading. For example, analogs of the extracellular matrix protein fibronectin that contain the RGD amino acid sequence act as antagonists to block fibronectin signaling and will prevent cell spreading. The antagonist effect is only seen if the ligands are soluble and monovalent when added to cells. Ligands pre-attached to a support structure such as beads would have a similar effect on cell spreading as ligands that are bound to the cell substrate.

The substrate can be patterned with various cell surface receptor ligands, in order to analyze the effect of test compounds to inhibit cell spreading of more than one cell type, or to anlyze the effect of test compounds on cell spreading caused by the interaction of different ligand-cell surface receptor pairs. In a further preferred embodiment, a control compound known to effect cell spreading is contacted with the adhered cells, and then the cells are further contacted with a test compound, to determine the effect of the test compound on the control compound's cell spreading modulation. Examples of compounds known to affect cell spreading are receptor ligands such as extracellular matrix proteins, antagonists such as integrin- or proteoglycan-blocking antibodies, signaling inhibitors such as kinase inhibitors including phosphatidyl inositol-3 kinase inhibitors, cytoskeletal inhibitors such as cytochalasin D, soluble receptor ligands and their antagonists, including growth factors, autocoids, hormones, and chemokines, transcriptional activators and repressors and many other drug classes directed against pharmacological targets of importance to cell morphogenesis.

Cells that are allowed to spread for 1–2 days establish a steady-state morphology that is characteristic of the cell type and its environment. Evaluating the effects of drugs on the steady state morphology of each cell type thus requires morphological characterization for each cell type. Furthermore, the steady-state shape of cells is determined by many variables, and not just cell spreading after attachment to the substrate.

In contrast, most cells have a rounded shape that increases in diameter as cells attach and spread shortly after plating. This pattern is similar for all cells during the initial stages of cell spreading. Furthermore, pharmacological modification of molecules involved in cell spreading have a greater effect on the early kinetics of spreading than on the final extent of spreading during the day following plating. Since cells remain symmetric during the initial phase of spreading, cell area is more sensitive to spreading rates than is cell shape. Therefore, in a preferred embodiment, cell spreading is analyzed shortly after plating the cells, although the methods can also be used to analyze steady state cell morphology.

In a preferred embodiment, the cells to be analyzed further possess at least a second luminescent reporter molecules to identify individual cells in the population by the presence of a bright luminescent spot, scanning multiple cells in each of the locations to acquire a spot image from the second luminescent reporter molecule, creating a spot mask from the spot image, and using the spot mask and the cytoplasmic mask to automatically calculate one or more morphological features that provide a measure of cell spreading.

In a preferred embodiment, the second luminescent reporter specifically detects nuclei, a nuclear image is obtained, and a nuclear mask is generated. Other reporter molecules that produce a bright spot within each cell that can be segmented from nearby cells, including but not limited to markers specific for intracellular components such as the Golgi apparatus and endocytic compartments, can also be used as the first luminescent reporter molecule.

In this embodiment, similar cell-based morphological features indicative of cell spreading can be calculated as for the single channel embodiment above, in addition to nuclear area, nuclear count, cytoplasm area minus nuclear area, and cell area divided by nuclear area. Furthermore, cell area features can be calculated on a per nuclei basis, in addition to on a per cytoplasm basis. Similar field-based and/or well-based morphological features can also be calculated as for the single channel, in addition to a number of nuclear objects in the field or well, a percentage of cells with a nuclear area above a threshold value and a percentage of cells with a cytoplasmic minus nuclear area above a threshold value.

In a preferred embodiment, the method further comprised automatically determining one or both of a number of spot objects in each cytoplasmic object; and a specific cytoplasmic object that each spot object is located on. In this embodiment, the nuclear mask can be used to calculate morphological data from the nucleus objects, including the number of nuclei and the nuclear area (see below for further details), and the cytoplasmic mask can be used to calculate the number of labeled cytoplasmic objects. The nuclear and cytoplasmic masks are then compared to determine one or more of the following (1) the number of nucleus channel local maxima in each cytoplasmic object; and/or (2) a "matching vector" specifying which cytoplasmic object each nucleus object is located on.

Those cytoplasmic objects that are identified as distinct may contain one or more nucleus ("nucleus object") within the area defined by the cytoplasmic object. Such nucleus objects may be colonies of cells instead of single cells, which can be accounted for by adjusting the maximum number of nucleus objects in a valid cytoplasmic object. This parameter can be set to 1 (i.e.: all objects studied will be single cells) if mono-disperse cells are plentiful in the images or if analysis of only single cells is desired. Otherwise, the parameter can be set higher, and the size and/or morphology of colonies can also be analyzed by this approach.

Cells touching the edge of the field of view can optionally be excluded, since their area and shape measurements may be incomplete. Cells that are in large clumps can also be excluded if desired. The morphology of clumps depends on cell-cell contact more than cell-substrate contact, while single cells and small colonies are more dependent on cell-substrate adhesion. Thus, the method allows a user to select cell subpopulations that will report more selectively on agents that affect spreading of cells on defined substrates.

The cell spreading assay processes the nuclear and cytoplasmic images to generate nuclear and cytoplasmic masks and single cell data is generated from the masks and raw images. Processing of the nuclear and cytoplasmic images optionally includes an initial background compensation step, involving the removal of small bright spots and gradual variations in background across the field. Further processing of the nuclear and cytoplasmic images comprises the creation of the nuclear mask and the cytoplasmic mask.

Creation of the nuclear mask can be performed by a variety of methods. In one embodiment, the nuclear mask is created by the local maximal method of identifying nuclei, which usually includes a smoothing step to remove artificial maxima caused by image noise. Nuclear pixels are then examined and those brighter or equal to all of their neighbors are tentative local maxima. Contiguous pixels selected in this way are fused together into a single local maximum, which allows segmentation of nuclei that are closely apposed and can be adapted to identify other cell markers, such as the intracellular compartments mentioned above. The second method for creating the nuclear mask is the nuclear objects method, which considers whole nuclei as single nuclear objects and local variations are not used to segment nearby objects in the nuclear image. The nuclear objects method is appropriate for nuclei that are discrete and rarely touch nuclei from other cells.

The cytoplasmic image is used to identify contiguous objects (cells or colonies of cells) that are labeled with the cytoplasmic reporter molecule and to produce a cytoplasmic mask.

The following provides a detailed description of the various cell-based and field- or well-based morphological features that can be calculated using the methods of the invention:

CELL-BASED FEATURES a) Cell Area: Area of the cell/colony, including nuclei, divided by the number of nuclei, determined by the number of pixels in the cell (or colony of cells). Pixels are picture elements of the digitized image and have units of area, referenced to the image not the sample. Each pixel has dimensions defined as fractions of the frame height and width, and has a spot intensity. Pixel sizes depend on the microscope magnification, the size of the imaging chip in the camera, and the number of pixels in the resulting image.

b) Cell Perimeter: The length of the border of the cell or cell colony, in pixels.

c) Cell P2A: the cell or cell colony perimeter (P) squared, divided by ($4\pi$ times the cell area). This is a measure of the deviation of the object from roundness. A perfect circle is 1.0, and the value increases with deviation from roundness. P2A is a scale-independent measure of cell shape. Compared to Roundness (see below), this measure is more sensitive to local irregularities in the perimeter.

d) Cell BFR: The "box fill ratio" of a cytoplasmic object. This shape measure is used to exclude highly concave objects from analysis. In a preferred embodiment, the BFR is the ratio of the area of the cell or cell colony to the area of the best fit bounding box. The best fitting bounding box is determined for each cytoplasmic object by rotating a frame around each cytoplasmic object and choosing the box with minimized area. Rectangular objects have a BFR value of 1.0 while irregular objects have lower values.

e) Cell HWR: The "height width ratio" of a cell. This shape measure is used to exclude highly elongated objects from analysis. In a preferred embodiment, the Height Width Ratio is the ratio of the length of the cell/colony to the width of the cell or cell colony. In a preferred embodiment, the bounding box of the cell (a rectangular box that circumscribes the object with sides parallel to the image frame, rather then the best fit bounding box) is determined, and its longer dimension is divided by its shorter dimension. Fairly round objects will have a HWR value close to 1.0.

f) Cell aggregate intensity: The sum of all the pixel intensities in the cell or cytoplasmic object.

g) Cell average intensity: The Cell aggregate intensity (pixel intensity in the cytoplasm channel) divided by the cell area.

h) Nuc area: The total area of all the Nucleus channel objects in the cytoplasmic object (cells or colonies of cells) divided by the number of nuclei.

i) Nuc count: The number of valid Nucleus channel objects in the cytoplasmic object as determined by the nucleus object method.

j) Nuc spot count: The number of nuclei in the cell as measured by the local maxima method. This is preferably measured by blurring the nucleus channel image, and then counting its local maxima.

k) Cyto minus Nuc area: Area of the cell/colony excluding nuclei, which is preferably determined by subtracting the nuclear area from the cell area. This cell feature can be used to calculate the well feature "Avg Cytoplasm Area"

l) Cyto Nuc Area Ratio: The Cell Area divided by the Nuc area.

m) Cyto Max Width: The longer dimension of the best fit bounding box.

n) Cyto Min Width: The shorter dimension of the best fit bounding box.

o) Cyto Roundness: (4×Cell Area)/($\pi$ times Cyto Max Width). This will be 1.0 for perfectly round objects, and will be lower to the degree that the object is elongated. Compared to P2A, this measurement is less sensitive to local irregularities in the perimeter. A more-or-less circular object with a wobbly perimeter will be close to 1.0 with roundness, but not with P2A. Roundness is a scale-independent measure of cell shape.

p) Cyto Aspect Ratio: Cyto Max Width/Cyto Min Width (i.e.: the height to width ratio of the cell or cell colony).

WELL OR FIELD-BASED FEATURES

A % Cytoplasmic area above threshold: Percentage of cells/colonies with "Avg Cytoplasm Area" (excluding the nucleus) above a user-set threshold value.

B Cyto minus nuc area averages Field or well average area of the cell/colony excluding nuclei.

C Percent Cell Perimeter above threshold: Percentage of cells/colonies in the cell channel with perimeter above a user-set threshold value. This feature is most useful for mono-disperse cells.

D Average cell perimeter: The average length of the border of the cell colony in pixels.

E Cytoplasmic area average The well average of "Cyto Minus Nuc Area"=area of the cell/colony minus the area of nuclei within the object normalized by the number of nuclei in the colony.

F Percent P2A above threshold: Percentage of cells in the field or well with P2A above threshold.

G P2A average: Average cell P2A in the field or well.

H Percent cytoplasmic or nucleus area above threshold: Percentage of cells with cytoplasmic area above threshold, and/or with nuclear area above threshold I Cyto/nuc area averages J Percent Cyto Aspect Ratio above threshold: Percentage of cells with Cyto Aspect Ratio above threshold K Cyto Aspect Ratio average: Average cell Cyto Aspect Ratio in the field or well L Number of nuclei M Nucleus area average N Number of cytoplasmic objects: Total number of cells/colonies per well identified in the cytoplasm channel O Field count: Number of fields acquired for the well P Percent of Cells Analyzed: Number of distinct cells/colonies that are considered valid for further measurement. Cells may be excluded if they touch edges or if the number of cells/colony is larger than the user-defined maximum.

Q. Average Cells per Field: Total number of identified cells/colonies divided by the number of fields imaged R. Standard Deviation of the above averages S. Coefficient of Variance of the above averages A powerful feature of the Cell Spreading assay is the ability to measure the fraction of responding cells as well as the average response of the cell population. This is achieved by use of a user defined threshold value for each output cell feature. In practice, the fraction of responding cells determined by appropriate thresholding will increase the assay window (the ratio between the maximum and minimum value of the output feature) and reduce standard deviations dramatically, thus providing enhanced value to the user of the assay. In the case of cell spreading, as suspended cells attach and spread, the cell population heterogeneity increases because subsets of cells lag behind and remain round. The heterogeneity alters mean values and disproportionately increases the variance of raw cell features (area, P2A, aspect ratio, etc.). An alternate to the mean value of these cell features is the percentage of cells with features above a threshold value. For example, the average size of spreading cells can be measured, or the number of cells in the spread and rounded populations can be measured, to indicate the population shift from round to spread morphology. Measuring the fraction of total cells that are spread is especially useful if the population of cells is bimodal, with some cells remaining small. In general the thresholded output features have units of number of cells and refer to the number of cells that respond to stimuli. The number of responding cells (eg, % cells with area above a threshold value) is a separate measure of the population behavior to drug treatment and is distinct from the primary measure of cell response (eg., average area of the cells).

In addition, the parameters are adjustable to allow customization of the assay to match biological samples and conditions. For example, the minimum and maximum thresholds and/or the range of possible values, can be modified for any of the input or output parameters.

In all of these embodiment, the cytoplasmic object can be a cell or a colony of cells, and thus the method provides for analyzing the effects of test stimuli on aggregate cell spreading in cell colonies.

Furthermore, each of these embodiment can be used to analyze the effect of a test compound on cell spreading associated with a condition selected from the group consisting of tumor growth and metastasis, angiogenesis, thrombosis, restenosis, vascular overgrowth during macular degeneration, foam cell formation, inflammatory diseases, wound healing, scar reduction, and neurodegenerative diseases.

The invention further provides a computer readable storage medium comprising a program containing a set of instructions for causing a cell screening system to execute the methods of the invention. As used herein, computer readable media include, but are not limited to, magnetic disks, optical disks, organic memory, and any other volatile (e.g., Random Access Memory ("RAM")) or non-volatile (e.g., Read-Only Memory ("ROM")) mass storage system readable by a the processing unit of a computer. The computer readable medium includes cooperating or interconnected computer readable medium, which exist exclusively on a processing system or be distributed among multiple interconnected processing systems that may be local or remote to the processing system.

Cell Spreading Assay Preferred Embodiment

In a preferred embodiment (See FIGS. 25A–25E), the adequacy of the image set for analysis is tested by measuring the overall contrast in the image (102), and checking the result against a user-specified value (103, Min Dynamic Threshold). If the images fail this test, they are rejected and another field is acquired and analyzed instead. The nucleus channel image is blurred with a square convolution kernel of size set by the user (Nucleus Kernel), creating the Blurred Nuc Image. Then background correction (105) is applied to that image with the following pixelwise computation. A positive constant is added, and the average intensity in a square area centered on the pixel is subtracted. The size of this square is set by the user (Background Kernel). The Filtered Nuc Image is produced. A similar Background Correction (106) is applied to the raw Cytoplasm Image to produce the Filtered Cyto Image. The kernel size is the same as in step 105.

The Filtered Nuc Image is then thresholded (107) to create the binary Preliminary Nuc Mask Image. The method for determining the threshold is either a value supplied by the user (fixed threshold), or a value computed automatically by the Isodata Method. The Filtered Cyto Image is then thresholded (108) to create the Preliminary Cyto Mask Image. The method for determining the threshold is either a value supplied by the user (fixed threshold), or a value computed automatically by either the Isodata Method or the Triangulation (peak interpolation) method.

The Preliminary Nuc Image is then subjected to a morphologic opening (109, an erosion followed by a dilation) to remove tiny objects which represent noise in the original image. The size of the structuring element for the opening is a fixed value. The output of this step is then subjected to a morphologic closing (109, a dilation followed by an erosion) to fill tiny holes in the nuclei, also caused by image noise. The size of the structuring element for the closing is a fixed value. The output from this step is the Nuc Mask Image.

The Preliminary Cyto Mask Image is then subjected to a morphologic opening (110) to remove tiny objects. The size of the structuring element for the opening is a fixed value. The output from this step is the Cyto Mask Image. The Nuc Mask Image is subtracted from the Cyto Mask image (111) to produce the Net Cyto Mask Image. This represents the area of the cytoplasm.

The Cyto Mask Image is further processed to fill in artifactual holes in the cells (201). These holes may appear as follows: actin is not uniformly distributed in cells, with a higher concentration present at the periphery. When the Cyto channel is stained for actin (for example, with Phalloidin) the cells are dimly labeled in their interiors, and may exhibit these holes after the segmentation step. In the Cyto mask, bright pixels are inside cells, while dark (intensity zero) cells are either outside cells or in the artifactual holes within cells. All intensity zero pixels which are connected to the edges of the image through a sequence of intensity zero pixels are labeled by "conditional dilation," the process of recursively labeling qualified pixels based on their adjacency to previously labeled pixels. A mask of such exterior pixels is created and its intensities are inverted, resulting in a Cyto Mask Image in which there are no interior holes in cells.

The Cyto Mask Image is then optionally (controlled by the user, 202) processed to remove cells touching the edge of the image (203). To do this, first a Preliminary Border Mask is created in which the edge pixels are bright and the rest are dark (301). That mask is then dilated to a thickness of three pixels (302) to create the Border Mask Image. The Border Mask Image is then conditionally dilated (303) through the Cyto Mask Image. This recursively labels bright pixels of the Cyto Mask image which are contiguous with bright pixels in the Border Mask Image, and produces the Edge Object Mask. The Edge Object Mask is Exclusively Or'ed with the Cyto Mask Image (304), removing the edge touching objects.

The objects in the Nuc Mask Image are then labeled (204), producing the Labeled Nuc Mask Image. All the bright pixels in the Nuc Mask Image are subdivided into separate, contiguous objects. Each object is assigned an object number. For each pixel in the object, the corresponding pixel in the Labeled Nuc Mask Image is assigned an intensity value equal to the object number. The objects in the Cyto Mask Image are then labeled (205) producing the Labeled Cyto Mask Image. The total number of Cells found is added to the Total Cell Count for the current well (206).

Then the Nucleus channel objects are matched up with Cyto channel objects. This makes it possible to reject artifacts (apparent cells with no nucleus, or apparent nuclei with no cell). It also counts the number of nuclei in a Cyto channel object, determining whether the object is a colony, and to limit the size (in terms of number of cells present) of a colony that will be analyzed. To do the matchup, each Nuc object is analyzed in turn (401). The mask of the current Nuc object is extracted (402) from the Labeled Nuc Mask into the Current Object Mask. This mask is used to define an area in the Labeled Cyto Mask in which the histogram is taken. The bins of the histogram correspond to the numbers of the objects in the Labeled Cyto Mask. A nucleus is required to be in exactly one cell/colony, so if no bin, or more than one bin, has a nonzero value, the nucleus is rejected (404). Otherwise, the nucleus is considered to be in the cell corresponding to the index of the one nonzero bin, and the count of nuclei in the corresponding cell is incremented (405). Also, the aggregate area of the nuclei in the corresponding cell is incremented by the area of the nucleus (406).

Then the Cyto objects are analyzed, testing their validity and measuring their features (501). First, the area of the Cyto object and the number of nuclei in it are compared to the user defined limits (and to the fixed requirement that there be at least one nucleus). If the requirements are not met, the Cyto object is rejected (502). If the requirements are met, the mask of the object is extracted from the Labeled Cyto Mask into the Single Cyto Object Mask (503). The Net Cyto Area of the object is determined by measuring the number of nonzero pixels in the Net Cyto Mask Image which correspond to nonzero pixels in the Single Cyto Object Mask (504).

Then the region of interest (ROI), a small rectangular area which encloses the object and a small margin around it, is cut out from the Raw Cyto Image and the Single Object Cyto Mask (505) into the ROI images. This step is not essential, but the following analyses are significantly faster using the smaller images. The perimeter, area, and the best fit bounding box (smallest rectangle which can be fit around the object) are determined (506).

Several statistics are then computed which determine the validity of the Cyto object. The aspect ratio (height/width) of the best fit bounding box, the Box Fill Ratio (BFR, the area of the Cyto object divided by the area of the best fit bounding box), and the Normalized P2A (perimeter squared divided by four pi times the object area) are computed and compared to limits set by the user (507). If any of these falls outside the limits, the Cyto object is rejected. Otherwise, the remaining Cell Features are computed and stored in the database.

In a further aspect, the invention further provides computer readable media for causing a cell screening system to carry out the methods of the invention. As used herein, computer readable media include magnetic disks, optical disks, organic memory, and any other volatile (e.g., Random Access Memory ("RAM")) or non-volatile (e.g., Read-Only Memory ("ROM")) mass storage system readable by the central processing units of a computer. The computer readable medium includes cooperating or interconnected computer readable medium, which exist exclusively on the processing system or be distributed among multiple interconnected processing systems that may be local or remote to the processing system.

Validation Data

The ability of the Cell Spreading assay to measure intermediate values via the threshold parameter, % Cyto-nuc area above threshold, was tested by analyzing the spreading of cells in the presence of increasing concentrations of a control compound. For cell spreading, the fraction of cells above threshold value for the cytoplasmic area minus the nuclear area (% Cyto-nuc area>thresh) was demonstrated to be the most sensitive cell feature. Thresholding also has the potential to minimize the graded response and to artificially produce a step function at increasing stimuli. However, we found that smooth, continuous dose response curves are produced when cells are measured with thresholded cell features.

Compounds that interfere with metastasis of prostate carcinoma cells were screened as follows. PC3 human prostate carcinoma cells (ATCC # CRL 1435) were cultured in media with appropriate stimulants and passaged to collagen coated 96 well plates. Similar experiments were also conducted with MDA-MB231, a breast carcinoma cell line (ATCC # HTB-26), A549 human lung carcinoma cell line (ATCC # CCL 185), and primary HMVEC-d human skin microvessel endothelial cells (Clonetics Walkersville, Md.

Conditions in which cell spreading could be augmented or diminished were tested in various ways, including plating the cells on collagen coated (various concentrations) or collagen free substrates, varying the time of cell spreading prior to analysis, and plating cells in the presence of chemical modulators. After two hours, cells were fixed and stained with ALEXA™ 488 phalloidin (Molecular Probes) and Hoechst 33342 as per the protocol for cellular hypertrophy. The size of cells under these various conditions, as measured by cytoplasmic staining, was distinguished from background levels. The number of cells per field was determined by measuring the number of nuclei stained with the Hoechst DNA dye. The area per cell was found by dividing the cytoplasmic area (phalloidin image) by the cell number (Hoechst image).

Results

These preliminary assays demonstrated the following:

(1) Spreading was strongly dependent on the substrate coatings. Increasing collagen concentration sped cell spreading and reduced the heterogeneity of cell morphology during spreading. PC-3 cell spreading was much slower on collagen free substrates and so collagen-free substrates may be used as a negative control for cell spreading at 2–3 hours. On tissue culture plastic, PC-3 cells became fully spread between 6 to 12 hours, while on a defined collagen I matrix, cell spreading was achieved between 2 and 3 hours.

(2) Cell area provided a measure of the ligand-induced degree of cell spreading in this assay. The size of cells was proportional to the ligand-receptor function. Since the area is determined by ligand concentration and by the resultant function of the cell, drug efficacy, as well as drug potency, can be determined by this assay.

(3) The method can be used to distinguish between compounds that modify cell attachment (thus reducing the number of cells per well) from compounds that modify cell spreading after attachment (thus not reducing the number of cells per well). For example, EDTA (50 mM) inhibited cell spreading of PC-3 cells, but also inhibited cell adherence, preventing further processing and staining.

In contrast, the actin depolymerizing agent, cytochalasin D, did not affect binding of cells to the substrate but prevented their spreading on various substrates. We have determined that cytochalasin D provides an important negative control compound since it blocks spreading, not adhesion. In addition, cytochalasin D is selective for inhibiting spreading, without strong effects on other cell functions, including cell motility.

To illustrate how cell spreading is a unique functional event that can be distinguished from attachment and motility by drug effects, we performed the following experiments. A549 cancer cells were allowed to spread on a collagen I coated substrate for 3 hours, and then were fixed and stained with rhodamine phalloidin. The number of cells that spread beyond a selectable threshold area was measured as a function of increasing concentrations of cytochalasin D. While cells normally spread to a size much larger than the nucleus in this time interval, cytochalasin D maintained cells in a tight rounded morphology not much larger than the nucleus. The movement of A549 cells was measured at 18 hours after plating. At a concentration of 0.5 $\mu$M, cytochalasin D prevented spreading of 80% of cells but permitted movement of 70% of cells. Cytochalasin had no effect on adhesion to the substrate as measured by the number of cells that remain attached after a 3 hour incubation.

The spreading of cells is a function of the ligands and cell receptors that are employed, and plating cells on different immobilized ligands will selectively bind to matched cell surface receptors. A549 cells were plated on various matrix proteins and allowed to spread for 3 and for 5 hours. Cell spreading was complete by 3 hours on all collagen I, collagen IV and laminin, but was incomplete on fibronectin. Thus ligand-dependent differences in the kinetics of cell spreading can be measured. In addition, strong differences in the activation of spreading were seen on different matrices. Laminin strongly inhibited the spreading of A549 cells compared to other matrix proteins. In contrast to spreading, cell motility presented a very different biological profile of these matrix proteins. Laminin maximally stimulated movement while minimally stimulating spreading. Fibronectin maximally stimulated spreading, while minimally stimulated movement. Collagen I maximally stimulated both movement and spreading. In further experiments, cells were allowed to spread in the presence of various kinase inhibitors and the effect on cell spreading was determined. The kinase inhibitors included 10 $\mu$M Calphostin C (a protein kinase C inhibitor), 10 $\mu$M KN-52 (a Calmodulin dependent protein kinase inhibitor), 10 $\mu$M genistein (a tyrosine kinase inhibitor) and 10 nM wortmannin (a phosphatidyl inositol kinase inhibitor. These agents were also applied during measurement of cell motility. The cell spreading assay provided a unique biological profile that was different from the profile for cell motility. Calphostin C, for example, was equally effective at inhibiting cell spreading and movement, genistein and KN-62 were ineffective at the concentrations used at blocking either cellular response, and Wortmannin was more effectve at blocking spreading that cell motility.

These results serve to emphasize that cell spreading is a biological function distinct from cell movement, and provides a unique bioprofile of native ligands and their antagonists. Application of the cell spreading assay in conjunction with other assays, such as cell motility assays, will provide multiparametric profiling to better describe drug efficacy and specificity.

(4) The best primary output feature in terms of producing a high signal to background ratio and Z window values was cytoplasmic area minus nuclear area (Cyto-nuc area avg), which measures the cytoplasmic area of each cell and subtracts the area of the cell's nucleus. Other parameters such as average cell area (Cyto area avg), and the ratio between cytoplasmic and nuclear areas (Cyto/nuc area avg) gave reasonable Z windows, but the signal to background levels were considerably lower than those for Cyto-nuc area avg. For cell spreading, the shape derived features, P2A average, and Asp Ratio average were less useful than the area features. This is a consequence of the biological design of the assay. Cell spreading was measured during the initial phase, when cells were still quite symmetric, and thus exhibited no change in normalized perimeter or aspect ratio. However, pharmacological modification of molecules involved in cell spreading had a far greater effect on the early kinetics of spreading than on the final extent of spreading.

(5) Phalloidin conjugates containing either Alexa-488 or rhodamine were compared in terms of signal production on the cell screening system. Although Alexa-488 phalloidin needed shorter exposure times, the signal to noise was poor, resulting in lower contrast images. Rhodamine phalloidin needed longer exposures than Alexa 488, but the signal to noise levels were much higher. Permeabilization with 0.1% vs. 0.5% Triton X-100 had no effect on exposure times.

(6) High concentrations of DMSO had significant effects on PC-3 cell spreading. Cells were seeded onto type I collagen in the presence of increasing amounts of DMSO, allowed to spread for 3 hours, and analyzed by determining the percentage of cells with Cyto minus NucArea above threshold as the output. DMSO at concentrations of 5% and 2.5% significantly reduced the ability of PC-3 cells to spread on collagen while DMSO at or below 1% had no effect.

EXAMPLE 3

Dual Mode High Throughput and High-Content Screen

The following example is a screen for activation of a G-protein coupled receptor (GPCR) as detected by the translocation of the GPCR from the plasma membrane to a proximal nuclear location. This example illustrates how a high throughput screen can be coupled with a high-content screen in the dual mode System for Cell Based Screening.

G-protein coupled receptors are a large class of 7 transmembrane domain cell surface receptors. Ligands for these receptors stimulate a cascade of secondary signals in the cell, which may include, but are not limited to, $Ca^{++}$ transients, cyclic AMP production, inositol triphosphate ($IP_3$) production and phosphorylation. Each of these signals are rapid, occuring in a matter of seconds to minutes, but are also generic. For example, many different GPCRs produce a secondary $Ca^{++}$ signal when activated. Stimulation of a GPCR also results in the transport of that GPCR from the cell surface membrane to an internal, proximal nuclear compartment. This internalization is a much more receptor-specific indicator of activation of a particular receptor than are the secondary signals described above.

Figure 19:
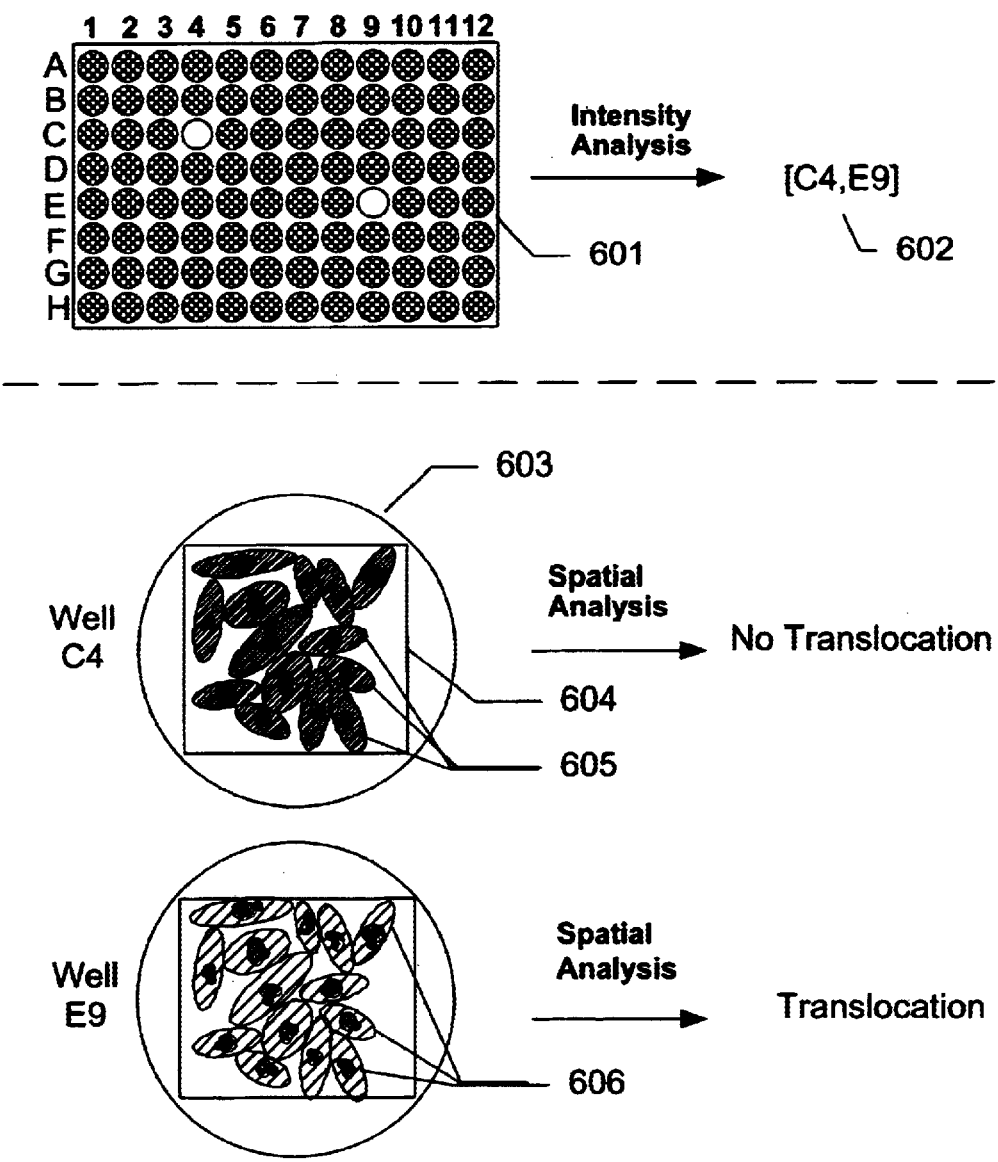
FIG. 19 is an illustration of the data from the High Throughput mode of the System for Cell Based Screening, an example of the data passed to the High Content mode, the data acquired in the high content mode, and the results of the analysis of that data.

FIG. 19 illustrates a dual mode screen for activation of a GPCR. Cells carrying a stable chimera of the GPCR with a blue fluorescent protein (BFP) would be loaded with the acetoxymethylester form of Fluo-3, a cell permeable calcium indicator (green fluorescence) that is trapped in living cells by the hydrolysis of the esters. They would then be deposited into the wells of a microtiter plate 601. The wells would then be treated with an array of test compounds using a fluid delivery system, and a short sequence of Fluo-3 images of the whole microtiter plate would be acquired and analyzed for wells exhibiting a calcium response (i.e., high throughput mode). The images would appear like the illustration of the microtiter plate 601 in FIG. 19. A small number of wells, such as wells C4 and E9 in the illustration, would fluoresce more brightly due to the $Ca^{++}$ released upon stimulation of the receptors. The locations of wells containing compounds that induced a response 602, would then be transferred to the HCS program and the optics switched for detailed cell by cell analysis of the blue fluorescence for evidence of GPCR translocation to the perinuclear region. The bottom of FIG. 19 illustrates the two possible outcomes of the analysis of the high resolution cell data. The camera images a sub-region 604 of the well area 603 producing images of the fluorescent cells 605. In well C4, the uniform distribution of the fluorescence in the cells indicates that the receptor has not internalized, implying that the $Ca^{++}$ response seen was the result of the stimulation of some other signalling system in the cell. The cells in well E9 606 on the other hand, clearly indicate a concentration of the receptor in the perinuclear region clearly indicating the full activation of the receptor. Because only a few hit wells have to be analyzed with high resolution, the overall throughput of the dual mode system can be quite high, comparable to the high throughput system alone.

EXAMPLE 4

Kinetic High Content Screen

The following is an example of a screen to measure the kinetics of internalization of a receptor. As described above, the stimulation of a GPCR, results in the internalization of the receptor, with a time course of about 15 min. Simply detecting the endpoint as internalized or not, may not be sufficient for defining the potency of a compound as a GPCR agonist or antagonist. However, 3 time points at 5 min intervals would provide information not only about potency during the time course of measurement, but would also allow extrapolation of the data to much longer time periods. To perform this assay, the sub-region would be defined as two rows, the sampling interval as 5 minutes and the total number of time points 3. The system would then start by scanning two rows, and then adding reagent to the two rows, establishing the time=0 reference. After reagent addition, the system would again scan the two row sub-region acquiring the first time point data. Since this process would take about 250 seconds, including scanning back to the beginning of the sub-region, the system would wait 50 seconds to begin acquisition of the second time point. Two more cycles would produce the three time points and the system would move on to the second 2 row sub-region. The final two 2-row sub-regions would be scanned to finish all the wells on the plate, resulting in four time points for each well over the whole plate. Although the time points for the wells would be offset slightly relative to time=0, the spacing of the time points would be very close to the required 5 minutes, and the actual acquisition times and results recorded with much greater precision than in a fixed-cell screen.

EXAMPLE 5

High-content Screen of Human Glucocorticoid Receptor Translocation

One class of HCS involves the drug-induced dynamic redistribution of intracellular constituents. The human glucocorticoid receptor (hGR), a single "sensor" in the complex environmental response machinery of the cell, binds steroid molecules that have diffused into the cell. The ligand-receptor complex translocates to the nucleus where transcriptional activation occurs (Htun et al., *Proc. Natl. Acad. Sci.* 93:4845, 1996).

In general, hormone receptors are excellent drug targets because their activity lies at the apex of key intracellular signaling pathways. Therefore, a high-content screen of hGR translocation has distinct advantage over in vitro ligand-receptor binding assays. The availability of up to two more channels of fluorescence in the cell screening system of the present invention permits the screen to contain two additional parameters in parallel, such as other receptors, other distinct targets or other cellular processes.

Plasmid construct. A eukaryotic expression plasmid containing a coding sequence for a green fluorescent protein— human glucocorticoid receptor (GFP-hGR) chimera was prepared using GFP mutants (Palm et al., *Nat. Struct. Biol.* 4:361 (1997). The construct was used to transfect a human cervical carcinoma cell line (HeLa).

Cell preparation and transfection. HeLa cells (ATCC CCL-2) were trypsinized and plated using DMEM containing 5% charcoal/dextran-treated fetal bovine serum (FBS) (HyClone) and 1% penicillin-streptomycin (C-DMEM) 12–24 hours prior to transfection and incubated at 37° C. and 5% $CO_2$. Transfections were performed by calcium phosphate co-precipitation (Graham and Van der Eb, *Virology* 52:456, 1973; Sambrook et al., (1989). *Molecular Cloning: A Laboratory Manual*, Second ed. Cold Spring Harbor Laboratory Press, Cold Spring Harbor, 1989) or with Lipofectamine (Life Technologies, Gaithersburg, Md.). For the calcium phosphate transfections, the medium was replaced, prior to transfection, with DMEM containing 5% charcoal/dextran-treated FBS. Cells were incubated with the calcium phosphate-DNA precipitate for 4–5 hours at 37° C. and 5% $CO_2$, washed 3–4 times with DMEM to remove the precipitate, followed by the addition of C-DMEM.

Lipofectamine transfections were performed in serun-free DMEM without antibiotics according to the manufacturer's instructions (Life Technologies, Gaithersburg, Md.). Following a 2–3 hour incubation with the DNA-liposome complexes, the medium was removed and replaced with C-DMEM. All transfected cells in 96-well microtiter plates were incubated at 33° C. and 5% $CO_2$ for 24–48 hours prior to drug treatment. Experiments were performed with the receptor expressed transiently in HeLa cells.

Dexamethasone induction of GFP-hGR translocation. To obtain receptor-ligand translocation kinetic data, nuclei of transfected cells were first labeled with 5 µg/ml Hoechst 33342 (Molecular Probes) in C-DMEM for 20 minutes at 33° C. and 5% $CO_2$. Cells were washed once in Hank's Balanced Salt Solution (HBSS) followed by the addition of 100 nM dexamethasone in HBSS with 1% charcoal/dextran-treated FBS. To obtain fixed time point dexamethasone titration data, transfected HeLa cells were first washed with DMEM and then incubated at 33° C. and 5% $CO_2$ for 1 h in the presence of 0–1000 nM dexamethasone in DMEM containing 1% charcoal/dextran-treated FBS. Cells were analyzed live or they were rinsed with HBSS, fixed for 15 min with 3.7% formaldehyde in HBSS, stained with Hoechst 33342, and washed before analysis. The intracellular GFP-hGR fluorescence signal was not diminished by this fixation procedure.

Image acquisition and analysis. Kinetic data were collected by acquiring fluorescence image pairs (GFP-hGR and Hoechst 33342-labeled nuclei) from fields of living cells at 1 min intervals for 30 min after the addition of dexamethasone. Likewise, image pairs were obtained from each well of the fixed time point screening plates 1 h after the addition of dexamethasone. In both cases, the image pairs obtained at each time point were used to define nuclear and cytoplasmic regions in each cell. Translocation of GFP-hGR was calculated by dividing the integrated fluorescence intensity of GFP-hGR in the nucleus by the integrated fluorescence intensity of the chimera in the cytoplasm or as a nuclear-cytoplasmic difference of GFP fluorescence. In the fixed time point screen this translocation ratio was calculated from data obtained from at least 200 cells at each concentration of dexamethasone tested. Drug-induced translocation of GFP-hGR from the cytoplasm to the nucleus was therefore correlated with an increase in the translocation ratio.

Figures 20, 20A, 20B:
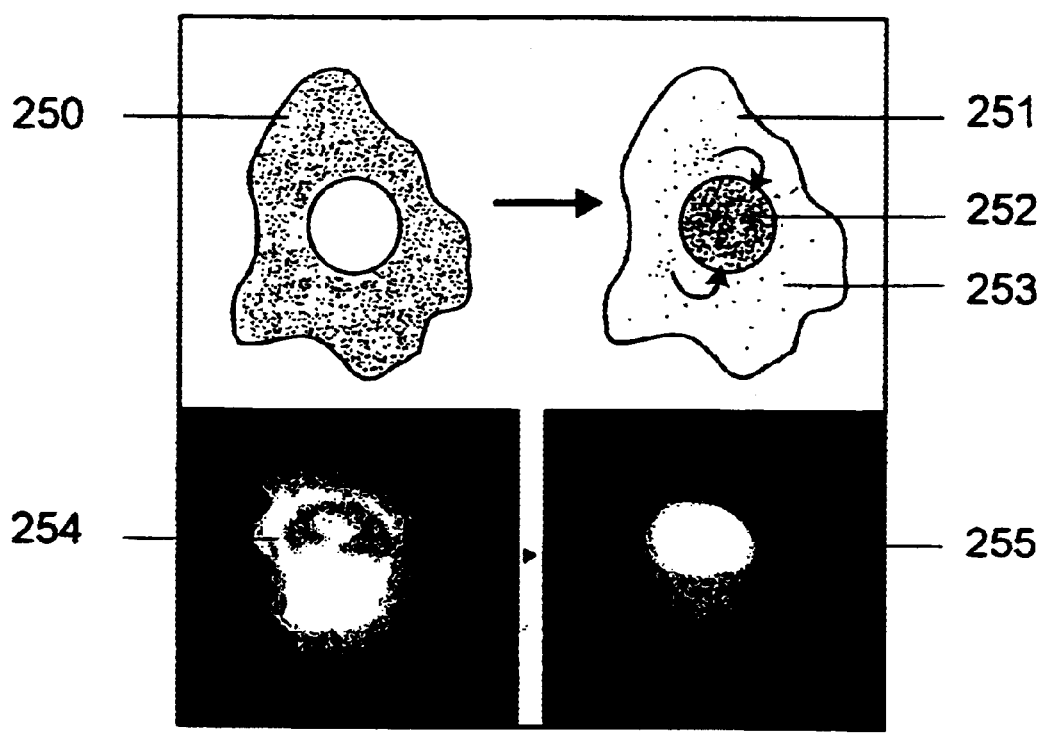
FIG. 20 shows the measurement of a drug-induced cytoplasm to nuclear translocation.

Results. FIG. 20 schematically displays the drug-induced cytoplasm 253 to nucleus 252 translocation of the human glucocorticoid receptor. The upper pair of schematic diagrams depicts the localization of GFP-hGR within the cell before 250 (A) and after 251 (B) stimulation with dexamethasone. Under these experimental conditions, the drug induces a large portion of the cytoplasmic GFP-hGR to translocate into the nucleus. This redistribution is quantified by determining the integrated intensities ratio of the cytoplasmic and nuclear fluorescence in treated 255 and untreated 254 cells. The lower pair of fluorescence micrographs show the dynamic redistribution of GFP-hGR in a single cell, before 254 and after 255 treatment. The HCS is performed on wells containing hundreds to thousands of transfected cells and the translocation is quantified for each cell in the field exhibiting GFP fluorescence. Although the use of a stably transfected cell line would yield the most consistently labeled cells, the heterogeneous levels of GFP-hGR expression induced by transient transfection did not interfere with analysis by the cell screening system of the present invention.

Figure 21:
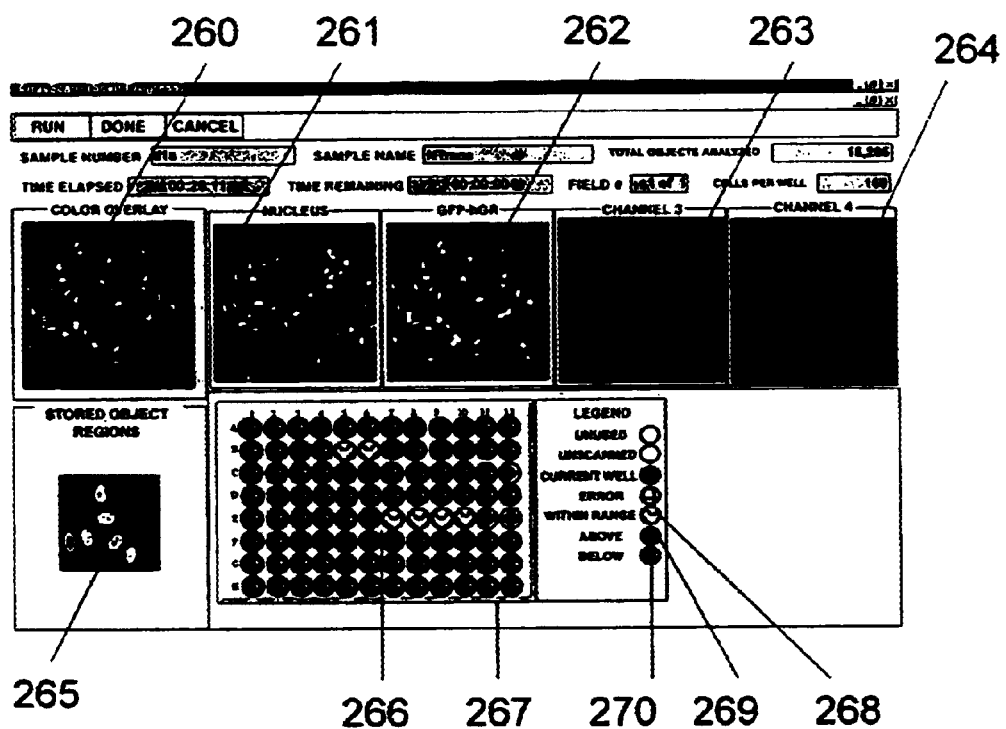
FIG. 21 illustrates a graphical user interface of the measurement shown in FIG. 20.

To execute the screen, the cell screening system scans each well of the plate, images a population of cells in each, and analyzes cells individually. Here, two channels of fluorescence are used to define the cytoplasmic and nuclear distribution of the GFP-hGR within each cell. Depicted in FIG. 21 is the graphical user interface of the cell screening system near the end of a GFP-hGR screen. The user interface depicts the parallel data collection and analysis capability of the system. The windows labeled "Nucleus" 261 and "GFP-hGR" 262 show the pair of fluorescence images being obtained and analyzed in a single field. The window labeled "Color Overlay" 260 is formed by pseudocoloring the above images and merging them so the user can immediately identify cellular changes. Within the "Stored Object Regions" window 265, an image containing each analyzed cell and its neighbors is presented as it is archived. Furthermore, as the HCS data are being collected, they are analyzed, in this case for GFP-hGR translocation, and translated into an immediate "hit" response. The 96 well plate depicted in the lower window of the screen 267 shows which wells have met a set of user-defined screening criteria. For example, a white-colored well 269 indicates that the drug-induced translocation has exceeded a predetermined threshold value of 50%. On the other hand, a black-colored well 270 indicates that the drug being tested induced less than 10% translocation. Gray-colored wells 268 indicate "hits" where the translocation value fell between 10% and 50%. Row "E" on the 96 well plate being analyzed 266 shows a titration with a drug known to activate GFP-hGR translocation, dexamethasone. This example screen used only two fluorescence channels. Two additional channels (Channels 3 263 and 4 264) are available for parallel analysis of other specific targets, cell processes, or cytotoxicity to create multiple parameter screens.

Figure 22:
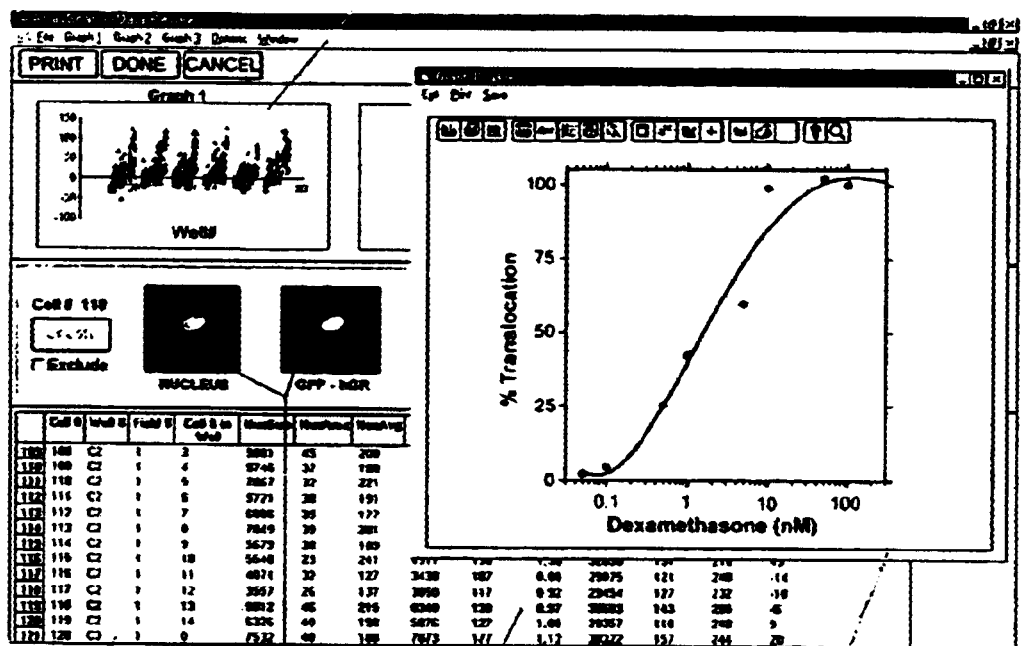
FIG. 22 illustrates a graphical user interface, with data presentation, of the measurement shown in FIG. 20.

There is a link between the image database and the information database that is a powerful tool during the validation process of new screens. At the completion of a screen, the user has total access to image and calculated data (FIG. 22). The comprehensive data analysis package of the cell screening system allows the user to examine HCS data at multiple levels. Images 276 and detailed data in a spread sheet 279 for individual cells can be viewed separately, or summary data can be plotted. For example, the calculated results of a single parameter for each cell in a 96 well plate are shown in the panel labeled Graph 1 275. By selecting a single point in the graph, the user can display the entire data set for a particular cell that is recalled from an existing database. Shown here are the image pair 276 and detailed fluorescence and morphometric data from a single cell (Cell #118, gray line 277). The large graphical insert 278 shows the results of dexamethasone concentration on the translocation of GFP-hGR. Each point is the average of data from at least 200 cells. The calculated $EC_{50}$ for dexamethasone in this assay is 2 nM.

Figure 23:
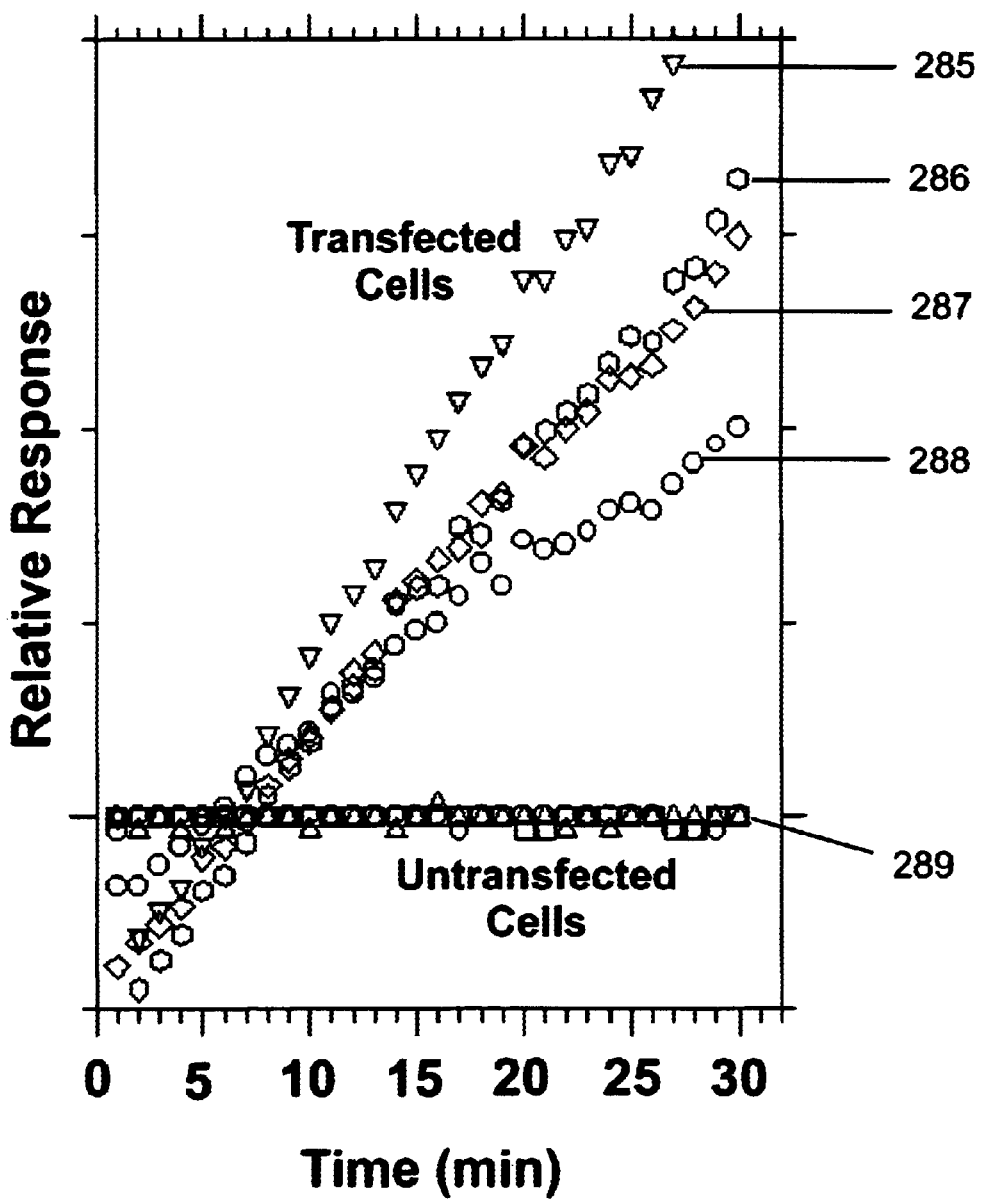
FIG. 23 is a graph representing the kinetic data obtained from the measurements depicted in FIG. 20.

A powerful aspect of HCS with the cell screening system is the capability of kinetic measurements using multicolor fluorescence and morphometric parameters in living cells. Temporal and spatial measurements can be made on single cells within a population of cells in a field. FIG. 23 shows kinetic data for the dexamethasone-induced translocation of GFP-hGR in several cells within a single field. Human HeLa cells transfected with GFP-hGR were treated with 100 nM dexamethasone and the translocation of GFP-hGR was measured over time in a population of single cells. The graph shows the response of transfected cells 285, 286, 287, and 288 and non-transfected cells 289. These data also illustrate the ability to analyze cells with different expression levels.

EXAMPLE 6

High-content Screen of Drug-induced Apoptosis

Apoptosis, is a complex cellular program that involves myriad molecular events and pathways. To understand the mechanisms of drug action on this process, it is essential to measure as many of these events within cells as possible with temporal and spatial resolution. Therefore, an apoptosis screen that requires little cell sample preparation yet provides an automated readout of several apoptosis-related parameters would be ideal. A cell-based assay designed for the cell screening system has been used to simultaneously quantify several of the morphological, organellar, and macromolecular hallmarks of paclitaxel-induced apoptosis.

Cell preparation. The cells chosen for this study were mouse connective tissue fibroblasts (L-929; ATCC CCL-1) and a highly invasive glioblastoma cell line (SNB-19; ATCC CRL-2219) (Welch et al., In Vitro Cell. Dev. Biol. 31:610, 1995). The day before treatment with an apoptosis inducing drug, 3500 cells were placed into each well of a 96-well plate and incubated overnight at 37° C. in a humidified 5% $CO_2$ atmosphere. The following day, the culture medium was removed from each well and replaced with fresh medium containing various concentrations of paclitaxel (0–50 μM) from a 20 mM stock made in DMSO. The maximal concentration of DMSO used in these experiments was 0.25%. The cells were then incubated for 26 h as above. At the end of the paclitaxel treatment period, each well received fresh medium containing 750 nM MitoTracker Red (Molecular Probes; Eugene, Oreg.) and 3 μg/ml Hoechst 33342 DNA-binding dye (Molecular Probes) and was incubated as above for 20 min. Each well on the plate was then washed with HBSS and fixed with 3.7% formaldehyde in HBSS for 15 min at room temperature. The formaldehyde was washed out with HBSS and the cells were permeabilized for 90 s with 0.5% (v/v) Triton X-100, washed with HBSS, incubated with 2 U ml$^{-1}$ Bodipy FL phallacidin (Molecular Probes) for 30 min, and washed with HBSS. The wells on the plate were then filled with 200 μl HBSS, sealed, and the plate stored at 4° C. if necessary. The fluorescence signals from plates stored this way were stable for at least two weeks after preparation. As in the nuclear translocation assay, fluorescence reagents can be designed to convert this assay into a live cell high-content screen.

Image acquisition and analysis on the ArrayScan System. The fluorescence intensity of intracellular MitoTracker Red, Hoechst 33342, and Bodipy FL phallacidin was measured with the cell screening system as described supra. Morphometric data from each pair of images obtained from each well was also obtained to detect each object in the image field (e.g., cells and nuclei), and to calculate its size, shape, and integrated intensity.

Calculations and output. A total of 50–250 cells were measured per image field. For each field of cells, the following calculations were performed: (1) The average nuclear area ($\mu m^2$) was calculated by dividing the total nuclear area in a field by the number of nuclei detected. (2) The average nuclear perimeter (μm) was calculated by dividing the sum of the perimeters of all nuclei in a field by the number of nuclei detected in that field. Highly convoluted apoptotic nuclei had the largest nuclear perimeter values. (3) The average nuclear brightness was calculated by dividing the integrated intensity of the entire field of nuclei by the number of nuclei in that field. An increase in nuclear brightness was correlated with increased DNA content. (4) The average cellular brightness was calculated by dividing the integrated intensity of an entire field of cells stained with MitoTracker dye by the number of nuclei in that field. Because the amount of MitoTracker dye that accumulates within the mitochondria is proportional to the mitochondrial potential, an increase in the average cell brightness is consistent with an increase in mitochondrial potential. (5) The average cellular brightness was also calculated by dividing the integrated intensity of an entire field of cells stained with Bodipy FL phallacidin dye by the number of nuclei in that field. Because the phallotoxins bind with high affinity to the polymerized form of actin, the amount of Bodipy FL phallacidin dye that accumulates within the cell is proportional to actin polymerization state. An increase in the average cell brightness is consistent with an increase in actin polymerization.

Figure 24:
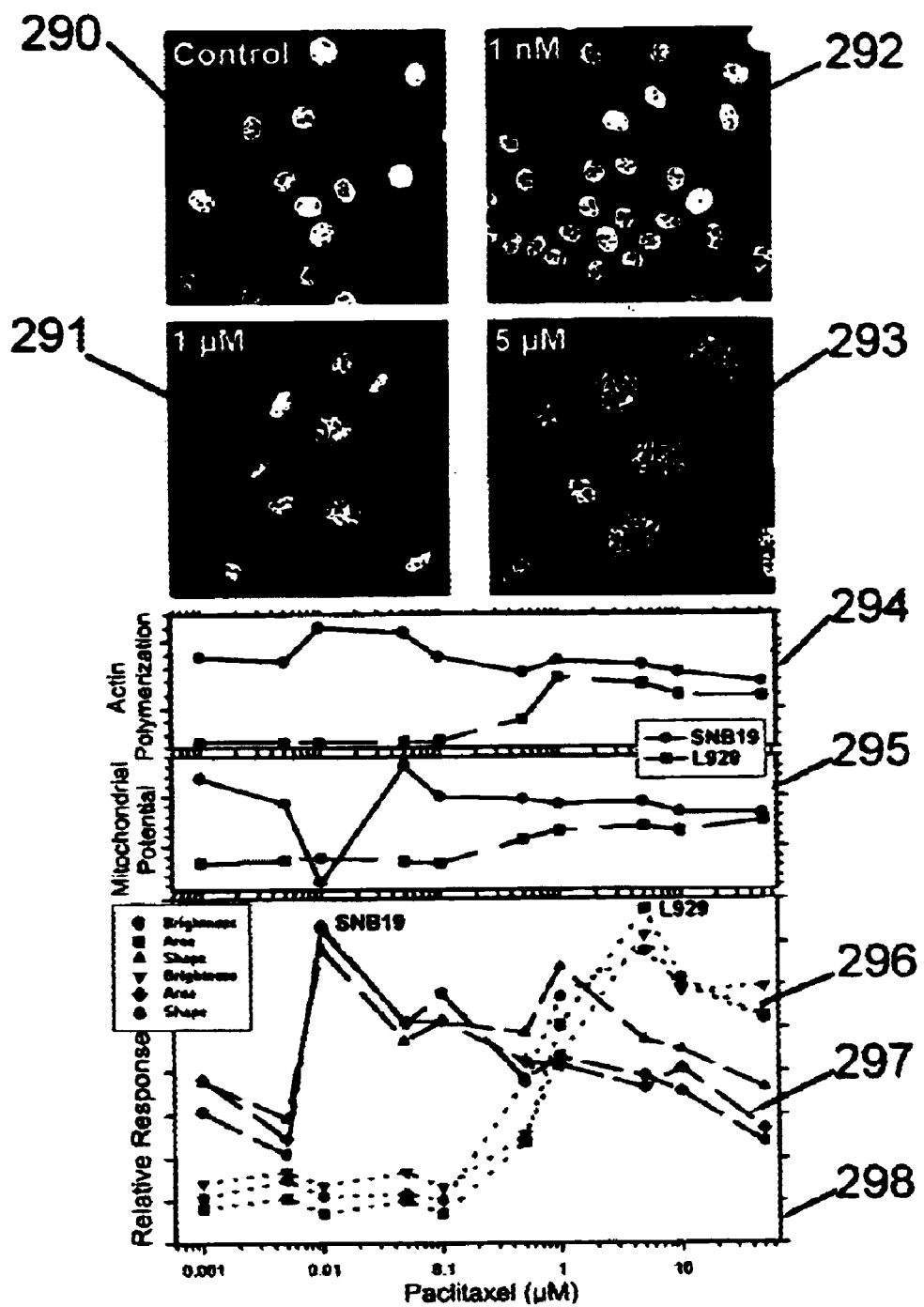
FIG. 24 details a high-content screen of drug-induced apoptosis.
Figure 25A:
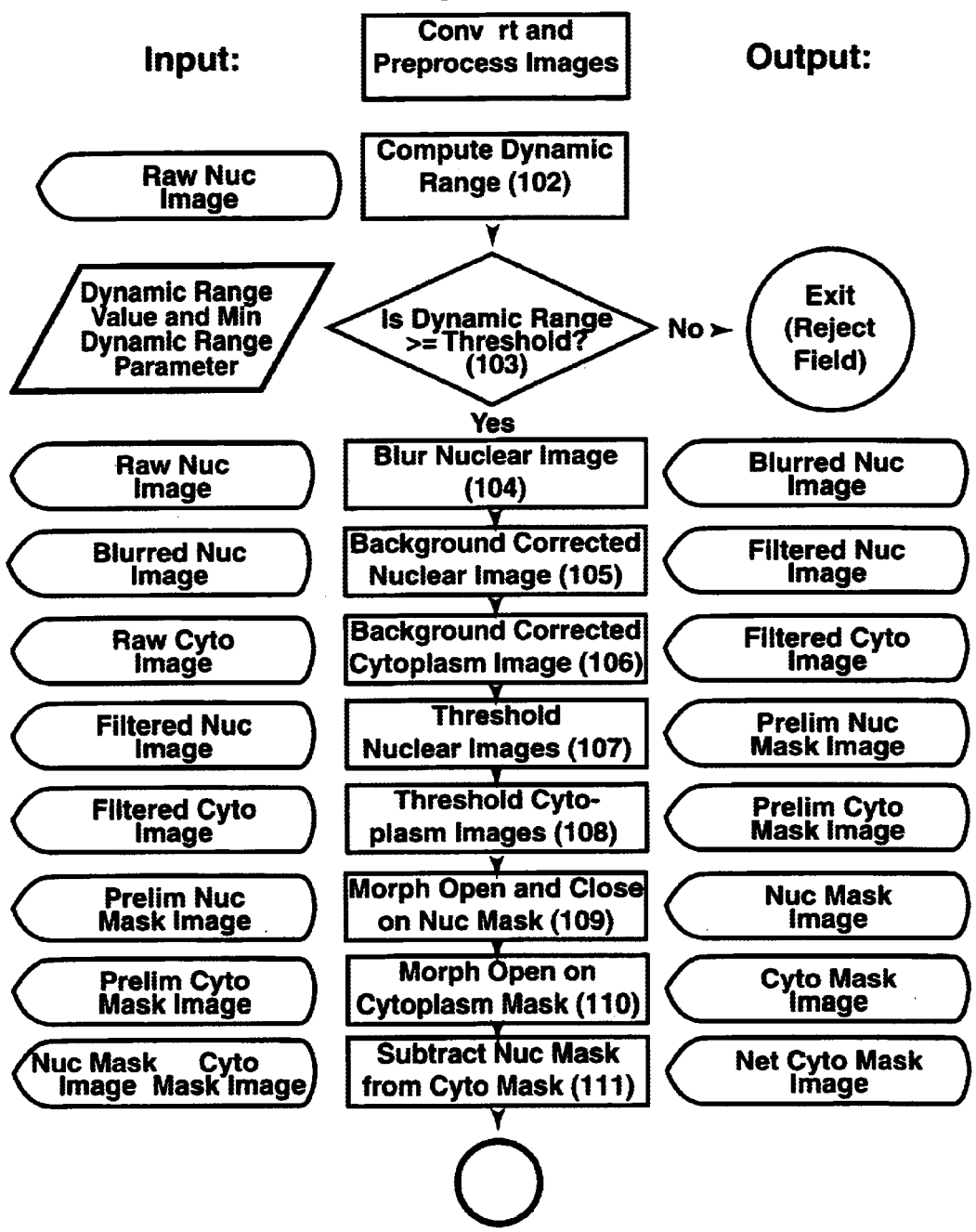
Figure 25C:
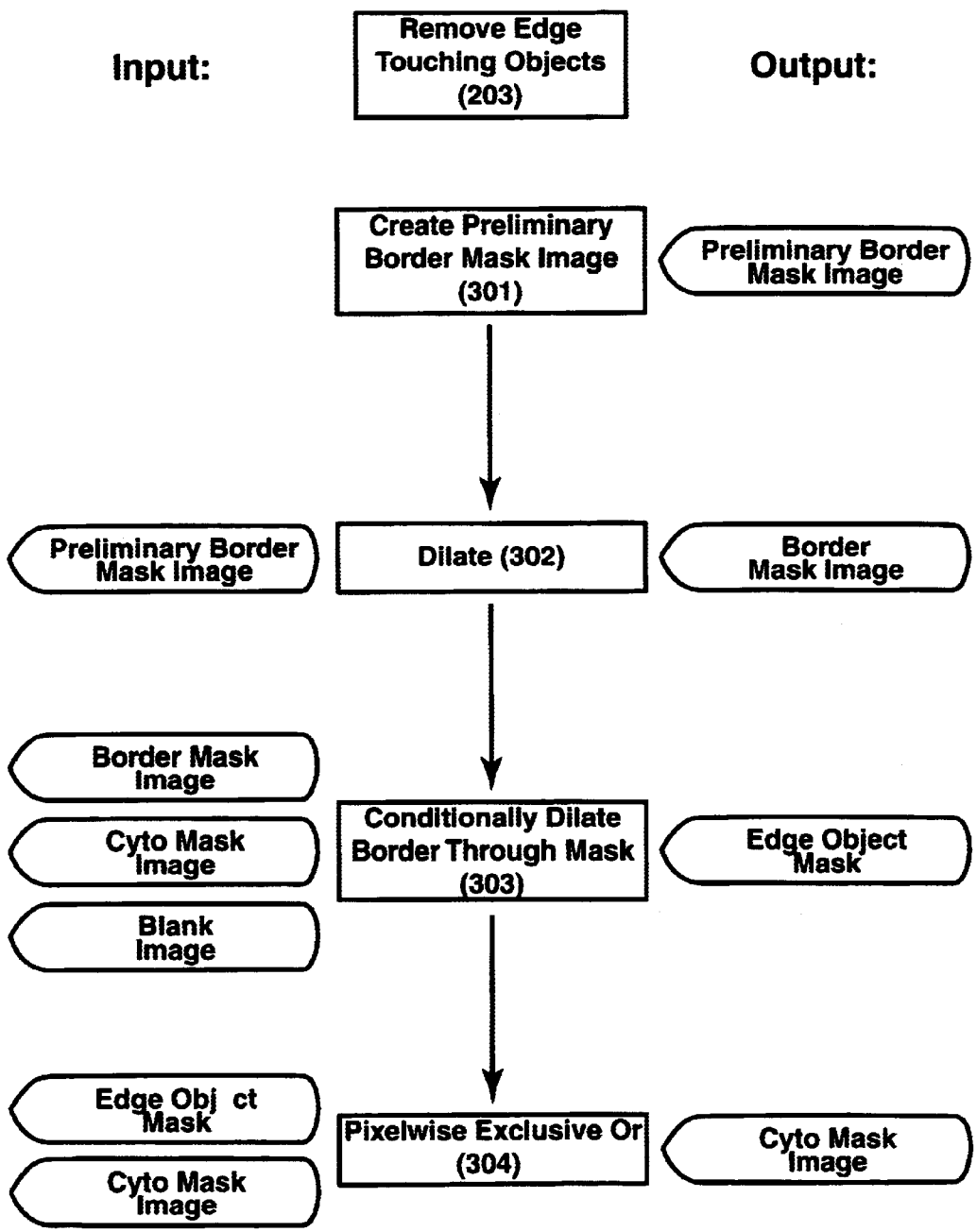
Figure 25E:
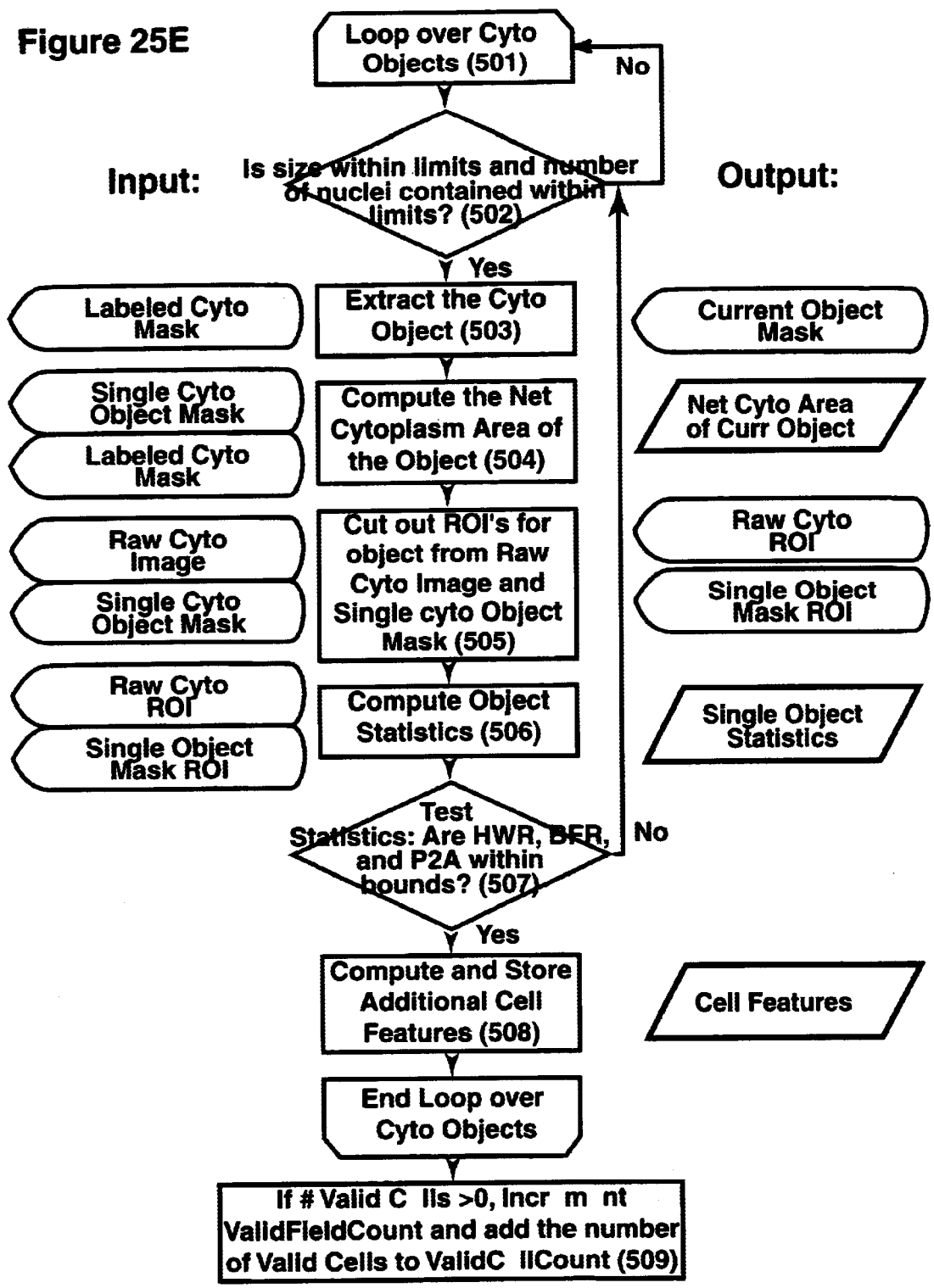

Results. FIG. 24 (top panels) shows the changes paclitaxel induced in the nuclear morphology of L-929 cells. Increasing amounts of paclitaxel caused nuclei to enlarge and fragment 293 a hallmark of apoptosis. Quantitative analysis of these and other images obtained by the cell screening system is presented in the same figure. Each parameter measured showed that the L-929 cells 296 were less sensitive to low concentrations of paclitaxel than were SNB-19 cells 297. At higher concentrations though, the L-929 cells showed a response for each parameter measured. The multiparameter approach of this assay is useful in dissecting the mechanisms of drug action. For example, the area, brightness, and fragmentation of the nucleus 298 and actin polymerization values 294 reached a maximum value when SNB-19 cells were treated with 10 nM paclitaxel (FIG. 24; top and bottom graphs). However, mitochondrial potential 295 was minimal at the same concentration of paclitaxel (FIG. 24; middle graph). The fact that all the parameters measured approached control levels at increasing paclitaxel concentrations (>10 nM) suggests that SNB-19 cells have low affinity drug metabolic or clearance pathways that are compensatory at sufficiently high levels of the drug. Contrasting the drug sensitivity of SNB-19 cells 297, L-929 showed a different response to paclitaxel 296. These fibroblastic cells showed a maximal response in many parameters at 5 μM paclitaxel, a 500-fold higher dose than SNB-19 cells. Furthermore, the L-929 cells did not show a sharp decrease in mitochondrial potential 295 at any of the paclitaxel concentrations tested. This result is consistent with the presence of unique apoptosis pathways between a normal and cancer cell line. Therefore, these results indicate that a relatively simple fluorescence labeling protocol can be coupled with the cell screening system of the present invention to produce a high-content screen of key events involved in programmed cell death.

EXAMPLE 7

Protease Induced Translocation of a Signaling Enzyme Containing a Disease-associated Sequence From Cytoplasm to Nucleus Plasmid construct. A eukaryotic expression plasmid containing a coding sequence for a green fluorescent protein—caspase (Cohen (1997), Biochemical J. 326:1–16; Liang et al. (1997), J. of Molec. Biol. 274:291–302) chimera is prepared using GFP mutants. The construct is used to transfect eukaryotic cells.

Cell preparation and transfection. Cells are trypsinized and plated 24 h prior to transfection and incubated at 37° C. and 5% $CO_2$. Transfections are performed by methods including, but not limited to calcium phosphate coprecipitation or lipofection. Cells are incubated with the calcium phosphate-DNA precipitate for 4–5 hours at 37° C. and 5% $CO_2$, washed 3–4 times with DMEM to remove the precipitate, followed by the addition of C-DMEM. Lipofectamine transfections are performed in serum-free DMEM without antibiotics according to the manufacturer's instructions. Following a 2–3 hour incubation with the DNA-liposome complexes, the medium is removed and replaced with C-DMEM.

Apopototic induction of Caspase-GFP translocation. To obtain Caspase-GFP translocation kinetic data, nuclei of transfected cells are first labeled with 5 µg/ml Hoechst 33342 (Molecular Probes) in C-DMEM for 20 minutes at 37° C. and 5% $CO_2$. Cells are washed once in Hank's Balanced Salt Solution (HBSS) followed by the addition of compounds that induce apoptosis. These compounds include, but are not limited to paclitaxel, staurosporine, ceramide, and tumor necrosis factor. To obtain fixed time point titration data, transfected cells are first washed with DMEM and then incubated at 37° C. and 5% $CO_2$ for 1 h in the presence of 0–1000 nM compound in DMEM. Cells are analyzed live or they are rinsed with HBSS, fixed for 15 min with 3.7% formaldehyde in HBSS, stained with Hoechst 33342, and washed before analysis.

Image acquisition and analysis. Kinetic data are collected by acquiring fluorescence image pairs (Caspase-GFP and Hoechst 33342-labeled nuclei) from fields of living cells at 1 min intervals for 30 min after the addition of compound. Likewise, image pairs are obtained from each well of the fixed time point screening plates 1 h after the addition of compound. In both cases, the image pairs obtained at each time point are used to define nuclear and cytoplasmic regions in each cell. Translocation of Caspase-GFP is calculated by dividing the integrated fluorescence intensity of Caspase-GFP in the nucleus by the integrated fluorescence intensity of the chimera in the cytoplasm or as a nuclear-cytoplasmic difference of GFP fluorescence. In the fixed time point screen this translocation ratio is calculated from data obtained from at least 200 cells at each concentration of compound tested. Drug-induced translocation of Caspase-GFP from the cytoplasm to the nucleus is therefore correlated with an increase in the translocation ratio. Molecular interaction libraries including, but not limited to those comprising putative activators or inhibitors of apoptosis-activated enzymes are use to screen the indicator cell lines and identify a specific ligand for the DAS, and a pathway activated by compound activity.

EXAMPLE 8

Identification of Novel Steroid Receptors From DAS

Two sources of material and/or information are required to make use of this embodiment, which allows assessment of the function of an uncharacterized gene. First, disease associated sequence bank(s) containing cDNA sequences suitable for transfection into mammalian cells can be used. Because every RADE or differential expression experiment generates up to several hundred sequences, it is possible to generate an ample supply of DAS. Second, information from primary sequence database searches can be used to place DAS into broad categories, including, but not limited to, those that contain signal sequences, seven trans-membrane motifs, conserved protease active site domains, or other identifiable motifs. Based on the information acquired from these sources, method types and indicator cell lines to be transfected are selected. A large number of motifs are already well characterized and encoded in the linear sequences contained within the large number genes in existing genomic databases.

In one embodiment, the following steps are taken:

1) Information from the DAS identification experiment (including database searches) is used as the basis for selecting the relevant biological processes. (for example, look at the DAS from a tumor line for cell cycle modulation, apoptosis, metastatic proteases, etc.)

2) Sorting of DNA sequences or DAS by identifiable motifs (ie. signal sequences, 7-transmembrane domains, conserved protease active site domains, etc.) This initial grouping will determine fluorescent tagging strategies, host cell lines, indicator cell lines, and banks of bioactive molecules to be screened, as described supra.

3) Using well established molecular biology methods, ligate DAS into an expression vector designed for this purpose. Generalized expression vectors contain promoters, enhancers, and terminators for which to deliver target sequences to the cell for transient expression. Such vectors may also contain antibody tagging sequences, direct association sequences, chromophore fusion sequences like GFP, etc. to facilitate detection when expressed by the host.

4) Transiently transfect cells with DAS containing vectors using standard transfection protocols including: calcium phosphate co-precipitation, liposome mediated, DEAE dextran mediated, polycationic mediated, viral mediated, or electroporation, and plate into microtiter plates or microwell arrays. Alternatively, transfection can be done directly in the microtiter plate itself.

5) Carry out the cell screening methods as described supra.

In this embodiment, DAS shown to possess a motif(s) suggestive of transcriptional activation potential (for example, DNA binding domain, amino terminal modulating domain, hinge region, or carboxy terminal ligand binding domain) are utilized to identify novel steroid receptors.

Defining the fluorescent tags for this experiment involves identification of the nucleus through staining, and tagging the DAS by creating a GFP chimera via insertion of DAS into an expression vector, proximally fused to the gene encoding GFP. Alternatively, a single chain antibody fragment with high affinity to some portion of the expressed DAS could be constructed using technology available in the art (Cambridge Antibody Technologies) and linked to a fluorophore (FITC) to tag the putative transcriptional activator/receptor in the cells. This alternative would provide an external tag requiring no DNA transfection and therefore would be useful if distribution data were to be gathered from the original primary cultures used to generate the DAS.

Plasmid construct. A eukaryotic expression plasmid containing a coding sequence for a green fluorescent protein—DAS chimera is prepared using GFP mutants. The construct is used to transfect HeLa cells. The plasmid, when transfected into the host cell, produces a GFP fused to the DAS protein product, designated GFP-DASpp.

Cell preparation and transfection. HeLa cells are trypsinized and plated using DMEM containing 5% charcoal/dextran-treated fetal bovine serum (FBS) (Hyclone) and 1% penicillin-streptomycin (C-DMEM) 12–24 hours prior to transfection and incubated at 37° C. and 5% $CO_2$. Transfections are performed by calcium phosphate coprecipitation or with Lipofectamine (Life Technologies). For the calcium phosphate transfections, the medium is replaced, prior to transfection, with DMEM containing 5% charcoal/dextran-treated FBS. Cells are incubated with the calcium phosphate-DNA precipitate for 4–5 hours at 37° C. and 5% $CO_2$, and washed 3–4 times with DMEM to remove the precipitate, followed by the addition of C-DMEM. Lipofectamine transfections are performed in serum-free DMEM without antibiotics according to the manufacturer's instructions. Following a 2–3 hour incubation with the DNA-liposome complexes, the medium is removed and replaced with C-DMEM. All transfected cells in 96-well microtiter plates are incubated at 33° C. and 5% $CO_2$ for 24–48 hours prior to drug treatment. Experiments are performed with the receptor expressed transiently in HeLa cells.

Localization of expressed GFP-DASpp inside cells. To obtain cellular distribution data, nuclei of transfected cells are first labeled with 5 µg/ml Hoechst 33342 (Molecular Probes) in C-DMEM for 20 minutes at 33° C. and 5% $CO_2$. Cells are washed once in Hank's Balanced Salt Solution (HBSS). The cells are analyzed live or they are rinsed with HBSS, fixed for 15 min with 3.7% formaldehyde in HBSS, stained with Hoechst 33342, and washed before analysis.

In a preferred embodiment, image acquisition and analysis are performed using the cell screening system of the present invention. The intracellular GFP-DASpp fluorescence signal is collected by acquiring fluorescence image pairs (GFP-DASpp and Hoechst 33342-labeled nuclei) from field cells. The image pairs obtained at each time point are used to define nuclear and cytoplasmic regions in each cell. Data demonstrating dispersed signal in the cytoplasm would be consistent with known steroid receptors that are DNA transcriptional activators.

Screening for induction of GFP-DASpp translocation. Using the above construct, confirmed for appropriate expression of the GFP-DASpp, as an indicator cell line, a screen of various ligands is performed using a series of steroid type ligands including, but not limited to: estrogen, progesterone, retinoids, growth factors, androgens, and many other steroid and steroid based molecules. Image acquisition and analysis are performed using the cell screening system of the invention. The intracellular GFP-DASpp fluorescence signal is collected by acquiring fluorescence image pairs (GFP-DASpp and Hoechst 33342-labeled nuclei) from fields cells. The image pairs obtained at each time point are used to define nuclear and cytoplasmic regions in each cell. Translocation of GFP-DASpp is calculated by dividing the integrated fluorescence intensity of GFP-DASpp in the nucleus by the integrated fluorescence intensity of the chimera in the cytoplasm or as a nuclear-cytoplasmic difference of GFP fluorescence. A translocation from the cytoplasm into the nucleus indicates a ligand binding activation of the DASpp thus identifying the potential receptor class and action. Combining this data with other data obtained in a similar fashion using known inhibitors and modifiers of steroid receptors, would either validate the DASpp as a target, or more data would be generated from various sources.

EXAMPLE 9

Additional Screens

Translocation Between the Plasma Membrane and the Cytoplasm:

Profilactin complex dissociation and binding of profilin to the plasma membrane. In one embodiment, a fluorescent protein biosensor of profilin membrane binding is prepared by labeling purified profilin (Federov et al. (1994), *J. Molec. Biol.* 241:480–482; Lanbrechts et al. (1995), *Eur. J. Biochem.* 230:281–286) with a probe possessing a fluorescence lifetime in the range of 2–300 ns. The labeled profilin is introduced into living indicator cells using bulk loading methodology and the indicator cells are treated with test compounds. Fluorescence anisotropy imaging microscopy (Gough and Taylor (1993), *J. Cell Biol.* 121:1095–1107) is used to measure test-compound dependent movement of the fluorescent derivative of profilin between the cytoplasm and membrane for a period of time after treatment ranging from 0.1 s to 10 h.

Rho-RhoGDI complex translocation to the membrane. In another embodiment, indicator cells are treated with test compounds and then fixed, washed, and permeabilized. The indicator cell plasma membrane, cytoplasm, and nucleus are all labeled with distinctly colored markers followed by immunolocalization of Rho protein (Self et al. (1995), *Methods in Enzymology* 256:3–10; Tanaka et al. (1995), *Methods in Enzymology* 256:41–49) with antibodies labeled with a fourth color. Each of the four labels is imaged separately using the cell screening system, and the images used to calculate the amount of inhibition or activation of translocation effected by the test compound. To do this calculation, the images of the probes used to mark the plasma membrane and cytoplasm are used to mask the image of the immunological probe marking the location of intracellular Rho protein. The integrated brightness per unit area under each mask is used to form a translocation quotient by dividing the plasma membrane integrated brightness/area by the cytoplasmic integrated brightness/area. By comparing the translocation quotient values from control and experimental wells, the percent translocation is calculated for each potential lead compound.

β-Arrestin Translocation to the Plasma Membrane Upon G-protein Receptor Activation.

In another embodiment of a cytoplasm to membrane translocation high-content screen, the translocation of β-arrestin protein from the cytoplasm to the plasma membrane is measured in response to cell treatment. To measure the translocation, living indicator cells containing luminescent domain markers are treated with test compounds and the movement of the β-arrestin marker is measured in time and space using the cell screening system of the present invention. In a preferred embodiment, the indicator cells contain luminescent markers consisting of a green fluorescent protein β-arrestin (GFP-β-arrestin) protein chimera (Barak et al. (1997), *J. Biol. Chem.* 272:27497–27500; Daaka et al. (1998), *J. Biol. Chem.* 273:685–688) that is expressed by the indicator cells through the use of transient or stable cell transfection and other reporters used to mark cytoplasmic and membrane domains. When the indicator cells are in the resting state, the domain marker molecules partition predominately in the plasma membrane or in the cytoplasm. In the high-content screen, these markers are used to delineate the cell cytoplasm and plasma membrane in distinct channels of fluorescence. When the indicator cells are treated with a test compound, the dynamic redistribution of the GFP-β-arrestin is recorded as a series of images over a time scale ranging from 0.1 s to 10 h. In a preferred embodiment, the time scale is 1 h. Each image is analyzed by a method that quantifies the movement of the GFP-β-arrestin protein chimera between the plasma membrane and the cytoplasm. To do this calculation, the images of the probes used to mark the plasma membrane and cytoplasm are used to mask the image of the GFP-β-arrestin probe marking the location of intracellular GFP-β-arrestin protein. The integrated brightness per unit area under each mask is used to form a translocation quotient by dividing the plasma membrane integrated brightness/area by the cytoplasmic integrated brightness/area. By comparing the translocation quotient values from control and experimental wells, the percent translocation is calculated for each potential lead compound. The output of the high-content screen relates quantitative data describing the magnitude of the translocation within a large number of individual cells that have been treated with test compounds of interest.

Translocation Between the Endoplasmic Reticulum and the Golgi:

In one embodiment of an endoplasmic reticulum to Golgi translocation high-content screen, the translocation of a VSVG protein from the ts045 mutant strain of vesicular stomatitis virus (Ellenberg et al. (1997), *J. Cell Biol.* 138:1193–1206; Presley et al. (1997) *Nature* 389:81–85) from the endoplasmic reticulum to the Golgi domain is measured in response to cell treatment. To measure the translocation, indicator cells containing luminescent reporters are treated with test compounds and the movement of the reporters is measured in space and time using the cell screening system of the present invention. The indicator cells contain luminescent reporters consisting of a GFP-VSVG protein chimera that is expressed by the indicator cell through the use of transient or stable cell transfection and other domain markers used to measure the localization of the endoplasmic reticulum and Golgi domains. When the indicator cells are in their resting state at 40° C., the GFP-VSVG protein chimera molecules are partitioned predominately in the endoplasmic reticulum. In this high-content screen, domain markers of distinct colors used to delineate the endoplasmic reticulum and the Golgi domains in distinct channels of fluorescence. When the indicator cells are treated with a test compound and the temperature is simultaneously lowered to 32° C., the dynamic redistribution of the GFP-VSVG protein chimera is recorded as a series of images over a time scale ranging from 0.1 s to 10 h. Each image is analyzed by a method that quantifies the movement of the GFP-VSVG protein chimera between the endoplasmic reticulum and the Golgi domains. To do this calculation, the images of the probes used to mark the endoplasmic reticulum and the Golgi domains are used to mask the image of the GFP-VSVG probe marking the location of intracellular GFP-VSVG protein. The integrated brightness per unit area under each mask is used to form a translocation quotient by dividing the endoplasmic reticulum integrated brightness/area by the Golgi integrated brightness/area. By comparing the translocation quotient values from control and experimental wells, the percent translocation is calculated for each potential lead compound. The output of the high-content screen relates quantitative data describing the magnitude of the translocation within a large number of individual cells that have been treated with test compounds of interest at final concentrations ranging from $10^{-12}$ M to $10^{-3}$ M for a period ranging from 1 min to 10 h.

Induction and Inhibition of Organellar Function:

Intracellular Microtubule Stability.

In another aspect of the invention, an automated method for identifying compounds that modify microtubule structure is provided. In this embodiment, indicator cells are treated with test compounds and the distribution of luminescent microtubule-labeling molecules is measured in space and time using a cell screening system, such as the one disclosed above. The luminescent microtubule-labeling molecules may be expressed by or added to the cells either before, together with, or after contacting the cells with a test compound.

In one embodiment of this aspect of the invention, living cells express a luminescently labeled protein biosensor of microtubule dynamics, comprising a protein that labels microtubules fused to a luminescent protein. Appropriate microtubule-labeling proteins for this aspect of the invention include, but are not limited to $\alpha$ and $\beta$ tubulin isoforms, and MAP4. Preferred embodiments of the luminescent protein include, but are not limited to green fluorescent protein (GFP) and GFP mutants. In a preferred embodiment, the method involves transfecting cells with a microtubule labeling luminescent protein, wherein the microtubule labeling protein can be, but is not limited to, $\alpha$-tubulin, $\beta$-tubulin, or microtubule-associated protein 4 (MAP4). The approach outlined here enables those skilled in the art to make live cell measurements to determine the effect of lead compounds on tubulin activity and microtubule stability in vivo.

In a most preferred embodiment, MAP4 is fused to a modified version of the *Aequorea victoria* green fluorescent protein (GFP). A DNA construct has been made which consists of a fusion between the EGFP coding sequence (available from Clontech) and the coding sequence for mouse MAP4. (Olson et al., (1995), J. Cell Biol. 130(3): 639–650). MAP4 is a ubiquitous microtubule-associated protein that is known to interact with microtubules in interphase as well as mitotic cells (Olmsted and Murofushi, (1993), MAP4. In "Guidebook to the Cytoskeleton and Motor Proteins." Oxford University Press. T. Kreis and R. Vale, eds.) Its localization, then, can serve as an indicator of the localization, organization, and integrity of microtubules in living (or fixed) cells at all stages of the cell cycle for cell-based HCS assays. While MAP2 and tau (microtubule associated proteins expressed specifically in neuronal cells) have been used to form GFP chimeras (Kaech et al., (1996) Neuron. 17: 1189–1199; Hall et al., (1997), Proc. Nat. Acad. Sci. 94: 4733–4738) their restricted cell type distribution and the tendency of these proteins to bundle microtubules when overexpressed make these proteins less desirable as molecular reagents for analysis in live cells originating from varied tissues and organs. Moderate overexpression of GFP-MAP4 does not disrupt microtubule function or integrity (Olson et al., 1995). Similar constructs can be made using $\beta$-tubulin or $\alpha$-tubulin via standard techniques in the art. These chimeras will provide a means to observe and analyze microtubule activity in living cells during all stages of the cell cycle.

In another embodiment, the luminescently labeled protein biosensor of microtubule dynamics is expressed, isolated, and added to the cells to be analyzed via bulk loading techniques, such as microinjection, scrape loading, and impact-mediated loading. In this embodiment, there is not an issue of overexpression within the cell, and thus $\alpha$ and $\beta$ tubulin isoforms, MAP4, MAP2 and/or tau can all be used.

In a further embodiment, the protein biosensor is expressed by the cell, and the cell is subsequently contacted with a luminescent label, such as a labeled antibody, that detects the protein biosensor, endogenous levels of a protein antigen, or both. In this embodiment, a luminescent label that detects a$\alpha$ and $\beta$ tubulin isoforms, MAP4, MAP2 and/or tau, can be used.

A variety of GFP mutants are available, all of which would be effective in this invention, including, but not limited to, GFP mutants which are commercially available (Clontech, California).

The MAP4 construct has been introduced into several mammalian cell lines (BHK-21, Swiss 3T3, HeLa, HEK 293, LLCPK) and the organization and localization of tubulin has been visualized in live cells by virtue of the GFP fluorescence as an indicator of MAP4 localization. The construct can be expressed transiently or stable cell lines can be prepared by standard methods. Stable HeLa cell lines expressing the EGFP-MAP4 chimera have been obtained, indicating that expression of the chimera is not toxic and does not interfere with mitosis.

Possible selectable markers for establishment and maintenance of stable cell lines include, but are not limited to the neomycin resistance gene, hygromycin resistance gene, zeocin resistance gene, puromycin resistance gene, bleomycin resistance gene, and blastacidin resistance gene.

The utility of this method for the monitoring of microtubule assembly, disassembly, and rearrangement has been demonstrated by treatment of transiently and stably transfected cells with microtubule drugs such as paclitaxel, nocodazole, vincristine, or vinblastine.

The present method provides high-content and combined high throughput-high content cell-based screens for antimicrotubule drugs, particularly as one parameter in a multi-parametric cancer target screen. The EGFP-MAP4 construct used herein can also be used as one of the components of a high-content screen that measures multiple signaling pathways or physiological events. In a preferred embodiment, a combined high throughput and high content screen is employed, wherein multiple cells in each of the locations containing cells are analyzed in a high throughput mode, and only a subset of the locations containing cells are analyzed in a high content mode. The high throughput screen can be any screen that would be useful to identify those locations containing cells that should be further analyzed, including, but not limited to, identifying locations with increased luminescence intensity, those exhibiting expression of a reporter gene, those undergoing calcium changes, and those undergoing pH changes.

In addition to drug screening applications, the present invention may be applied to clinical diagnostics, the detection of chemical and biological warfare weapons, and the basic research market since fundamental cell processes, such as cell division and motility, are highly dependent upon microtubule dynamics.

Image Acquisition and Analysis

Image data can be obtained from either fixed or living indicator cells. To extract morphometric data from each of the images obtained the following method of analysis is used:

1. Threshold each nucleus and cytoplasmic image to produce a mask that has value=0 for each pixel outside a nucleus or cell boundary.
2. Overlay the mask on the original image, detect each object in the field (i.e., nucleus or cell), and calculate its size, shape, and integrated intensity.
3. Overlay the whole cell mask obtained above on the corresponding luminescent microtubule image and apply one or more of the following set of classifiers to determine the micrtotubule morphology and the effect of drugs on microtubule morphology.

Microtubule morphology is defined using a set of classifiers to quantify aspects of microtubule shape, size, aggregation state, and polymerization state. These classifiers can be based on approaches that include co-occurrence matrices, texture measurements, spectral methods, structural methods, wavelet transforms, statistical methods, or combinations thereof. Examples of such classifiers are as follows:

1. A classifier to quantify microtubule length and width using edge detection methods such as that discussed in Kolega et al. ((1993). *BioImaging* 1:136–150), which discloses a non-automated method to determine edge strength in individual cells), to calculate the total edge strength within each cell. To normalize for cell size, the total edge strength can be divided by the cell area to give a "microtubule morphology" value. Large microtubule morphology values are associated with strong edge strength values and are therefore maximal in cells containing distinct microtubule structures. Likewise, small microtubule morphology values are associated with weak edge strength and are minimal in cells with depolymerized microtubules. The physiological range of microtubule morphology values is set by treating cells with either the microtubule stabilizing drug paclitaxel (10 $\mu$M) or the microtubule depolymerizing drug nocodazole (10 $\mu$g/ml).

2. A classifier to quantify microtubule aggregation into punctate spots or foci using methodology from the receptor internalization methods discussed supra.
3. A classifier to quantify microtubule depolymerization using a measure of image texture.
4. A classifier to quantify apparent interconnectivity, or branching (or both), of the microtubules.
5. Measurement of the kinetics of microtubule reorganization using the above classifiers on a time series of images of cells treated with test compounds.

In a further aspect, kits are provided for analyzing microtubule stability, comprising an expression vector comprising a nucleic acid that encodes a microtubule labeling protein and instructions for using the expression vector for carrying out the methods described above. In a preferred embodiment, the expression vector further comprises a nucleic acid that encodes a luminescent protein, wherein the microtubule binding protein and the luminescent protein thereof are expressed as a fusion protein. Alternatively, the kit may contain an antibody that specifically binds to the microtubule-labeling protein. In a further embodiment, the kit includes cells that express the microtubule labeling protein. In a preferred embodiment, the cells are transfected with the expression vector. In another preferred embodiment, the kits further contain a compound that is known to disrupt microtubule structure, including but not limited to curacin, nocodazole, vincristine, or vinblastine. In another preferred embodiment, the kits further comprise a compound that is known to stabilize microtubule structure, including but not limited to taxol (paclitaxel), and discodermolide.

In another aspect, the present invention comprises a machine readable storage medium comprising a program containing a set of instructions for causing a cell screening system to execute the disclosed methods for analyzing microtubule stability, wherein the cell screening system comprises an optical system with a stage adapted for holding a plate containing cells, a digital camera, a means for directing fluorescence or luminescence emitted from the cells to the digital camera, and a computer means for receiving and processing the digital data from the digital camera.

High-content Screens Involving the Functional Localization of Macromolecules

Within this class of high-content screen, the functional localization of macromolecules in response to external stimuli is measured within living cells.

Glycolytic enzyme activity regulation. In a preferred embodiment of a cellular enzyme activity high-content screen, the activity of key glycolytic regulatory enzymes are measured in treated cells. To measure enzyme activity, indicator cells containing luminescent labeling reagents are treated with test compounds and the activity of the reporters is measured in space and time using cell screening system of the present invention.

In one embodiment, the reporter of intracellular enzyme activity is fructose-6-phosphate, 2-kinase/fructose-2,6-bisphosphatase (PFK-2), a regulatory enzyme whose phosphorylation state indicates intracellular carbohydrate anabolism or catabolism (Deprez et al. (1997) *J. Biol. Chem.* 272:17269–17275; Kealer et al. (1996) *FEBS Letters*

395:225–227; Lee et al. (1996), *Biochemistry* 35:6010–6019). The indicator cells contain luminescent reporters consisting of a fluorescent protein biosensor of PFK-2 phosphorylation. The fluorescent protein biosensor is constructed by introducing an environmentally sensitive fluorescent dye near to the known phosphorylation site of the enzyme (Deprez et al. (1997), supra; Giuliano et al. (1995), supra). The dye can be of the ketocyanine class (Kessler and Wolfbeis (1991), *Spectrochimica Acta* 47A:187–192) or any class that contains a protein reactive moiety and a fluorochrome whose excitation or emission spectrum is sensitive to solution polarity. The fluorescent protein biosensor is introduced into the indicator cells using bulk loading methodology.

Living indicator cells are treated with test compounds, at final concentrations ranging from $10^{-12}$ M to $10^{-3}$ M for times ranging from 0.1 s to 10 h. In a preferred embodiment, ratio image data are obtained from living treated indicator cells by collecting a spectral pair of fluorescence images at each time point. To extract morphometric data from each time point, a ratio is made between each pair of images by numerically dividing the two spectral images at each time point, pixel by pixel. Each pixel value is then used to calculate the fractional phosphorylation of PFK-2. At small fractional values of phosphorylation, PFK-2 stimulates carbohydrate catabolism. At high fractional values of phosphorylation, PFK-2 stimulates carbohydrate anabolism.

Protein kinase A activity and localization of subunits. In another embodiment of a high-content screen, both the domain localization and activity of protein kinase A (PKA) within indicator cells are measured in response to treatment with test compounds.

The indicator cells contain luminescent reporters including a fluorescent protein biosensor of PKA activation. The fluorescent protein biosensor is constructed by introducing an environmentally sensitive fluorescent dye into the catalytic subunit of PKA near the site known to interact with the regulatory subunit of PKA (Harootunian et al. (1993), *Mol. Biol. of the Cell* 4:993–1002; Johnson et al. (1996), *Cell* 85:149–158; Giuliano et al. (1995), supra). The dye can be of the ketocyanine class (Kessler, and Wolfbeis (1991), *Spectrochimica Acta* 47A:187–192) or any class that contains a protein reactive moiety and a fluorochrome whose excitation or emission spectrum is sensitive to solution polarity. The fluorescent protein biosensor of PKA activation is introduced into the indicator cells using bulk loading methodology.

In one embodiment, living indicator cells are treated with test compounds, at final concentrations ranging from $10^{-12}$ M to $10^{-3}$ M for times ranging from 0.1 s to 10 h. In a preferred embodiment, ratio image data are obtained from living treated indicator cells. To extract biosensor data from each time point, a ratio is made between each pair of images, and each pixel value is then used to calculate the fractional activation of PKA (e.g., separation of the catalytic and regulatory subunits after cAMP binding). At high fractional values of activity, PFK-2 stimulates biochemical cascades within the living cell.

To measure the translocation of the catalytic subunit of PKA, indicator cells containing luminescent reporters are treated with test compounds and the movement of the reporters is measured in space and time using the cell screening system. The indicator cells contain luminescent reporters consisting of domain markers used to measure the localization of the cytoplasmic and nuclear domains. When the indicator cells are treated with a test compounds, the dynamic redistribution of a PKA fluorescent protein biosensor is recorded intracellularly as a series of images over a time scale ranging from 0.1 s to 10 h. Each image is analyzed by a method that quantifies the movement of the PKA between the cytoplasmic and nuclear domains. To do this calculation, the images of the probes used to mark the cytoplasmic and nuclear domains are used to mask the image of the PKA fluorescent protein biosensor. The integrated brightness per unit area under each mask is used to form a translocation quotient by dividing the cytoplasmic integrated brightness/area by the nuclear integrated brightness/area. By comparing the translocation quotient values from control and experimental wells, the percent translocation is calculated for each potential lead compound. The output of the high-content screen relates quantitative data describing the magnitude of the translocation within a large number of individual cells that have been treated with test compound in the concentration range of $10^{-12}$ M to $10^{-3}$ M.

High-content Screens Involving the Induction or Inhibition of Gene Expression RNA-based Fluorescent Biosensors Cytoskeletal protein transcription and message localization. Regulation of the general classes of cell physiological responses including cell-substrate adhesion, cell-cell adhesion, signal transduction, cell-cycle events, intermediary and signaling molecule metabolism, cell locomotion, cell-cell communication, and cell death can involve the alteration of gene expression. High-content screens can also be designed to measure this class of physiological response.

In one embodiment, the reporter of intracellular gene expression is an oligonucleotide that can hybridize with the target mRNA and alter its fluorescence signal. In a preferred embodiment, the oligonucleotide is a molecular beacon (Tyagi and Kramer (1996) *Nat. Biotechnol.* 14:303–308), a luminescence-based reagent whose fluorescence signal is dependent on intermolecular and intramolecular interactions. The fluorescent biosensor is constructed by introducing a fluorescence energy transfer pair of fluorescent dyes such that there is one at each end (5' and 3') of the reagent. The dyes can be of any class that contains a protein reactive moiety and fluorochromes whose excitation and emission spectra overlap sufficiently to provide fluorescence energy transfer between the dyes in the resting state, including, but not limited to, fluorescein and rhodamine (Molecular Probes, Inc.). In a preferred embodiment, a portion of the message coding for β-actin (Kislauskis et al. (1994), *J. Cell Biol.* 127:441–451; McCann et al. (1997), *Proc. Natl. Acad. Sci.* 94:5679–5684; Sutoh (1982), *Biochemistry* 21:3654–3661) is inserted into the loop region of a hairpin-shaped oligonucleotide with the ends tethered together due to intramolecular hybridization. At each end of the biosensor a fluorescence donor (fluorescein) and a fluorescence acceptor (rhodamine) are covalently bound. In the tethered state, the fluorescence energy transfer is maximal and therefore indicative of an unhybridized molecule. When hybridized with the mRNA coding for β-actin, the tether is broken and energy transfer is lost. The complete fluorescent biosensor is introduced into the indicator cells using bulk loading methodology.

In one embodiment, living indicator cells are treated with test compounds, at final concentrations ranging from $10^{-12}$ M to $10^{-3}$ M for times ranging from 0.1 s to 10 h. In a preferred embodiment, ratio image data are obtained from living treated indicator cells. To extract morphometric data from each time point, a ratio is made between each pair of images, and each pixel value is then used to calculate the fractional hybridization of the labeled nucleotide. At small fractional values of hybridization little expression of β-actin is indicated. At high fractional values of hybridization, maximal expression of β-actin is indicated. Furthermore, the distribution of hybridized molecules within the cytoplasm of the indicator cells is also a measure of the physiological response of the indicator cells.

Cell Surface Binding of a Ligand

Labeled insulin binding to its cell surface receptor in living cells. Cells whose plasma membrane domain has been labeled with a labeling reagent of a particular color are incubated with a solution containing insulin molecules (Lee et al. (1997), *Biochemistry* 36:2701–2708; Martinez-Zaguilan et al. (1996), *Am. J. Physiol.* 270:C1438–C1446) that are labeled with a luminescent probe of a different color for an appropriate time under the appropriate conditions. After incubation, unbound insulin molecules are washed away, the cells fixed and the distribution and concentration of the insulin on the plasma membrane is measured. To do this, the cell membrane image is used as a mask for the insulin image. The integrated intensity from the masked insulin image is compared to a set of images containing known amounts of labeled insulin. The amount of insulin bound to the cell is determined from the standards and used in conjunction with the total concentration of insulin incubated with the cell to calculate a dissociation constant or insulin to its cell surface receptor.

Labeling of Cellular Compartments

Whole Cell Labeling

Whole cell labeling is accomplished by labeling cellular components such that dynamics of cell shape and motility of the cell can be measured over time by analyzing fluorescence images of cells.

In one embodiment, small reactive fluorescent molecules are introduced into living cells. These membrane-permeant molecules both diffuse through and react with protein components in the plasma membrane. Dye molecules react with intracellular molecules to both increase the fluorescence signal emitted from each molecule and to entrap the fluorescent dye within living cells. These molecules include reactive chloromethyl derivatives of aminocoumarins, hydroxycoumarins, eosin diacetate, fluorescein diacetate, some Bodipy dye derivatives, and tetramethylrhodamine. The reactivity of these dyes toward macromolecules includes free primary amino groups and free sulfhydryl groups.

In another embodiment, the cell surface is labeled by allowing the cell to interact with fluorescently labeled antibodies or lectins (Sigma Chemical Company, St. Louis, Mo.) that react specifically with molecules on the cell surface. Cell surface protein chimeras expressed by the cell of interest that contain a green fluorescent protein, or mutant thereof, component can also be used to fluorescently label the entire cell surface. Once the entire cell is labeled, images of the entire cell or cell array can become a parameter in high content screens, involving the measurement of cell shape, motility, size, and growth and division.

Plasma Membrane Labeling

In one embodiment, labeling the whole plasma membrane employs some of the same methodology described above for labeling the entire cells. Luminescent molecules that label the entire cell surface act to delineate the plasma membrane.

In a second embodiment subdomains of the plasma membrane, the extracellular surface, the lipid bilayer, and the intracellular surface can be labeled separately and used as components of high content screens. In the first embodiment, the extracellular surface is labeled using a brief treatment with a reactive fluorescent molecule such as the succinimidyl ester or iodoacetamde derivatives of fluorescent dyes such as the fluoresceins, rhodamines, cyanines, and Bodipys.

In a third embodiment, the extracellular surface is labeled using fluorescently labeled macromolecules with a high affinity for cell surface molecules. These include fluorescently labeled lectins such as the fluorescein, rhodamine, and cyanine derivatives of lectins derived from jack bean (Con A), red kidney bean (erythroagglutinin PHA-E), or wheat germ.

In a fourth embodiment, fluorescently labeled antibodies with a high affinity for cell surface components are used to label the extracellular region of the plasma membrane. Extracellular regions of cell surface receptors and ion channels are examples of proteins that can be labeled with antibodies.

In a fifth embodiment, the lipid bilayer of the plasma membrane is labeled with fluorescent molecules. These molecules include fluorescent dyes attached to long chain hydrophobic molecules that interact strongly with the hydrophobic region in the center of the plasma membrane lipid bilayer. Examples of these dyes include the PKH series of dyes (U.S. Pat. Nos. 4,783,401, 4,762701, and 4,859,584; available commercially from Sigma Chemical Company, St. Loius, Mo.), fluorescent phospholipids such as nitrobenzoxadiazole glycerophosphoethanolamine and fluorescein-derivatized dihexadecanoylglycerophosphoetha-nolamine, fluorescent fatty acids such as 5-butyl-4,4-difluoro-4-bora-3a,4a-diaza-s-indacene-3-nonanoic acid and 1-pyrenedecanoic acid (Molecular Probes, Inc.), fluorescent sterols including cholesteryl 4,4-difluoro-5,7-dimethyl-4-bora-3a,4a-diaza-s-indacene-3-dodecanoate and cholesteryl 1-pyrenehexanoate, and fluorescently labeled proteins that interact specifically with lipid bilayer components such as the fluorescein derivative of annexin V (Caltag Antibody Co, Burlingame, Calif.).

In another embodiment, the intracellular component of the plasma membrane is labeled with fluorescent molecules. Examples of these molecules are the intracellular components of the trimeric G-protein receptor, adenylyl cyclase, and ionic transport proteins. These molecules can be labeled as a result of tight binding to a fluorescently labeled specific antibody or by the incorporation of a fluorescent protein chimera that is comprised of a membrane-associated protein and the green fluorescent protein, and mutants thereof.

Endosome Fluorescence Labeling

In one embodiment, ligands that are transported into cells by receptor-mediated endocytosis are used to trace the dynamics of endosomal organelles. Examples of labeled ligands include Bodipy FL-labeled low density lipoprotein complexes, tetramethylrhodamine transferrin analogs, and fluorescently labeled epidermal growth factor (Molecular Probes, Inc.)

In a second embodiment, fluorescently labeled primary or secondary antibodies (Sigma Chemical Co. St. Louis, Mo.; Molecular Probes, Inc. Eugene, Oreg.; Caltag Antibody Co.) that specifically label endosomal ligands are used to mark the endosomal compartment in cells.

In a third embodiment, endosomes are fluorescently labeled in cells expressing protein chimeras formed by fusing a green fluorescent protein, or mutants thereof, with a receptor whose internalization labels endosomes. Chimeras of the EGF, transferrin, and low density lipoprotein receptors are examples of these molecules.

Lysosome Labeling

In one embodiment, membrane permeant lysosome-specific luminescent reagents are used to label the lysosomal compartment of living and fixed cells. These reagents include the luminescent molecules neutral red, N-(3-((2,4-dinitrophenyl)amino)propyl)-N-(3-aminopropyl)

methylamine, and the LysoTracker probes which report intralysosomal pH as well as the dynamic distribution of lysosomes (Molecular Probes, Inc.)

In a second embodiment, antibodies against lysosomal antigens (Sigma Chemical Co.; Molecular Probes, Inc.; Caltag Antibody Co.) are used to label lysosomal components that are localized in specific lysosomal domains. Examples of these components are the degradative enzymes involved in cholesterol ester hydrolysis, membrane protein proteases, and nucleases as well as the ATP-driven lysosomal proton pump.

In a third embodiment, protein chimeras consisting of a lysosomal protein genetically fused to an intrinsically luminescent protein such as the green fluorescent protein, or mutants thereof, are used to label the lysosomal domain. Examples of these components are the degradative enzymes involved in cholesterol ester hydrolysis, membrane protein proteases, and nucleases as well as the ATP-driven lysosomal proton pump.

Cytoplasmic Fluorescence Labeling

In one embodiment, cell permeant fluorescent dyes (Molecular Probes, Inc.) with a reactive group are reacted with living cells. Reactive dyes including monobromobimane, 5-chloromethylfluorescein diacetate, carboxy fluorescein diacetate succinimidyl ester, and chloromethyl tetramethylrhodamine are examples of cell permeant fluorescent dyes that are used for long term labeling of the cytoplasm of cells.

In a second embodiment, polar tracer molecules such as Lucifer yellow and cascade blue-based fluorescent dyes (Molecular Probes, Inc.) are introduced into cells using bulk loading methods and are also used for cytoplasmic labeling.

In a third embodiment, antibodies against cytoplasmic components (Sigma Chemical Co.; Molecular Probes, Inc.; Caltag Antibody Co.) are used to fluorescently label the cytoplasm. Examples of cytoplasmic antigens are many of the enzymes involved in intermediary metabolism. Enolase, phosphofructokinase, and acetyl-CoA dehydrogenase are examples of uniformly distributed cytoplasmic antigens.

In a fourth embodiment, protein chimeras consisting of a cytoplasmic protein genetically fused to an intrinsically luminescent protein such as the green fluorescent protein, or mutants thereof, are used to label the cytoplasm. Fluorescent chimeras of uniformly distributed proteins are used to label the entire cytoplasmic domain. Examples of these proteins are many of the proteins involved in intermediary metabolism and include enolase, lactate dehydrogenase, and hexokinase.

In a fifth embodiment, antibodies against cytoplasmic antigens (Sigma Chemical Co.; Molecular Probes, Inc.; Caltag Antibody Co.) are used to label cytoplasmic components that are localized in specific cytoplasmic sub-domains. Examples of these components are the cytoskeletal proteins actin, tubulin, and cytokeratin. A population of these proteins within cells is assembled into discrete structures, which in this case, are fibrous. Fluorescence labeling of these proteins with antibody-based reagents therefore labels a specific sub-domain of the cytoplasm.

In a sixth embodiment, non-antibody-based fluorescently labeled molecules that interact strongly with cytoplasmic proteins are used to label specific cytoplasmic components. One example is a fluorescent analog of the enzyme DNAse I (Molecular Probes, Inc.) Fluorescent analogs of this enzyme bind tightly and specifically to cytoplasmic actin, thus labeling a sub-domain of the cytoplasm. In another example, fluorescent analogs of the mushroom toxin phalloidin or the drug paclitaxel (Molecular Probes, Inc.) are used to label components of the actin- and microtubule-cytoskeletons, respectively.

In a seventh embodiment, protein chimeras consisting of a cytoplasmic protein genetically fused to an intrinsically luminescent protein such as the green fluorescent protein, or mutants thereof, are used to label specific domains of the cytoplasm. Fluorescent chimeras of highly localized proteins are used to label cytoplasmic sub-domains. Examples of these proteins are many of the proteins involved in regulating the cytoskeleton. They include the structural proteins actin, tubulin, and cytokeratin as well as the regulatory proteins microtubule associated protein 4 and α-actinin.

Nuclear Labeling

In one embodiment, membrane permeant nucleic-acid-specific luminescent reagents (Molecular Probes, Inc.) are used to label the nucleus of living and fixed cells. These reagents include cyanine-based dyes (e.g., TOTO®, YOYO®, and BOBO™), phenanthidines and acridines (e.g., ethidium bromide, propidium iodide, and acridine orange), indoles and imidazoles (e.g., Hoechst 33258, Hoechst 33342, and 4',6-diamidino-2-phenylindole), and other similar reagents (e.g., 7-aminoactinomycin D, hydroxystilbamidine, and the psoralens).

In a second embodiment, antibodies against nuclear antigens (Sigma Chemical Co.; Molecular Probes, Inc.; Caltag Antibody Co.) are used to label nuclear components that are localized in specific nuclear domains. Examples of these components are the macromolecules involved in maintaining DNA structure and function. DNA, RNA, histones, DNA polymerase, RNA polymerase, lamins, and nuclear variants of cytoplasmic proteins such as actin are examples of nuclear antigens.

In a third embodiment, protein chimeras consisting of a nuclear protein genetically fused to an intrinsically luminescent protein such as the green fluorescent protein, or mutants thereof, are used to label the nuclear domain. Examples of these proteins are many of the proteins involved in maintaining DNA structure and function. Histones, DNA polymerase, RNA polymerase, lamins, and nuclear variants of cytoplasmic proteins such as actin are examples of nuclear proteins.

Mitochondrial Labeling

In one embodiment, membrane permeant mitochondrial-specific luminescent reagents (Molecular Probes, Inc.) are used to label the mitochondria of living and fixed cells. These reagents include rhodamine 123, tetramethyl rosamine, JC-1, and the MitoTracker reactive dyes.

In a second embodiment, antibodies against mitochondrial antigens (Sigma Chemical Co.; Molecular Probes, Inc.; Caltag Antibody Co.) are used to label mitochondrial components that are localized in specific mitochondrial domains. Examples of these components are the macromolecules involved in maintaining mitochondrial DNA structure and function. DNA, RNA, histones, DNA polymerase, RNA polymerase, and mitochondrial variants of cytoplasmic macromolecules such as mitochondrial tRNA and rRNA are examples mitochondrial antigens. Other examples of mitochondrial antigens are the components of the oxidative phosphorylation system found in the mitochondria (e.g., cytochrome c, cytochrome c oxidase, and succinate dehydrogenase).

In a third embodiment, protein chimeras consisting of a mitochondrial protein genetically fused to an intrinsically luminescent protein such as the green fluorescent protein, or mutants thereof, are used to label the mitochondrial domain. Examples of these components are the macromolecules involved in maintaining mitochondrial DNA structure and function. Examples include histones, DNA polymerase, RNA polymerase, and the components of the oxidative phosphorylation system found in the mitochondria (e.g., cytochrome c, cytochrome c oxidase, and succinate dehydrogenase).

Endoplasmic Reticulum Labeling

In one embodiment, membrane permeant endoplasmic reticulum-specific luminescent reagents (Molecular Probes, Inc.) are used to label the endoplasmic reticulum of living and fixed cells. These reagents include short chain carbocyanine dyes (e.g., $DiOC_6$ and $DiOC_3$), long chain carbocyanine dyes (e.g., $DiIC_{16}$ and $DiIC_{18}$), and luminescently labeled lectins such as concanavalin A.

In a second embodiment, antibodies against endoplasmic reticulum antigens (Sigma Chemical Co.; Molecular Probes, Inc.; Caltag Antibody Co.) are used to label endoplasmic reticulum components that are localized in specific endoplasmic reticulum domains. Examples of these components are the macromolecules involved in the fatty acid elongation systems, glucose-6-phosphatase, and HMG CoA-reductase.

In a third embodiment, protein chimeras consisting of a endoplasmic reticulum protein genetically fused to an intrinsically luminescent protein such as the green fluorescent protein, or mutants thereof, are used to label the endoplasmic reticulum domain. Examples of these components are the macromolecules involved in the fatty acid elongation systems, glucose-6-phosphatase, and HMG CoA-reductase.

Golgi Labeling

In one embodiment, membrane permeant Golgi-specific luminescent reagents (Molecular Probes, Inc.) are used to label the Golgi of living and fixed cells. These reagents include luminescently labeled macromolecules such as wheat germ agglutinin and Brefeldin A as well as luminescently labeled ceramide.

In a second embodiment, antibodies against Golgi antigens (Sigma Chemical Co.; Molecular Probes, Inc.; Caltag Antibody Co.) are used to label Golgi components that are localized in specific Golgi domains. Examples of these components are N-acetylglucosamine phosphotransferase, Golgi-specific phosphodiesterase, and mannose-6-phosphate receptor protein.

In a third embodiment, protein chimeras consisting of a Golgi protein genetically fused to an intrinsically luminescent protein such as the green fluorescent protein, or mutants thereof, are used to label the Golgi domain. Examples of these components are N-acetylglucosamine phosphotransferase, Golgi-specific phosphodiesterase, and mannose-6-phosphate receptor protein.

While many of the examples presented involve the measurement of single cellular processes, this is again is intended for purposes of illustration only. Multiple parameter high-content screens can be produced by combining several single parameter screens into a multiparameter high-content screen or by adding cellular parameters to any existing high-content screen. Furthermore, while each example is described as being based on either live or fixed cells, each high-content screen can be designed to be used with both live and fixed cells.

Those skilled in the art will recognize a wide variety of distinct screens that can be developed based on the disclosure provided herein.

We claim:

1. An automated method for analyzing cell spreading comprising:
    a) providing a substrate comprising an array of locations which contain multiple cells that are to be contacted with a test stimulus, wherein the cells possess at least a first luminescent reporter that is present in and can be used to identify cell cytoplasm;
    b) contacting the cells with the test stimulus;
    c) scanning multiple cells in each of the locations containing cells to acquire luminescent signals from the at least first luminescent reporter;
    d) creating a cytoplasmic image from the luminescent signals from the at least first luminescent reporter;
    e) creating a cytoplasmic mask from the cytoplasmic image;
    f) identifying cytoplasmic objects in the cytoplasmic mask;
    g) automatically measuring the following cell-based morphological features from the cytoplasmic object:
        i) One or more of cell area and cell perimeter; and
        ii) Cell shape, wherein cell shape is measured by determining one or more of cell box-fill ratio, cell height-width ratio, cytoplasm maximum width, cytoplasm minimum width, cell roundness, cell P2A which is defined as the cell perimeter, "P", squared divided by $4\pi$ times the cell area, and cytoplasm aspect ratio; and
    h) automatically determining the following well-based or field-based morphological features:
        i) one or more of a number of cytoplasmic objects in the field or well and an average of any of the cell-based morphological features in the field or well; and
        ii) a percentage of cells with any of the cell-based morphological features above a threshold value;
    wherein the morphological features in steps g) and h) provide a measure of cell spreading caused by the test stimulus.

2. The method of claim 1 wherein the cell-based morphological feature comprises both cell area and cell perimeter.

3. The method of claim 1 wherein cell shape is determined by one or more of cell roundness and cell P2A.

4. The method of claim 1 wherein the field-based or well-based morphological features comprise two or more members selected from the group consisting of:
    a) a percentage of cells with a cell area above a threshold value;
    b) a percentage of cells with a perimeter above a threshold value; and
    c) a percentage of cells with a cell P2A above a threshold value.

5. The method of claim 1 where the cytoplasmic object is a colony of cells, and the morphological features provide a measure of aggregate cell spreading.

6. The method of claim 1, wherein the method is used to analyze the effect of the test stimulus on cell spreading associated with a condition selected from the group consisting of tumor growth and metastasis, angiogenesis, thrombosis, restenosis, vascular overgrowth during macular degeneration, foam cell formation, inflammatory diseases, wound healing, scar reduction, and neurodegenerative diseases.

7. The method of claim 1 wherein the cells further possess a second luminescent reporter that is present in and can be used to identify cell nuclei, and wherein the method further comprises:
    a) acquiring luminescent signals from the second luminescent reporter;
    b) acquiring a nuclear image from the luminescent signals from the second luminescent reporter;

c) creating a nuclear mask from the nuclear image;

d) identifying nuclear objects in the nuclear mask; and e) automatically determining one or both of the following:
   i) a number of nuclear objects in each cytoplasmic object; and
   ii) a specific cytoplasmic object that each nuclear object is located on.

8. The method of claim 7, further comprising calculating one of the following cell-based morphological features:
   a) Nuclear area;
   b) Nuclear count;
   c) Cell area minus nuclear area; and
   a) Cell area divided by nuclear area.

9. The method of claim 8 wherein the field-based or well-based morphological features comprise one or more member selected from the group consisting of:
   a) a percentage of cells with a cell area minus nuclear area above a threshold value; and
   b) a percentage of cells with a cell area divided by nuclear area above a threshold value.

10. The method of claim 9 wherein the well-based or field-based morphological feature comprises a percentage of cells with a cell area minus nuclear area above a threshold value.

11. The method of claim 1 further comprising providing locations which contain multiple cells on the same substrate or on a different substrate that are not to be contacted with the test stimulus, wherein the cell-based morphological features provide a measure of cell spreading in the absence of the test stimulus, and wherein the measure of cell spreading caused by the test stimulus is compared with the measure of cell spreading in the absence of the test stimulus.

12. The method of claim 1 wherein the measurements are made at multiple time points.

* * * * *